United States Patent
Grue-Sørensen et al.

(10) Patent No.: US 9,656,945 B2
(45) Date of Patent: May 23, 2017

(54) 3-ACYL-INGENOLS II

(75) Inventors: Gunnar Grue-Sørensen, Ballerup (DK); Xifu Liang, Ballerup (DK); Thomas Högberg, Ballerup (DK); Kristoffer Månsson, Ballerup (DK); Per Vedsø, Ballerup (DK)

(73) Assignee: LEO LABORATORIES LIMITED, Dublin (IE)

( * ) Notice: Subject to any disclaimer, the term of this patent is extended or adjusted under 35 U.S.C. 154(b) by 243 days.

(21) Appl. No.: 13/997,011

(22) PCT Filed: Dec. 22, 2011

(86) PCT No.: PCT/DK2011/000155
§ 371 (c)(1),
(2), (4) Date: Aug. 22, 2013

(87) PCT Pub. No.: WO2012/083954
PCT Pub. Date: Jun. 28, 2012

(65) Prior Publication Data
US 2013/0331446 A1 Dec. 12, 2013

Related U.S. Application Data

(60) Provisional application No. 61/426,375, filed on Dec. 22, 2010, provisional application No. 61/494,148, filed on Jun. 7, 2011.

(51) Int. Cl.
*C07C 69/013* (2006.01)
*C07C 69/74* (2006.01)
*C07C 69/75* (2006.01)
*C07C 69/753* (2006.01)
*C07C 69/76* (2006.01)
*C07C 69/78* (2006.01)
*C07C 69/92* (2006.01)
*A61K 31/215* (2006.01)
*A61K 31/235* (2006.01)
*A61K 31/245* (2006.01)
(Continued)

(52) U.S. Cl.
CPC ............ *C07C 69/74* (2013.01); *A61K 31/215* (2013.01); *A61K 31/235* (2013.01); *A61K 31/245* (2013.01); *A61K 31/277* (2013.01); *A61K 45/06* (2013.01); *C07C 69/013* (2013.01); *C07C 69/75* (2013.01); *C07C 69/753* (2013.01); *C07C 69/76* (2013.01); *C07C 69/78* (2013.01); *C07C 69/92* (2013.01); *C07C 229/56* (2013.01); *C07C 229/58* (2013.01); *C07C 229/64* (2013.01); *C07C 233/54* (2013.01); *C07C 255/46* (2013.01); *C07C 2101/02* (2013.01); *C07C 2101/04* (2013.01); *C07C 2101/08* (2013.01); *C07C 2101/14* (2013.01); *C07C 2101/16* (2013.01); *C07C 2103/86* (2013.01)

(58) Field of Classification Search
CPC ... C07C 2103/86; C07C 69/013; C07C 69/74; C07C 69/75; C07C 69/753; C07C 69/76; C07C 69/78; C07C 69/92; A61K 31/215; A61K 31/235; A61K 31/245
See application file for complete search history.

(56) References Cited

U.S. PATENT DOCUMENTS

| 4,716,179 A | 12/1987 | Hecker et al. |
| 2009/0215884 A1* | 8/2009 | Ogbourne et al. ............ 514/450 |

FOREIGN PATENT DOCUMENTS

| AU | 2006201661 A1 | 11/2007 |
| AU | 2010200429 A1 | 2/2010 |

(Continued)

OTHER PUBLICATIONS

Grue-Sorensen et al., "Synthesis, Biological Evaluation and SAR of 3-benzoates of Ingenol for Treatment of Actinic Keratosis and Non-Melanoma Skin Cancer", Bioorganic & Medicinal Chemistry Letters 24, 2014, pp. 54-60.
Beeby, Angeloyl Chloride:Synthesis and Utilisation in the Partial Synthesis of Lantadene a (Rehmannic Acid), Tetrahedron Letters, No. 38, 1977, pp. 3379-3382.

(Continued)

*Primary Examiner* — Kendra D Carter
(74) *Attorney, Agent, or Firm* — Birch, Stewart, Kolasch & Birch, LLP

(57) ABSTRACT

The invention relates to compounds of general formula I, (I), wherein R is wherein R is aryl substituted by R3; or R is (C3-Ci3)-cycloalkyl, (C3-Ci3)-cycloalkenyl or (C7-Ci3)-cycloalkynyl optionally substituted by R4; and pharmaceutically acceptable salts, hydrates, or solvates thereof, for use—alone or in combination with one or more other pharmaceutically active compounds—in therapy, for preventing, treating or ameliorating diseases or conditions responsive to stimulation of neutrophil oxidative burst, responsive to stimulation of keratinocyte IL-8 release or responsive to induction of necrosis.

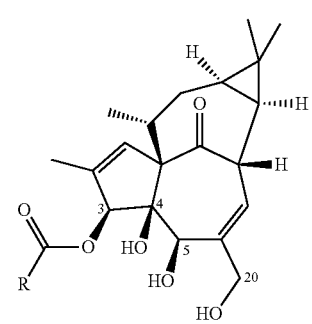

7 Claims, No Drawings

(51) Int. Cl.
- C07C 229/56 (2006.01)
- C07C 229/58 (2006.01)
- C07C 229/64 (2006.01)
- C07C 233/54 (2006.01)
- C07C 255/46 (2006.01)
- A61K 31/277 (2006.01)
- A61K 45/06 (2006.01)

(56) References Cited

FOREIGN PATENT DOCUMENTS

| | | |
|---|---|---|
| CA | 2 541 903 A1 | 10/2007 |
| JP | 7-165600 A | 6/1995 |
| JP | 7-258168 A | 10/1995 |
| JP | 8-245505 A | 9/1996 |
| WO | WO 99/08994 A1 | 2/1999 |
| WO | WO 01/93883 A1 | 12/2001 |
| WO | WO 01/93884 A1 | 12/2001 |
| WO | WO 01/93885 A1 | 12/2001 |
| WO | WO 02/11743 A2 | 2/2002 |
| WO | WO 2005/065696 A1 | 7/2005 |
| WO | WO 2006/063382 A1 | 6/2006 |
| WO | WO 2006/116897 A1 | 11/2006 |
| WO | WO 2007/059584 A1 | 5/2007 |
| WO | WO 2008/131491 A1 | 11/2008 |
| WO | WO 2010/091472 A1 | 8/2010 |

OTHER PUBLICATIONS

Blanco-Molina et al., "Ingenol Esters Induce Apoptosis in Jurkat Cells through an AP-1 and NK-KB Independent Pathway", Chemistry & Biology 8, 2001, pp. 767-778.
Bohlmann et al., "Struktur and Synthese eines aus *Bellis perennis* L. Isolierten Diesters", Chem. Ber., 103, 1970, pp. 561-563.
Challacombe et al., Neutrophils are a Key Component of the Antitumor Efficacy of Topical Chemotherapy with Ingenol-3-Angelate:, J. Immunol, 177, 2006, pp. 8123-8132.
Cozzi, et al., "Induction of Senescene in Diterpene Ester-Treated Melanoma Cells via Protein Kinase C-Dependent Hyperactivation of the Mitogen-Activated Protein Kinase Pathway", Cancer Research, 66, 2006, pp. 10083-10091.
Ersvaer et al., The Protein Kinase C Agonist PEP005 (Ingenol 3-Angelate) in the Treatment of Human Cancer: A Balance Between Efficacy and Toxicity, Toxins, 2, 2010, pp. 174-194.
Gotta et al., On the Active Principles of the Euphorbiaceae, IXa Ingenane Type Diterpene Esters from Five Euphorbia Species, Z. Naturforsch. 39b, 1984, pp. 683-694.
Hampson et al., "PEP005, a Selective Small-Molecule Activator of Protein Kinase C, has Potent Antileukemic Activity Mediated Via the Delta Isoform of PKC", Blood, 106, 2005, pp. 1362-1368.
Hamspon et al., "The anti-tumor agent, ingenol-3-angelate (PEP005), promotes the recruitment of cytotoxic neutrophils by activation of vascular endothelial cells in a PKC-8 dependent manner", Cancer Immunol Immunother, 57, 2008, pp. 1241-1251.
Hoskins et al., Pyrrolizidine Alkaloid Analogues. Preparation of Semisynthetic Esters of Retronecine, J. Chem. Soc. Perkin Trans., 1, 1977, pp. 538-544.
Le et al., "Immunostimulatory cancer chemotheraphy using local ingenol-3-angelate and synergy with immunotherapies", Vaccine, 27, 2009, pp. 3053-3062.
Marston et al., "On the Active Principles of the Euphorbiaceae", Planta Medica, vol. 47, 1983, pp. 141-147.
Ogbourne et al., "Antitumor Activity of 3-Ingenyl Angelate: Plasma Membrane and Mitochondrial Disruption and Necrotic Cell Death", Cancer Research, 64, 2004, pp. 2833-2839.
Rosen et al., "Dual Mechanism of Action of Ingenol Mebutate Gel for Topical Treatment of Actinic Keratoses: Rapid Lesion Necrosis Followed by Lesion-Specific Immune Response", J Am Acad Derm, 2012, 66, pp. 486-493.
Sorg et al., "Structure/Activity Realtionships of Polyfunctional Diterpenes of the Ingenane Type. I. Tumor-Promoting Activity of Homologous, Aliphatic 3-esters of Ingenol and of 7.8-isoingenol-3-Tetradecanoate", Carcinogenesis vol. 8, No. 1, 1987, pp. 1-4.
Sorg et al., Zur Chemie des Ingenols, II [1] Ester des Ingenols und des -Isoingenols, Z. Naturforsch. 37b, 1982, pp. 748-756.
Zayed et al., Dietary Cancer Risk from Conditional Cancerogens (Tumor Promoters) in Produce of Livestock Fed on Species of Spurge (Euphorbiaceae), J. Cancer Res. Clin. Oncol, 127, 2001, pp. 40-47.
ABO, "Irritancy of Ingenol Esters from Euphorbia Kamerunica", Fitoterapia, vol. LIX, No. 3, 1988, pp. 244-246.
Mainieri et al., "Synthesis of Sapintoxin D and N-Methylanthranilate-Based Fluorescent Bioprobes", Natural Product Communications, vol. 2, No. 4, 2007, pp. 375-379.
Appendino et al., "Synthesis of Modified Ingenol Esters," Eur. J. Org. Chem., 1999, pp. 3413-3420.
Translation of Decision to Grant issued in Russian Application No. 2013133866 dated Sep. 28, 2015.
Translation of Office Action issued in Chinese Application No. 201180068123.3 dated Aug. 17, 2015.
Translation of Office Action issued in Japanese Application No. 2013-545051 dated Aug. 11, 2015.

* cited by examiner

3-ACYL-INGENOLS II

CROSS REFERENCE TO RELATED APPLICATIONS

This application is the National Phase of PCT/DK2011/000155 filed on Dec. 22, 2011, which claims priority under 35 U.S.C. 119(e) to U.S. Provisional Application No. 61/426,375 filed on Dec. 22, 2010 and U.S. Provisional Application No. 61/494,148 filed on Jun. 7, 2011, all of which are hereby expressly incorporated by reference into the present application.

FIELD OF THE INVENTION

This invention relates to novel derivatives of 3-acyl-ingenol and derivatives thereof and their use as a medicament and in therapy. The invention also provides pharmaceutical compositions comprising said compounds and methods of treating diseases with said compounds.

BACKGROUND OF THE INVENTION

Ingenol-3-angelate (PEP005, ingenol mebutate) is a diterpene-ester of the ingenol family which is isolated from various *Euphorbia* species, particularly from *Euphorbia peplus*. The compound is presently subject for clinical development for the treatment of actinic keratosis and for non-melanoma skin cancer.

Ingenol-3-acylates, mainly of long-chain saturated and unsaturated aliphatic fatty acids, have been isolated from various *Euphorbia* species [H. Gotta, Z. Naturforschung, (1984), 39b, 683-94; K. Abo, Fitoterapia, (1988), 244-46, S. Zayed, 1 Cancer Res. Clin. Oncol. (2001), 127, 40-47]. Furthermore, a small number ingenol-3-acylates have been prepared by semi-synthesis (B. Sorg et. al., Z. Naturforsch., (1982), 37b, 748-56). Some of these ingenol derivatives have been described and tested to be strong irritants and strong tumor-promoting agents. [B. Sorg et. al., Z. Naturforsch., (1982), 37b, 748-56; B. Sorg et. al., Carcinogenesis, (1987), 8, 1-4].

Besides the aliphatic ingenol esters also aromatic esters of ingenol are known. Milliamine C, an ingenol-3-anthraniloate derivative was described (Marston, A. Planta Medica, (1983), 47, 141-47). Also ingenol-3-benzoate has been described (Sorg, B.; Z Naturforschung, (1982), 37b, 748-56), as well as ingenol-3-(2-methylamino)benzoate (Mainieri, F.; Natural Product Communication, (2007), 2(4), 375-379).

Angelic acid and angelic acid esters, as present in ingenol-3-angelate, are prone to isomerisation of the double bond to form the tiglate ester, particularly at basic pH [Beeby, P., *Tetrahedron Lett.* (1977), 38, 3379-3382, Hoskins, W. M., *J. Chem. Soc. Perkin Trans.* 1, (1977), 538-544, Bohlmann, F. et. al., *Chem. Ber.* (1970), 103, 561-563]. Furthermore, ingenol-3-acylates are known to be unstable as they rearrange to afford the ingenol-5-acylates and ingenol-20-acylates [Sorg, B. et. al, Z. Naturforsch., (1982), 37B, 748-756].

WO99/08994 describes isolation of compounds from *Euphorbia* plant and their use in cancer and other neoplastic diseases hereunder actinic keratosis or solar keratosis. WO01/93883 describes ingenol derivatives different from the present invention for prophylaxis of a PKC-related condition or disorder in a subject. Diseases mentioned in WO01/93883 are: asthma, atherosclerosis, atopic dermatitis, autoimmune disease, bipolar disorder, blood disorder, cardiac hypertrophy, depression, diabetes, hypertension, hyperplastic dermatosis, multiple sclerosis, myocardial ischemia, osteoarthritis, psoriasis, rheumatoid arthritis, transplantation and latent virus. WO01/93884 discloses ingenol derivatives different from the present invention, and their use in treating inflammatory conditions such as resulting from pathogenic organisms, virus, yeast, fungus, worms, insects, arachnids, nematodes, aemobe etc. WO01/93885 describes ingenol derivatives different from the present invention for immunopotentiation. WO08/131,491 describes ingenol derivatives different from the present invention for HPV virus infections. WO06/063382 discloses ingenol derivatives different from the present invention for treatment of solid cancers. AU 2006201661 discloses a method for treating acute myeloid leukemia using ingenol-3-angelate. WO02/11743 describes a particular use in prostate and bladder cancer. Ingenol derivatives are described in WO07/059,584 for promoting wound healing. WO2010/091472 describes use of ingenols and derivatives in other cosmetic applications.

Ingenol-3-angelate is believed to have a dual mode of action: 1) Induction of cell death by direct cytoxicity or induction of apoptosis and 2) an immunostimulatory effect dominated by neutrophil recruitment and activation (Rosen, R. H., et al., *J Am Acad Derm* (2011), e-published November 2011; Ersvaer, E., et al., *Toxins*, (2010), 2, 174-194). Nanomolar concentrations of the agent cause activation and modulation of protein kinase C (PKC) classical and novel isoforms, with particular importance of PKCdelta. Through activation of PKCdelta the agent induces apoptosis in susceptible cells (Hampson, P., et al., *Blood*, (2005), 106, 1362-1368; Cozzi, S. J., et al., *Cancer Res*, (2006), 66, 10083-10091). Rapid cytotoxicity on cancer cells is observed at high micromolar concentrations (Ogbourne, S. M., et al., *Cancer Res* (2004), 64, 2833-2839). Through activation of various PKC isoforms the agent also induces pro-inflammatory effects, including release of pro-inflammatory mediators (Challacombe, J. M., et al., *J Immunol* (2006), 177, 8123-8132, activation of vascular endothelium (Hampson, P., et al., *Cancer Immunol Immunother*, (2008), 57, 1241-1251); chemoattraction of neutrophils through induction of interleukin 8 in keratinocytes and development of specific anti-cancer immune responses by CD8+ cells through adjuvant properties in animal models (Le, T. T., et al., *Vacccine*, (2009), 27, 3053-3062).

Compounds exerting dual mode of action by induction of cell death by direct cytoxicity or induction of apoptosis, and by an immunostimulatory effect involving neutrophil recruitment and activation, may be useful for treatment of conditions associated with hyperplasia or neoplasia. Compounds inducing cell death by primary and/or secondary necrosis and compounds exhibiting a pro-apoptotic effect may reduce unwanted cell growth and remove unwanted cells, and furthermore, stimulation of the innate immune response and adjuvant effects may augment the biological response against aberrant or transformed cells.

Compounds inducing cell death by primary and/or secondary necrosis may be useful for treatment of cosmetic conditions, as these compounds may kill or remove unwanted tissue or cells.

There is a need to find new ingenol derivatives, with a similar or improved biological activity compared to ingenol-3-angelate, exhibiting suitable stability. Furthermore, there is a need to find new ingenol derivatives which induce cell death by cytotoxicity or apoptosis and/or induce an immunostimulatory effect.

The present invention provides aromatic or carbocyclic 3-O-acyl ingenol derivatives useful for treatment of conditions associated with the use of ingenol-3-angelate or useful for conditions which are affected by induction of cell death by cytotoxicity or induction of apoptosis and/or by an immunostimulatory effect.

Compounds of the present invention stimulate neutrophil oxidative burst, which is part of the innate immune response.

Compounds of the present invention stimulate keratinocyte IL-8 release, thus inducing an immunostimulatory effect.

Some compounds of the present invention induce rapid necrosis.

Compounds of the present invention exhibit suitable stability.

Some compounds of the present invention exhibit improved stability compared to ingenol-3-angelate.

Some compounds of the present invention exhibit improved activity in neutrophil oxidative burst assay compared to ingenol-3-angelate.

Some compounds of the present invention exhibit improved activity in IL-8 release assay compared to ingenol-3-angelate.

Some compounds of the present invention exhibit improved activity in necrosis assay compared to ingenol-3-angelate.

SUMMARY OF THE INVENTION

In an embodiment, the invention provides a compound of the general formula I

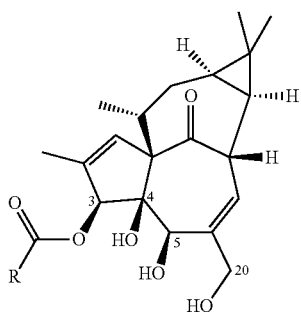

I wherein R is aryl substituted by one or more substituents independently selected from R3;
or R is $(C_3-C_{13})$-cycloalkyl, $(C_3-C_{13})$-cycloalkenyl or $(C_7-C_{13})$-cycloalkynyl each of which may optionally be substituted by one or more substituents independently selected from R4;
R3 represents halogen, cyano, hydroxyl;
or R3 represents $(C_1-C_4)$-alkyl, $(C_2-C_4)$-alkenyl, $(C_2-C_4)$-alkynyl, $(C_3-C_7)$-cycloalkyl, heterocycloalkyl, aryl, heteroaryl, each of which may optionally be substituted by one or more substituents independently selected from R5;
or R3 represents —NRaCORb, —CONRaRb, —COORc, —OCORa, —ORa, —OCONRaRb, —NRaCOORb, —NRaCONRaRb, —NRaSO2NRaRb, —NRaSO2Rb, —SO2NRaRb, —SO2Ra, —S(O)Ra, —SRa or —NRdRe;
R5 represents halogen, cyano, hydroxy, $(C_1-C_4)$-alkyl, halo$(C_1-C_4)$-alkyl or R5 represents —NRaCORb, —COORc, —OCORa, —CONRaRb, —OCONRaRb, —NRaCOORb, —NRaCONRaRb, —NRaSO2NRaRb, —NRaSO2Rb, —SO2NRaRb, —SO2Ra, —S(O)Ra, —ORa, —SRa, =O;

R4 represents halogen, cyano, hydroxyl;
or R4 represents $(C_1-C_4)$-alkyl, $(C_2-C_4)$-alkenyl, $(C_2-C_4)$-alkynyl, aryl, heteroaryl, $(C_3-C_7)$-cycloalkyl, heterocycloalkyl, each of which is optionally substituted by one or more substituents independently selected from R6,
or R4 represents —NRaCORb, —COORc, —OCORa, —CONRaRb, —OCONRaRb, —NRaCOORb, —NRaCONRaRb, —NRaSO2NRaRb, —NRaSO2Rb, —SO2NRaRb, —SO2Ra, —S(O)Ra, —ORa, —SRa, =O or —NRaRb;
R6 represents halogen, $(C_1-C_4)$-alkyl, cyano, hydroxy, halo$(C_1-C_4)$-alkyl, —NRaCORb, —COORc, —OCORa, —CONRaRb, —OCONRaRb, —NRaCOORb, —NRaCONRaRb, —NRaSO2NRaRb, —NRaSO2Rb, —SO2NRaRb, —SO2Ra, —S(O)Ra, —ORa, —SRa, =O;
Ra and Rb independently represents hydrogen, $(C_1-C_4)$-alkyl, $(C_2-C_4)$-alkenyl, $(C_2-C_4)$-alkynyl, aryl, heteroaryl, cycloalkyl, heterocycloalkyl, halo$(C_1-C_4)$-alkyl, $(C_1-C_4)$-alkoxy$(C_1-C_4)$-alkyl, hydroxy$(C_1-C_4)$-alkyl, cyano$(C_1-C_4)$-alkyl, said $(C_1-C_4)$-alkyl, $(C_1-C_4)$-alkenyl, aryl, heteroaryl, cycloalkyl or heterocycloalkyl optionally being substituted by one or more substituents selected from R7;
or when Ra and Rb are attached to the same nitrogen Ra and Rb may form a heterocyclic ring together with the nitrogen to which they are attached, said heterocyclic ring comprising up to two heteroatoms chosen from O, N or S, said heterocyclic ring optionally being substituted with $(C_1-C_4)$-alkyl;
Rc represents $(C_1-C_4)$-alkyl, halo$(C_1-C_4)$-alkyl, $(C_1-C_4)$-alkoxy$(C_1-C_4)$-alkyl, hydroxy$(C_1-C_4)$-alkyl, cyano$(C_1-C_4)$-alkyl-,
Rd and Re independently represents hydrogen, $(C_1-C_4)$-alkyl, $(C_3-C_4)$-alkenyl, $(C_3-C_4)$-alkynyl, aryl, heteroaryl, cycloalkyl, heterocycloalkyl, arylalkyl, heteroarylalkyl, cycloalkylalkyl, heterocycloalkylalkyl, halo$(C_1-C_4)$-alkyl, $(C_1-C_4)$-alkoxy$(C_1-C_4)$-alkyl, hydroxy$(C_1-C_4)$-alkyl or cyano$(C_1-C_4)$-alkyl, said $(C_1-C_4)$-alkyl, $(C_3-C_4)$-alkenyl, $(C_3-C_4)$-alkynyl, aryl, heteroaryl, cycloalkyl, heterocycloalkyl, arylalkyl, heteroarylalkyl, cycloalkylalkyl or heterocycloalkylalkyl optionally being substituted by one or more substituents selected from R7,
or Rd and Re may form a heterocyclic ring together with the nitrogen to which they are attached, said heterocyclic ring comprising up to two heteroatoms chosen from O, N or S, said heterocyclic ring optionally being substituted with $(C_1-C_4)$-alkyl;
R7 represents halogen, $(C_1-C_4)$-alkyl, cyano, halo$(C_1-C_4)$-alkyl, $(C_1-C_4)$-alkoxy, —NRfCORg, —COORf, —OCORf, —CONRfRg, —OCONRfRg, —NRfCOORg, —NRfCONRfRg, —NRfSO2Rg, —SO2NRfRg, —SO2Rf, —S(O)Rf;
Rf and Rg independently represents hydrogen or $(C_1-C_4)$-alkyl;
and pharmaceutically acceptable salts, prodrugs, hydrates and solvates thereof;
with the proviso that the compound is not ingenol-3-(2-methylamino-benzoate).

In an embodiment the invention provides a compound of formula I, for use as a medicament in therapy.

In an embodiment the invention provides a pharmaceutical composition comprising a compound of formula I or a pharmaceutically acceptable stereoisomer, salt or in vivo hydrolysable ester thereof together with a pharmaceutically acceptable vehicle or excipient.

In an embodiment the invention provides a pharmaceutical composition suitable for topical administration comprising a compound of formula I or a pharmaceutically acceptable stereoisomer, salt or in vivo hydrolysable ester thereof together with a pharmaceutically acceptable vehicle or excipient.

In an embodiment the invention provides a compound of formula I for use in the treatment, prevention, amelioration or prophylaxis of physiological disorders or diseases associated with hyperplasia or neoplasia.

In an embodiment the invention provides use of a compound of formula I for the manufacture of a medicament for the treatment, amelioration or prophylaxis of physiological disorders or diseases associated with hyperplasia or neoplasia.

In an embodiment the invention provides a method of preventing, treating, amelioration or prophylaxis of physiological disorders or diseases associated with hyperplasia or neoplasia by administration to a subject in need thereof a compound of formula I.

In an embodiment the invention provides a compound of formula I for use in the treatment or amelioration of cosmetic indications.

In an embodiment the invention provides use of compound according to formula I for the manufacture of a medicament for the treatment or amelioration of cosmetic indications.

In an embodiment the invention provides a method of treatment or amelioration of cosmetic indications by administration to a subject in need thereof a compound of formula I.

In an embodiment the invention provides a pharmaceutical composition comprising a compound of formula I or a pharmaceutically acceptable stereoisomer, salt or in vivo hydrolysable ester thereof in combination with one or more other therapeutically active agents.

DETAILED DESCRIPTION OF THE INVENTION

In an embodiment, the invention provides a compound of formula I above, wherein Rd and Re independently represents hydrogen, $(C_2-C_4)$-alkyl, $(C_3-C_4)$-alkenyl, $(C_3-C_4)$-alkynyl, aryl, heteroaryl, cycloalkyl, heterocycloalkyl, arylalkyl, heteroarylalkyl, cycloalkylalkyl, heterocycloalkylalkyl, halo$(C_1-C_4)$-alkyl, $(C_1-C_4)$-alkoxy$(C_1-C_4)$-alkyl, hydroxy$(C_1-C_4)$-alkyl or cyano$(C_1-C_4)$-alkyl, said $(C_2-C_4)$-alkyl, $(C_3-C_4)$-alkenyl, $(C_3-C_4)$-alkynyl, aryl, heteroaryl, cycloalkyl, heterocycloalkyl, arylalkyl, heteroarylalkyl, cycloalkylalkyl or heterocycloalkylalkyl optionally being substituted by one or more substituents selected from R7, wherein R7 is as defined above,
or Rd and Re may form a heterocyclic ring together with the nitrogen to which they are attached, said heterocyclic ring comprising up to two heteroatoms chosen from O, N or S, said heterocyclic ring optionally being substituted with $(C_1-C_4)$-alkyl.

In an embodiment, the invention provides a compound of formula I above, wherein R is aryl substituted by two or more substituents independently selected from R3; wherein R3 is as defined above;
or R is $(C_3-C_{13})$-cycloalkyl, $(C_3-C_{13})$-cycloalkenyl or $(C_7-C_{13})$-cycloalkynyl each of which may optionally be substituted by one or more substituents independently selected from R4; wherein R4 is as defined above.

In an embodiment, the invention provides a compound of formula I above, wherein R is aryl substituted by one or more substituents independently selected from R3; or R is $(C_3-C_{13})$-cycloalkyl or $(C_3-C_{13})$-cycloalkenyl, each of which may optionally be each be substituted by one or more substituents independently selected from R4;

R3 represents halogen, cyano, hydroxyl;
or R3 represents $(C_1-C_4)$-alkyl, $(C_2-C_4)$-alkenyl, $(C_3-C_7)$-cycloalkyl, heterocycloalkyl, aryl, heteroaryl, each of which may optionally be substituted by one or more substituents independently selected from R5;
or R3 represents —NRaCORb, —CONRaRb, —COORc, —OCORa, —ORa, —OCONRaRb, —NRaCOORb, —NRaCONRaRb, —NRaSO2NRaRb, —NRaSO2Rb, —SO2NRaRb, —SO2Ra, —S(O)Ra, —SRa;

R5 represents halogen, cyano, hydroxy, $(C_1-C_4)$-alkyl, halo$(C_1-C_4)$-alkyl or R5 represents —NRaCORb, —COORc, —OCORa, —CONRaRb, —OCONRaRb, —NRaCOORb, —NRaCONRaRb, —NRaSO2NRaRb, —NRaSO2Rb, —SO2NRaRb, —SO2Ra, —S(O)Ra, —ORa, —SRa, =O;

R4 represents halogen, cyano, hydroxyl;
or R4 represents $(C_1-C_4)$-alkyl, $(C_2-C_4)$-alkenyl, aryl, heteroaryl, $(C_3-C_7)$-cycloalkyl, heterocycloalkyl, each of which is optionally substituted by one or more substituents independently selected from R6
or R4 represents —NRaCORb, —COORc, —OCORa, —CONRaRb, —OCONRaRb, —NRaCOORb, —NRaCONRaRb, —NRaSO2NRaRb, —NRaSO2Rb, —SO2NRaRb, —SO2Ra, —S(O)Ra, —ORa, —SRa, =O;

R6 represents halogen, $(C_1-C_4)$-alkyl, cyano, hydroxy, halo$(C_1-C_4)$-alkyl, —NRaCORb, —COORc, —OCORa, —CONRaRb, —OCONRaRb, —NRaCOORb, —NRaCONRaRb, —NRaSO2NRaRb, —NRaSO2Rb, —SO2NRaRb, —SO2Ra, —S(O)Ra, —ORa, —SRa, =O;

Ra and Rb independently represents hydrogen, $(C_1-C_4)$-alkyl, halo$(C_1-C_4)$-alkyl, $(C_1-C_4)$-alkoxy$(C_1-C_4)$-alkyl, hydroxy$(C_1-C_4)$-alkyl, cyano$(C_1-C_4)$-alkyl;

Rc represents $(C_1-C_4)$-alkyl, halo$(C_1-C_4)$-alkyl, $(C_1-C_4)$-alkoxy$(C_1-C_4)$-alkyl, hydroxy$(C_1-C_4)$-alkyl, cyano$(C_1-C_4)$-alkyl;

In an embodiment the invention provides a compound of formula I above, wherein R is aryl;

In an embodiment the invention provides a compound of formula I above wherein R is aryl which is ortho-or meta-substituted relative to the carbonyl group by substituents selected from R3.

In an embodiment the invention provides a compound of formula I above wherein R is phenyl or naphtyl.

In an embodiment the invention provides a compound of formula I above wherein R3 is independently selected one or more times from aryl, $(C_1-C_4)$-alkyl, —ORa, —NRaCORb, hydroxyl, cyano and halogen.

In an embodiment the invention provides a compound of formula I above wherein R3 and R4 are independently selected from heteroaryl or heterocycloalkyl.

In an embodiment the invention provides a compound of formula I above wherein R5 and R6 are independently selected from —NRaCORb, —CONRaRb, —OCORa, —OCONRaRb, —NRaCOORb, —NRaCONRaRb, —NRaSO2Rb, —SO2NRaRb, —SO2Ra.

In an embodiment the invention provides a compound of formula I above, wherein R is $(C_3-C_{13})$-cycloalkyl, $(C_5-C_{13})$-cycloalkenyl or $(C_7-C_{13})$-cycloalkynyl.

In an embodiment the invention provides a compound of formula I above, wherein R is cyclopropyl, cyclobutyl, cyclopentyl, cyclohexyl, cyclohexenyl or noradamantyl.

In an embodiment the invention provides a compound of formula I above, wherein R3 and R4 are independently selected from —NRaCORb, —CONRaRb, —OCORa, —OCONRaRb, —NRaCOORb, —NRaCONRaRb, —NRaSO₂Rb, —SO₂NRaRb, —SO₂Ra.

In an embodiment the invention provides a compound of formula I above, wherein Rd and Re are independently selected from the group consisting of hydrogen, ($C_1$-$C_4$)-alkyl, aryl and arylalkyl.

In an embodiment the invention provides a compound of formula I above, wherein Rd and Re are independently selected from the group consisting of hydrogen, ($C_2$-$C_4$)-alkyl, aryl and arylalkyl.

In an embodiment the invention provides a compound of formula I above, wherein Rd and Re are independently selected from the group consisting of ($C_2$-$C_4$)-alkyl, aryl and arylalkyl.

In an embodiment the invention provides a compound of formula I above wherein R is phenyl which is ortho-substituted relative to the carbonyl group by one or two substituents independently selected from R3.

In an embodiment the invention provides a compound of formula I above wherein R is phenyl which is ortho-substituted relative to the carbonyl group by one substituent selected from R3.

In an embodiment the invention provides a compound of formula I above wherein R is phenyl which is substituted by one or more substituents independently selected from R3; and wherein at least one R3 is in a ortho-position relative to the carbonyl group.

In an embodiment the invention provides a compound of formula I above wherein R is phenyl which is substituted by two or more substituents independently selected from R3; and wherein at least one R3 is in a ortho-position relative to the carbonyl group.

In an embodiment the invention provides a compound of formula I above wherein R is phenyl which is ortho-substituted relative to the carbonyl group by two substituents selected independently from R3.

In an embodiment the invention provides a compound of formula I above wherein R is phenyl which is ortho-substituted relative to the carbonyl group by one substituent selected from R3 and wherein R3 represents halogen, cyano, hydroxyl;
or R3 represents ($C_1$-$C_4$)-alkyl, ($C_2$-$C_4$)-alkenyl, ($C_2$-$C_4$)-alkynyl, ($C_3$-$C_2$)-cycloalkyl, heterocycloalkyl, aryl, heteroaryl, each of which may optionally be substituted by one or more substituents independently selected from R5;
or R3 represents —NRaCORb, —CONRaRb, —COORc, —OCORa, —ORa, —OCONRaRb, —NRaCOORb, —NRaCONRaRb, —NRaSO2NRaRb, —NRaSO2Rb, —SO2NRaRb, —SO2Ra, —S(O)Ra, —SRa.

In an embodiment the invention provides a compound of formula I above wherein R is phenyl which is ortho-substituted relative to the carbonyl group by two substituent selected independently from R3 and wherein R3 represents halogen, cyano, hydroxyl;
or R3 represents ($C_1$-$C_4$)-alkyl, ($C_2$-$C_4$)-alkenyl, ($C_2$-$C_4$)-alkynyl, ($C_3$-$C_7$)-cycloalkyl, heterocycloalkyl, aryl, heteroaryl, each of which may optionally be substituted by one or more substituents independently selected from R5;
or R3 represents —NRaCORb, —CONRaRb, —COORc, —OCORa, —ORa, —OCONRaRb, —NRaCOORb, —NRaCONRaRb, —NRaSO2NRaRb, —NRaSO2Rb, —SO2NRaRb, —SO2Ra, —S(O)Ra, —SRa.

In an embodiment the invention provides a compound of formula I above wherein R is phenyl which is ortho-substituted relative to the carbonyl group by one substituent selected from R3 and wherein R3 represents halogen, cyano, hydroxyl;
or R3 represents ($C_1$-$C_4$)-alkyl, aryl or heteroaryl, each of which may optionally be substituted by one or more substituents independently selected from R5;
or R3 represents —ORa or —NRdRe.

In an embodiment the invention provides a compound of formula I above wherein R is phenyl which is ortho-substituted relative to the carbonyl group by two substituents independently selected from R3 and wherein R3 represents halogen, cyano, hydroxyl;
or R3 represents ($C_1$-$C_4$)-alkyl, aryl or heteroaryl, each of which may optionally be substituted by one or more substituents independently selected from R5;
or R3 represents —ORa or —NRdRe.

In an embodiment the invention provides a compound of formula I above wherein R is phenyl which is ortho-substituted relative to the carbonyl group by one substituent selected from R3 and wherein R3 represents halogen, cyano, hydroxyl;
or R3 represents ($C_1$-$C_4$)-alkyl, aryl or heteroaryl, each of which may optionally be substituted by one or more substituents independently selected from R5;
or R3 represents —ORa or —NRdRe; and wherein Rd and Re independently represents hydrogen, ($C_2$-$C_4$)-alkyl, aryl or arylalkyl; and wherein Ra represents ($C_1$-$C_4$)-alkyl or halo($C_1$-$C_4$)-alkyl.

In an embodiment the invention provides a compound of formula I above wherein R is phenyl which is ortho-substituted relative to the carbonyl group by two substituents independently selected from R3 and wherein R3 represents halogen, cyano, hydroxyl;
or R3 represents ($C_1$-$C_4$)-alkyl, aryl or heteroaryl, each of which may optionally be substituted by one or more substituents independently selected from R5;
or R3 represents —ORa or —NRdRe; and wherein Rd and Re independently represents hydrogen, ($C_2$-$C_4$)-alkyl, aryl or arylalkyl; and wherein Ra represents ($C_1$-$C_4$)-alkyl or halo($C_1$-$C_4$)-alkyl.

In an embodiment the invention provides a compound of formula I above wherein R is phenyl which is ortho-substituted relative to the carbonyl group by one substituent selected from R3 and wherein R3 represents halogen, cyano, hydroxyl;
or R3 represents ($C_1$-$C_4$)-alkyl, aryl or heteroaryl, each of which may optionally be substituted by one or more substituents independently selected from R5;
or R3 represents —ORa.

In an embodiment the invention provides a compound of formula I above wherein R is phenyl which is ortho-substituted relative to the carbonyl group by two substituents independently selected from R3 and wherein R3 represents halogen, cyano, hydroxyl;
or R3 represents ($C_1$-$C_4$)-alkyl, aryl or heteroaryl, each of which may optionally be substituted by one or more substituents independently selected from R5;
or R3 represents —ORa.

In an embodiment the invention provides a compound of formula I above wherein R is phenyl.

In an embodiment the invention provides a compound of formula I above wherein R is phenyl and wherein R3 represents halogen, cyano or hydroxyl;
or R3 represents ($C_1$-$C_4$)-alkyl, aryl or heteroaryl, each of which may optionally be substituted by one or more substituents independently selected from R5;
or R3 represents —ORa.

In an embodiment the invention provides a compound of formula I above wherein R is phenyl substituted by one or more substituents independently selected from R3;

or R is $(C_3-C_{10})$-cycloalkyl which may optionally be substituted by one or more substituents independently selected from R4;

In an embodiment the invention provides a compound of formula I above wherein R is R is $(C_3-C_{10})$-cycloalkyl or $(C_3-C_{13})$-cycloalkenyl each of which may optionally be substituted by one or more substituents independently selected from R4;

In an embodiment the invention provides a compound of formula I above wherein R is cyclopropyl, cyclobutyl, cyclopentyl, cyclohexyl, cyclohexenyl or noradamantyl, said cyclopropyl, cyclobutyl, cyclopentyl, cyclohexyl, cyclohexenyl or noradamantyl optionally being substituted by one or more substituents independently selected from R4; wherein R4 represents halogen or cyano or R4 represents $(C_1-C_4)$-alkyl.

In an embodiment the invention provides a compound of formula I above wherein R is cyclopropyl, cyclopentyl, cyclohexyl or cyclohexenyl, said cyclopropyl, cyclopentyl, cyclohexyl or cyclohexenyl optionally being substituted by one or more substituents independently selected from R4; wherein R4 represents $(C_1-C_4)$-alkyl.

In an embodiment the invention provides a compound of formula I above wherein R is R is $(C_3-C_{10})$-cycloalkyl or $(C_3-C_{13})$-cycloalkenyl each of which may optionally be substituted by one or more substituents independently selected from R4 wherein R4 is selected from $(C_1-C_4)$-alkyl.

In an embodiment the invention provides a compound of formula I above wherein R is R is $(C_3-C_{10})$-cycloalkyl which may optionally be substituted by one or more substituents independently selected from R4.

In an embodiment the invention provides a compound of formula I above wherein R is aryl substituted by one or more substituents independently selected from R3;

or R is $(C_3-C_{13})$-cycloalkyl or $(C_3-C_{13})$-cycloalkenyl each of which may optionally be substituted by one or more substituents independently selected from R4;

R3 represents halogen, cyano, hydroxyl;

or R3 represents $(C_1-C_4)$-alkyl, aryl or heteroaryl, each of which may optionally be substituted by one or more substituents independently selected from R5;

or R3 represents —NRaCORb, —CONRaRb, —COORc, —OCORa, —ORa, —SRa or —NRdRe;

R5 represents halogen, cyano, hydroxy, $(C_1-C_4)$-alkyl, halo$(C_1-C_4)$-alkyl or R5 represents —NRaCORb, —COORc, —OCORa, —CONRaRb, —OCONRaRb, —NRaCOORb, —NRaCONRaRb, —NRaSO2NRaRb, —NRaSO2Rb, —SO2NRaRb, —SO2Ra, —S(O)Ra, —ORa, —SRa, =O;

R4 represents halogen, cyano, hydroxyl;

or R4 represents $(C_1-C_4)$-alkyl, aryl or heteroaryl, each of which is optionally substituted by one or more substituents independently selected from R6 or R4 represents —NRaCORb, —COORc, —OCORa, —CONRaRb, —ORa, —SRa, =O or —NRaRb;

R6 represents halogen, $(C_1-C_4)$-alkyl, cyano, hydroxy, halo$(C_1-C_4)$-alkyl, —NRaCORb, —COORc, —OCORa, —CONRaRb, —OCONRaRb, —NRaCOORb, —NRaCONRaRb, —NRaSO2NRaRb, —NRaSO2Rb, —SO2NRaRb, —SO2Ra, —S(O)Ra, —ORa, —SRa, =O;

Ra and Rb independently represents hydrogen, $(C_1-C_4)$-alkyl, aryl, heteroaryl, cycloalkyl, heterocycloalkyl, halo$(C_1-C_4)$-alkyl, $(C_1-C_4)$-alkoxy$(C_1-C_4)$-alkyl, hydroxy$(C_1-C_4)$-alkyl, cyano$(C_1-C_4)$-alkyl, said $(C_1-C_4)$-alkyl, aryl, heteroaryl, cycloalkyl or heterocycloalkyl optionally being substituted by one or more substituents selected from R7;

or when Ra and Rb are attached to the same nitrogen Ra and Rb may form a heterocyclic ring together with the nitrogen to which they are attached, said heterocyclic ring comprising up to two heteroatoms chosen from O, N or S, said heterocyclic ring optionally being substituted with $(C_1-C_4)$-alkyl;

Rc represents $(C_1-C_4)$-alkyl, halo$(C_1-C_4)$-alkyl, $(C_1-C_4)$-alkoxy$(C_1-C_4)$-alkyl, hydroxy$(C_1-C_4)$-alkyl, cyano$(C_1-C_4)$-alkyl-, Rd and Re independently represents hydrogen, $(C_1-C_4)$-alkyl, aryl, heteroaryl, cycloalkyl, heterocycloalkyl, arylalkyl, heteroarylalkyl, cycloalkylalkyl, heterocycloalkylalkyl, halo$(C_1-C_4)$-alkyl, $(C_1-C_4)$-alkoxy$(C_1-C_4)$-alkyl, hydroxy$(C_1-C_4)$-alkyl or cyano$(C_1-C_4)$-alkyl, said $(C_1-C_4)$-alkyl, aryl, heteroaryl, cycloalkyl, heterocycloalkyl, arylalkyl, heteroarylalkyl, cycloalkylalkyl or heterocycloalkylalkyl optionally being substituted by one or more substituents selected from R7, or Rd and Re may form a heterocyclic ring together with the nitrogen to which they are attached, said heterocyclic ring comprising up to two heteroatoms chosen from O, N or S, said heterocyclic ring optionally being substituted with $(C_1-C_4)$-alkyl;

R7 represents halogen, $(C_1-C_4)$-alkyl, cyano, halo$(C_1-C_4)$-alkyl, $(C_1-C_4)$-alkoxy, —NRfCORg, —COORf, —OCORf, —CONRfRg, —OCONRfRg, —NRfCOORg, —NRfCONRfRg, —NRfSO2Rg, —SO2NRfRg, —SO2Rf, —S(O)Rf;

Rf and Rg independently represents hydrogen or $(C_1-C_4)$-alkyl;

and pharmaceutically acceptable salts, prodrugs, hydrates and solvates thereof;

With the proviso that the compound is not ingenol-3-(2-methylamino-benzoate).

In an embodiment the invention provides a compound of formula I above wherein R is aryl substituted by one or more substituents independently selected from R3;

or R is $(C_3-C_{13})$-cycloalkyl or $(C_3-C_{13})$-cycloalkenyl, each of which may optionally be each be substituted by one or more substituents independently selected from R4;

R3 represents halogen, cyano, hydroxyl;

or R3 represents $(C_1-C_4)$-alkyl, $(C_2-C_4)$-alkenyl, $(C_3-C_7)$-cycloalkyl, heterocycloalkyl, aryl, heteroaryl, each of which may optionally be substituted by one or more substituents independently selected from R5;

or R3 represents —NRaCORb, —CONRaRb, —COORc, —OCORa, —ORa, —OCONRaRb, —NRaCOORb, —NRaCONRaRb, —NRaSO2NRaRb, —NRaSO2Rb, —SO2NRaRb, —SO2Ra, —S(O)Ra, —SRa;

R5 represents halogen, cyano, hydroxy, $(C_1-C_4)$-alkyl, halo$(C_1-C_4)$-alkyl or R5 represents —NRaCORb, —COORc, —OCORa, —CONRaRb, —OCONRaRb, —NRaCOORb, —NRaCONRaRb, —NRaSO2NRaRb, —NRaSO2Rb, —SO2NRaRb, —SO2Ra, —S(O)Ra, —ORa, —SRa, =O;

R4 represents halogen, cyano, hydroxyl;

or R4 represents $(C_1-C_4)$-alkyl, $(C_2-C_4)$-alkenyl, aryl, heteroaryl, $(C_3-C_7)$-cycloalkyl, heterocycloalkyl, each of which is optionally substituted by one or more substituents independently selected from R6 or R4 represents —NRaCORb, —COORc, —OCORa, —CONRaRb, —OCONRaRb, —NRaCOORb, —NRaCONRaRb, —NRaSO2NRaRb, —NRaSO2Rb, —SO2NRaRb, —SO2Ra, —S(O)Ra, —ORa, —SRa, =O;

R6 represents halogen, $(C_1-C_4)$-alkyl, cyano, hydroxy, halo $(C_1-C_4)$-alkyl, —NRaCORb, —COORc, —OCORa, —CONRaRb, —OCONRaRb, —NRaCOORb, —NRaCONRaRb, —NRaSO2NRaRb, —NRaSO2Rb, —SO2NRaRb, —SO2Ra, —S(O)Ra, —ORa, —SRa, =O;

Ra and Rb independently represents hydrogen, $(C_1-C_4)$-alkyl, halo$(C_1-C_4)$-alkyl, $(C_1-C_4)$-alkoxy$(C_1-C_4)$-alkyl, hydroxy$(C_1-C_4)$-alkyl, cyano$(C_1-C_4)$-alkyl;

Rc represents $(C_1-C_4)$-alkyl, halo$(C_1-C_4)$-alkyl, $(C_1-C_4)$-alkoxy$(C_1-C_4)$-alkyl, hydroxy$(C_1-C_4)$-alkyl, cyano$(C_1-C_4)$-alkyl.

Specific examples of compounds of formula I may be selected from the group consisting of:
Ingenol 3-(2-phenyl-benzoate),
Ingenol 3-(naphthalene-1-carboxylate),
Ingenol 3-(2,4,6-trichloro-benzoate),
Ingenol 3-(2,6-dichloro-benzoate),
Ingenol 3-(2,6-dimethoxy-benzoate),
Ingenol 3-(2,6-dimethyl-benzoate),
Ingenol 3-(2,4-difluoro-benzoate),
Ingenol 3-(4-methoxy-benzoate),
Ingenol 3-(2-methoxy-benzoate),
Ingenol 3-(4-fluoro-benzoate),
Ingenol 3-(2-methyl-benzoate),
Ingenol 3-(1-cyano-cyclohexanecarboxylate),
Ingenol 3-(1-methyl-cyclohexanecarboxylate),
Ingenol 3-(noradamantane-3-carboxylate),
Ingenol 3-(1-methoxycarbonyl-cyclopropylcarboxylate),
Ingenol 3-(cyclohexene-1-carboxylate),
Ingenol 3-(cyclopentanecarboxylate),
Ingenol 3-(cyclobutanecarboxylate),
Ingenol 3-(cyclohexanecarboxylate),
Ingenol 3-(cyclopropanecarboxylate),
Ingenol 3-(2-bromo-benzoate),
Ingenol 3-(2-phenoxy-benzoate),
Ingenol 3-(2-isopropyl-benzoate),
Ingenol 3-(2-isopropoxy-benzoate),
Ingenol 3-(2,4,6-trimethyl-benzoate),
Ingenol 3-(2-allyloxy-6-methyl-benzoate),
Ingenol 3-(2-hydroxy-6-methyl-benzoate),
Ingenol 3-(2-chloro-6-methyl-benzoate),
Ingenol 3-(2,4-dimethoxy-6-methyl-benzoate),
Ingenol 3-(2-amino-benzoate),
Ingenol 3-(2-benzylamino-benzoate),
Ingenol 3-(2-benzylamino-6-methyl-benzoate),
Ingenol 3-(2-benzylamino-6-methoxy-benzoate),
Ingenol 3-(2-amino-6-methoxy-benzoate),
Ingenol 3-(2-amino-6-methyl-benzoate),
Ingenol 3-(2-phenylamino-benzoate),
Ingenol 3-(2-acetylamino-6-methyl-benzoate),
Ingenol 3-(2-methyl-6-(2-methylpropanoylamino)-benzoate),
Ingenol 3-(2-methyl-6-methylamino-benzoate),
Ingenol 3-(2-amino-6-chloro-benzoate),
Ingenol 3-(2-amino-6-fluoro-benzoate),
Ingenol 3-(2-chloro-6-methylamino-benzoate),
Ingenol 3-(2-fluoro-6-methylamino-benzoate),
Ingenol 3-(2,2,3,3-tetramethylcyclopropylcarboxylate) or
Ingenol 3-(2,6,6-trimethylcyclohexene-1-carboxylate).

An embodiment of the invention provides a compound of formula I, said compound being Ingenol 3-(2-amino-6-chloro-benzoate).

An embodiment of the invention provides a compound of formula I, said compound being Ingenol 3-(2,6-dimethyl-benzoate).

An embodiment of the invention provides a compound of formula I, said compound being Ingenol 3-(2-fluoro-6-methylamino-benzoate).

An embodiment of the invention provides a compound of formula I, said compound being Ingenol 3-(2-amino-6-methyl-benzoate).

An embodiment of the invention provides a compound of formula I, said compound being Ingenol 3-(2-amino-6-fluoro-benzoate), An embodiment of the invention provides a compound of formula I, said compound being Ingenol 3-(2-methyl-6-methylamino-benzoate).

An embodiment of the invention provides a compound of formula I, said compound being Ingenol 3-(2-chloro-6-methyl-benzoate).

An embodiment of the invention provides a compound of formula I, said compound being Ingenol 3-(2-chloro-6-methylamino-benzoate).

An embodiment of the invention provides a compound of formula I, said compound being Ingenol 3-(naphthalene-1-carboxylate).

In one or more embodiments of the present invention, the compounds of general formula I have a molecular weight below 800 Dalton, such as below 750 Dalton, e.g. below 700 Dalton, or below 650, 600 or 550 Dalton.

DEFINITIONS

In the present context, the term "$(C_a-C_b)$alkyl" wherein a and b are integers refers to a straight or branched chain alkyl radical having from a to b carbon atoms, such as 1-7, 1-6, 1-5, 1-4, 1-3, 1-2, 2-3, 2-4 or 2-5 carbon atoms. Thus when a is 1 and b is 7, for example, the term includes methyl, ethyl, n-propyl, isopropyl, n-butyl, isobutyl, sec-butyl, tert-butyl, pentyl, isopentyl, hexyl, isohexyl and heptyl.

The term "carbocyclic" refers to a mono-, bi-or tricyclic radical, including fused-, bridged-and spiro-cyclic radicals, having up to 13 ring atoms, such as up to 12, 10 or 8 ring atoms, such as 3-13, 3-10, 3-8, 3-6, 3-5, 5-10 or 6-9 ring atoms all of which are carbon, and includes aryl, cycloalkyl and cycloalkenyl.

The term "cycloalkyl" refers to a mono-, bi-or tricyclic saturated cycloalkane radical, comprising 3-13 carbon atoms, such as 3-10, 3-8, 3-6 or 3-5 carbon atoms and includes, for example, cyclopropyl, cyclobutyl, cyclopentyl, cyclohexyl, cycloheptyl, cyclooctyl, bicyclo[2.2.1]heptanyl and adamantyl.

The term "$(C_a-C_b)$alkenyl" wherein a and b are integers refers to a mono-, di-or tri-unsaturated straight or branched chain alkenyl radical having from a to b carbon atoms, such as 2-7, 2-6, 2-5, 2-4 or 2-3 carbon atoms. Thus when a is 2 and b is 7, for example, the term includes ethenyl, allyl, propenyl; 1-, 2-or 3-butenyl; 1-, 2-, 3-or 4-pentenyl; 1-, 2-, 3-, 4-or 5-hexenyl.

The term "cycloalkenyl" refers to mono-, di-or triunsaturated non-aromatic cyclic hydrocarbons radicals, including polycyclic radicals, comprising 3-13 carbon atoms, such as 5-13, 5-10, 5-8 or 5-6 carbon atoms and includes, for example, cyclobutenyl, cyclopentenyl or cyclohexenyl.

The term "cycloalkynyl" refers to non-aromatic cyclic hydrocarbons radicals, including polycyclic radicals comprising 1-2 C—C triple bonds, comprising 7-13 carbon atoms, such as 7-12, 7-10 or 7-9 carbon atoms.

The term "($C_a$-$C_b$)alkynyl" wherein a and b are integers refers to a straight or branched chain hydrocarbon radical having from a to b carbon atoms such as 2-7, 2-6, 2-5, 2-4 or 2-3 carbon atoms, comprising 1-2 C—C triple bonds. Thus when a is 2 and b is 7, for example, the term includes ethynyl, propynyl, butynyl, pentynyl or hexynyl.

The term "heterocyclic" refers to a carbocyclic radical as defined above, comprising 1-4 heteroatoms, such as 1-3, 1-2 or 2-3 heteroatoms, selected from O, N, or S, and includes heteroaryl, heterocycloalkyl and heterocycloalkenyl.

The term "heterocycloalkyl" refers to a cycloalkyl radical as defined above, including polycyclic radicals, optionally fused with carbocyclic rings, comprising 1-4 heteroatoms, such as 1-3, 1-2 or 2-4 heteroatoms, selected from O, N, or S, e.g. tetrahydrofuranyl, pyrrolidinyl, dioxolanyl, morpholinyl, imidazolidinyl, piperidinyl, or 5-oxabicyclo[2.2.2]octane.

The term "heterocycloalkenyl" refers to a cycloalkenyl radical as defined above, including polycyclic radicals, optionally fused with carbocyclic rings, comprising 1-4 heteroatoms, such as 1-3, 1-2 or 2-4 heteroatoms selected from O, N, or S, e.g. dihydropyranyl.

The term "aryl" refers to a radical of aromatic carbocyclic rings comprising 6-10 carbon atoms, in particular phenyl, and optionally fused carbocyclic rings with at least one aromatic ring, the radical being obtained by removing a hydrogen from any position of the carbocyclic ring. Thus the term includes for example phenyl, naphthyl, indenyl or indanyl.

The term "heteroaryl" refers to radicals of heterocyclic aromatic rings, optionally fused with carbocyclic rings or heterocyclic rings, comprising 1-4 heteroatoms such as 1-3, 1-2 or 2-4 heteroatoms, selected from O, S and N, and 1-12 carbon atoms, in particular 5-or 6-membered rings with 1-4 heteroatoms such as 1-3, 1-2 or 2-4 heteroatoms, or optionally fused bicyclic rings with 1-4 heteroatoms such as 1-3, 1-2 or 2-4 heteroatoms, and wherein at least one ring is aromatic. Thus the term includes, for example, pyridyl, quinolyl, isoquinolyl, indolyl, tetrazolyl, furyl, thiazolyl, imidazolyl, imidazo[1,2-a]pyrimidinyl, pyrrolyl, pyrazolyl, oxazolyl, isoxazolyl, oxadiazolyl, 1,2,4-triazolyl, thienyl, pyrazinyl, pyrimidinyl, 1,2,3-triazolyl, isothiazolyl, imidazo[2,1-b]thiazolyl, benzimidazolyl, benzofuranyl, benzofuranyl, benzothiophenyl, benzothiazolyl, benzooxazolyl, indazolyl.

The term "halogen" is intended to indicate a substituent from the 7th main group of the periodic table, preferably fluoro, chloro and bromo.

The term "alkoxy" is intended to indicate a radical of the formula —OR, wherein R is alkyl as indicated above, e.g. methoxy, ethoxy, n-propoxy, isopropoxy, butoxy, etc.

The term hydroxyalkyl is intended to indicate a primary, secondary or tertiary radical of the formula —R—OH, wherein R is alkyl as indicated above, e.g. hydroxymethyl or hydroxyethyl.

The term cyanoalkyl is intended to indicate a primary, secondary or tertiary radical of the formula —R—CN, wherein R is alkyl as indicated above, e.g. cyanomethyl or cyanoethyl.

The term haloalkyl is intended to indicate a primary, secondary or tertiary radical of the formula —R—$X_{(1-3)}$, wherein R is alkyl as indicated above, and X is halogen as indicated above, e.g. trifluoromethyl, 2,2,2-trifluoroethyl or difluoromethyl.

The term "alkoxyalkyl" is intended to indicate an alkyl radical as defined above, which is substituted with an alkoxy radical as defined above, i.e. —R—O—R, wherein each R is alkyl, same or different, as indicated above, e.g. methoxymethyl, ethoxymethyl.

The term "heteroarylalkyl" is intended to indicate a radical of the formula —R-Het, wherein R is alkyl as defined above and Het is heteroaryl as defined above such as (4-pyridyl)methyl-;

The term "arylalkyl" is intended to indicate a radical of the formula —R—Ar, wherein R' is alkyl as defined above and Ar is aryl as defined above, such as benzyl;

The term "cycloalkylalkyl" is intended to indicate a radical of the formula —R-cycloalkyl, wherein R is alkyl as defined above, such as cyclohexylmethyl-or cyclopropylmethyl-;

The term "heterocycloalkylalkyl" is intended to indicate a radical of the formula —R-heterocycloalkyl, wherein R is alkyl as defined above, such as tetrahydropyran-4-methyl;

Unless indicated otherwise, the nomenclature of substituents that are not explicitly defined herein are arrived at by naming the terminal portion of the functionality followed by the adjacent functionality towards the point of attachment. For example, the group "arylalkyl" refers to the group (aryl)-(alkyl)-.

The term 'substituted' as applied to any moiety herein is intended to indicate substitution with compatible substituents.

The phrase "R is phenyl which is ortho-substituted relative to the carbonyl group by one substituent" is intended to indicate a compound of the structure below:

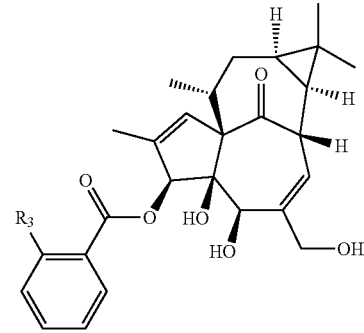

The phrase "R is phenyl which is ortho-substituted relative to the carbonyl group by two substituents" is intended to indicate a compound of the structure below:

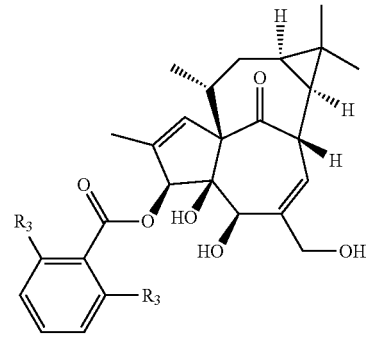

The term "pharmaceutically acceptable salt" is intended to indicate salts prepared by reacting a compound of formula I comprising a basic moiety with a suitable inorganic or organic acid, such as hydrochloric, hydrobromic, hydroiodic, sulfuric, nitric, phosphoric, formic, acetic, 2,2-dichloroacetic, choline, adipic, ascorbic, L-aspartic, L-glutamic, galactaric, lactic, maleic, L-malic, phthalic, citric, propionic, benzoic, glutaric, gluconic, D-glucuronic, methanesulfonic, salicylic, succinic, malonic, tartaric, benzenesulfonic, ethane-1,2-disulfonic, 2-hydroxy ethanesulfonic acid, toluenesulfonic, sulfamic or fumaric acid. Pharmaceutically acceptable salts of compounds of formula I comprising an acidic moiety may also be prepared by reaction with a suitable base such as sodium hydroxide, potassium hydroxide, magnesium hydroxide, calcium hydroxide, ammonia, or suitable non-toxic amines, such as lower alkylamines, for example triethylamine, hydroxy-lower alkylamines, for example 2-hydroxyethylamine, bis-(2-hydroxyethyl)-amine, cycloalkylamines, for example dicyclohexylamine, or benzylamines, for example N,N'-dibenzylethylenediamine, and dibenzylamine, or L-arginine or L-lysine.

In the present context the term "prodrug" is intended to indicate compounds in which for example hydroxyl groups or carboxylic acid groups are masked as groups which can be reconverted to hydroxyl groups or carboxylic acid groups respectively, in vivo so as to provide compounds of formula I upon administration to a patient. Examples of said groups are for example esters, e.g carboxylic acid esters (from hydroxyl groups and carboxylic acid groups) and phosphate acid esters (from hydroxyl groups) or amides (from carboxylic acid groups) or ethers (from hydroxyl groups), e.g. acetals and ketals.

The present invention further includes prodrugs of compounds of general formula I, such as esters, acetals, ketals, or other derivatives which undergo a biotransformation in vivo before exhibiting their pharmacological effects.

The term "solvate" is intended to indicate a species formed by interaction between a compound, e.g. a compound of formula I, and a solvent, e.g. alcohol, glycerol or water, wherein said species are in a solid form. When water is the solvent, said species is referred to as a hydrate.

The compounds of formula I may be obtained in crystalline form either directly by concentration from an organic solvent or by crystallisation or recrystallisation from an organic solvent or mixture of said solvent and a cosolvent that may be organic or inorganic, such as water. The crystals may be isolated in essentially solvent-free form or as a solvate, such as a hydrate. The invention covers all crystalline modifications and forms and also mixtures thereof.

The term "cancer" in the context of the present invention is intended to cover skin cancer such as non-melanoma skin cancer, malignant melanoma, Merkel cell carcinoma, squamous cell carcinoma, basal cell carcinoma. Basal cell carcinomas covers as well superficial basal cell carcinomas as nodular basal cell carcinoma. Squamous cell carcinoma covers squamous cell carcinoma in situ (Bowen's disease), invasive squamous cell carcinoma, cutaneous squamous cell carcinoma, mucosal squamous cell carcinoma, head and neck squamous cell carcinoma. Other cancer types includes haematological cancer such as myeloid cancers in particular such as acute myeloid leukemia and chronic myeloid leukemia; Cancer of the prostate and bladder including benign prostatic hyperplasia, prostatis intraepithelial carcinoma, carcinoma of the bladder, adenocarcinoma of the prostate and renal cell carcinoma. Other cancer include AIDS related cancer, acoustic neoma, adenocystic carcinoma, adrenocortical cancer, agnogenic myeloid metaplasia, alopecia, alveolar soft-part sarcoma, anal cancer, angiosarcoma, aplastic anaemia, astrocytoma, ataxia-telangiectasia, basal cell carcinoma (bcc), bladder cancer, bone cancers, bowel cancer, brain stem glioma, brain and CNS cancers, breast cancer, CNS cancers, carcinoid cancers, cervical cancer, childhood brain cancers, childhood cancer, childhood soft tissue sarcoma, chondrosarcoma, choriocarcinoma, colorectal cancers, cutaneous T-Cell lymphoma, dermatof[iota]brosarcoma-protuberans, desmoplastic small round cell cancer, ductal carcinoma, endocrine cancers, endometrial cancer, ependymoma, esophageal cancer, Ewing's sarcoma, extra hepatic bile duct cancer, eye cancer, eye: melanoma, retinoblastoma, fallopian tube cancer, fanconi anaemia, fibrosarcoma, gall bladder cancer, gastric cancer, gastrointestinal cancers, gastrointestinal carcinoid cancer, genitourinary cancers, germ cell cancers, gestational trophoblastic disease, glioma, gynecological cancers, hematological malignancies, including acute myeloid leukemia, head and neck cancer, hepatocellular cancer, hereditary breast cancer, histiocytosis, Hodgkin's disease, human papillomavirus, hydatidiform mole, hypercalcemia, hypopharynx cancer, intra-ocular melanoma, isle T-cell cancer, Kaposi's sarcoma, kidney cancer, Langerhan's cell histiocytosis, laryngeal cancer, leiomyosarcoma, li-fraumeni syndrome, lip cancer, liposarcoma, liver cancer, lung cancer, lymphedema, lymphoma, Hodgkin's lymphoma, non-Hodgkin's lymphoma, male breast cancer, malignant rhabdoid cancer of kidney, medulloblastoma, mesothelioma, metastatic cancer, mouth cancer, multiple endocrine neoplasia, mycosis fungoides, myelodysplastic syndromes, myeloma, myeloproliferative disorders, nasal cancer, nasopharyngeal cancer, nephroblastoma, neuroblastoma, neurofibromatosis, nijmegen breakage syndrome, non-small cell lung cancer (nscic), ocular cancers, oesophageal cancer, oral cavity cancer, oropharynx cancer, osteosarcoma, ostomy ovarian cancer, pancreas cancer, paranasal cancer, parathyroid cancer, parotid gland cancer, penile cancer, peripheral neuroectodermal cancers, pituitary cancer, polycythemia vera, prostate cancer, rare cancers and associated disorders, retinoblastoma, rhabdomyosarcoma, rothmund Thomson syndrome, salivary gland cancer, sarcoma, schwannoma, sezary syndrome, small cell lung cancer (scic), small intestine cancer, soft tissue sarcoma, spinal cord cancers, stomach cancer, synovial sarcoma, testicular cancer, thymus cancer, thyroid cancer, transitional cell cancer (bladder), transitional cell cancer (renal-pelvis−/− ureter), trophoblastic cancer, urethral cancer, urinary system cancer, uroplakins, uterine sarcoma, uterus cancer, vaginal Cancer, vulva cancer, Waldenstrom's macroglobulinemia and Wilms' Cancer. The solid cancer which is treated using the methods of the present invention may be a primary lesion or may be the result of metastasis of a primary cancer. Furthermore, if the solid cancer is a metastasis of a primary cancer, the primary cancer may be either a primary solid cancer as described above or may be a dispersed primary cancer.

In an embodiment of the invention "cancer" is skin cancer. In embodiments of the invention, skin cancer is non-melanoma skin cancer, malignant melanoma, Merkel cell carcinoma, squamous cell carcinoma, squamous cell carcinoma, basal cell carcinoma such as superficial basal cell carcinomas or nodular basal cell carcinoma.

The term "photodamaged skin" in the context of the present invention is intended to cover fine lines, wrinkles and UV-ageing. UV ageing is often manifested by an increase in the epidermal thickness or epidermal atrophy and most notably by solar elastosis, the accumulation of elastin containing material just below the dermal-epidermal junction. Collagen and elastic fibres become fragmented and disorganised. At a cosmetic level this can be observed as a reddening and/or thickening of the skin resulting a leathery appearance, skin fragility and irregular pigmentation, loss of tone and elasticity, as well as wrinkling, dryness, sunspots and deep furrow formation.

The term "viral infections" in the context of the present invention is intended to cover HPV infections leading to formation of warts on the body, such as the skin, genitals and mouth. HPV refers to human papilloma virus. Other viruses are selected from adeno-, papova-, herpes-(such as simplex) varicella-zoster, Epstein-Barr-, CMV-, Pox-(such as small pox-) vaccinia-, hepatitis A-, hepatitis B-, hepatitis C—, Rhino-, polio-, rubella-, arbo-, rabies-, influenza-A and B, measles-, mumps-viruses, and HIV, HTLV I and II. In an embodiment of the invention HPV infection refers to common warts or genital warts.

The term "bacterial infections" in the context of the present invention is intended to cover prokaryotic and eukaryotic bacterial infections and Gram positive and Gram negative and Gram variable bacteria and intracellular bacteria. Examples of bacteries includes *Treponema, Borrelia, Neisseria, Legionella, Bordetella, Escherichia, Salmonella, Shigella, Klebsiella, Yersinia, Vibrio, Hemophilus, Rickettsia, Chlamydia, Mycoplasma, Staphylococcus, Streptococcus, Bacillus, Clostridium, Corynebacterium, Proprionibacterium, Mycobacterium, Ureaplasma* and *Listeria*. In particular the species: *Treponema pallidum, Borrelia Burgdorferi, Neisseria gonorrhoea, Legionella pneumophila, Bordetella pertussis, Escherichia coli, Salmonella typhi, salmonella typhimurium, Shigella dysenteriae, Klebsiella pneumoniae, Yersinia pestis, Vibrio cholerae, Hemophilus influenza, Rickettsia rickettsii, Chlamydia trachomatis, Mycoplasma pneumonia, Staphylococcus aureus, Streptococcus pneumoniae, Streptococcus pyogenes, Bacillus anthracis, Clostridium botulinum, Clostridium tetani, clostridium perfringens, Corynebacterium diphteriae, Proprionibacterium acne, Mycobacterium tuberculosis, Mycobacterium leprae* and *Listeriare monocytogenes*. Lower eukaryotic organism includes yeast and fungus such as *Pneumocystis nerinii, Candida albicans, Aspergillus, Histoplasma capsulatum, Blastomyces dermatitidis, Cryptococcus neoformans, Trichophyton* and *Microsporum*. Complex eukaryotic organism includes worms, insects, aracnids, nematodes, aemobe, *Entamoeba histolytica, Giardia lamblia, Trichonomonas vaginalis, Trypanosoma brucei gembiense, Trypanosoma cruzi, Blantidium coli, Toxoplasma gondii, Cryptosporidium* or *Leishmania*.

The phrase "physiological disorders or diseases associated with hyperplasia or neoplasia" in the context of the present invention is intended to cover disorders or diseases such as Cutaneous warts including common warts (*Verruca vulgaris*), plantar warts (*Verruca plantaris*) and flat warts (*verruca plana*); Genital warts (condyloma acuminatum), Pyogenic granuloma, Haemangioma, Scleroderma; Cancers and precancerous lesions such as Actinic keratosis, Squamous cell carcinoma including squamous cell carcinoma in situ (Bowen's disease), invasive squamous cell carcinoma, cutaneous squamous cell carcinoma, mucosal squamous cell carcinoma, head and neck squamous cell carcinoma; Basal cell carcinoma including Superficial basal cell carcinoma and Nodular basal cell carcinoma; Bladder cancer, Lentigo maligna, Cervical dysplasia, Vulva dysplasia and anal dysplasia, Primary melanoma in situ, Head and neck cancer, Cutaneous metastases of any cancer, Kaposi's sarcoma, Keratoacanthoma, Merkel cell tumor, Prostate cancer, Mycosis fungoides, Intraepithelial neoplasias including anal, cervical, ductal, oral, perianal, prostatic, penile, vaginal and vulvar intraepithelial neoplasia.

The term "cosmetic indications" in the context of the present invention is intended to cover indications such as: Photodamaged skin, Seborrheic keratosis, Scars, Keloids, Melasma, Poikiloderma of Civatte, Tattoo removal, Naevi, Skin tags.

In the context of the present invention the term "wound healing" means: reducing or minimizing scar tissue or improving cosmesis or functional outcome in a wound and scar reduction, wherein the wound is cutaneous, chronic or for example diabetes associated, and includes cuts and lacerations, surgical incisions, punctures, graces, scratches, compression wounds, abrasions, friction wounds, chronic wounds, ulcers, thermal effect wounds, chemical wounds, wounds resulting from pathogenic infections, skin graft/transplant donor and recipient sites, immune response conditions, oral wounds, stomach or intestinal wounds, damaged cartilage or bone, amputation sides and corneal lesions.

The compounds of the present invention are contemplated in the treatment of cancer, actinic keratosis, seborrheic keratosis, viral infections, bacterial infections, wound healing, and treatment of photodamaged skin.

In an embodiment of the invention the compounds of the invention are contemplated for use in the treatment of superficial basal cell carcinoma (BCC), nodular BCC, squamous cell carcinoma or squamous cell carcinoma in situ (SCCIS).

In an embodiment of the invention the compounds of the invention are contemplated for use in the treatment of actinic keratosis.

In an embodiment of the invention the compounds of the invention are contemplated for use in the treatment of Seborrheic keratosis.

In an embodiment of the invention the compounds of the invention are contemplated for use in the treatment of photodamaged skin.

In an embodiment of the invention the compounds of the invention are contemplated for use in the treatment of or lesions caused by HPV infection.

In an embodiment of the invention the lesions are common warts or genital warts.

In an embodiment of the invention the compounds of the invention are contemplated for use in the treatment of squamous cell carcinoma in situ or invasive squamous cell carcinoma.

In an embodiment of the invention the compounds of the invention are contemplated for use in the treatment of cutaneous squamous cell carcinoma, mucosal squamous cell carcinoma or head and neck squamous cell carcinoma.

In an embodiment of the invention the compounds of the invention are contemplated for use in the treatment of superficial basal cell carcinoma or nodular basal cell carcinoma.

In an embodiment of the invention the compounds of the invention are contemplated for use in the treatment of cutaneous warts or genital warts In an embodiment of the invention the compounds of the invention are contemplated for use in the treatment of common warts, plantar warts and flat warts.

In an embodiment of the invention the compounds of the invention are contemplated for use in the treatment of lentigo maligna.

In an embodiment of the invention the compounds of the invention are contemplated for use in the treatment of cervical intraepithelial neoplasia, anal intraepithelial neoplasia or vulva intraepithelial neoplasia.

In an embodiment of the invention the compounds of the invention are contemplated for use in the treatment of acute myeloid leukemia.

In an embodiment the invention provides a method of treatment of cancer, actinic keratosis, seborrheic keratosis, viral infections, bacterial infections, wound healing, and treatment of photodamaged skin by administration to a subject in need thereof a compound of formula I.

In an embodiment the invention provides a method of treatment actinic keratosis by administration to a subject in need thereof a compound of formula I above.

In an embodiment the invention provides a method of treatment Seborrheic keratosis by administration to a subject in need thereof a compound of formula I above.

In an embodiment the invention provides a method of treatment photodamaged skin by administration to a subject in need thereof a compound of formula I above.

In an embodiment the invention provides a method of treatment of lesions caused by HPV infection by administration to a subject in need thereof a compound of formula I above.

In an embodiment the invention provides a method of treatment of common warts or genital warts by administration to a subject in need thereof a compound of formula I above.

In an embodiment the invention provides a method of treatment of cutaneous squamous cell carcinoma, mucosal squamous cell carcinoma or head and neck squamous cell carcinoma by administration to a subject in need thereof a compound of formula I above.

In an embodiment the invention provides a method of treatment of common warts, plantar warts and flat warts by administration to a subject in need thereof a compound of formula I above.

In an embodiment the invention provides a method of treatment of lentigo maligna by administration to a subject in need thereof a compound of formula I above.

In an embodiment the invention provides a method of treatment of cervical intraepithelial neoplasia, anal intraepithelial neoplasia or vulva intraepithelial neoplasia by administration to a subject in need thereof a compound of formula I above.

In an embodiment the invention provides a method of treatment of acute myeloid leukemia by administration to a subject in need thereof a compound of formula I above.

In an embodiment the invention provides use a compound according to formula I above in the manufacture of a pharmaceutical composition for the treatment or amelioration of a disease, disorder or condition responsive to stimulation of neutrophil oxidative burst.

In an embodiment the invention provides use of a compound according to formula I above in the manufacture of a pharmaceutical composition for the treatment or amelioration of a disease, disorder or condition responsive to stimulation of keratinocyte IL-8 release.

In an embodiment the invention provides use of a compound according to formula I above in the manufacture of a pharmaceutical composition for the treatment or amelioration of a disease, disorder or condition responsive to induction of necrosis.

In an embodiment the invention provides a method of preventing, treating, amelioration or prophylaxis of physiological disorders or diseases responsive to stimulation of neutrophil oxidative burst by administration to a subject in need thereof a compound according to formula I above.

In an embodiment the invention provides a method of preventing, treating, amelioration or prophylaxis of physiological disorders or diseases responsive to stimulation of keratinocyte IL-8 release by administration to a subject in need thereof a compound according to formula I above.

In an embodiment the invention provides a method of preventing, treating, amelioration or prophylaxis of physiological disorders or diseases responsive to responsive to induction of necrosis by administration to a subject in need thereof a compound according to formula I above.

In an embodiment the invention provides a compound according to formula I above for use in the treatment or amelioration of a disease, disorder or condition responsive to stimulation of neutrophil oxidative burst.

In an embodiment the invention provides a compound according to formula I above for use in the treatment or amelioration of a disease, disorder or condition responsive to stimulation of keratinocyte IL-8 release.

In an embodiment the invention provides a compound according to formula I above for use in the treatment or amelioration of a disease, disorder or condition responsive to induction of necrosis.

In an embodiment the invention provides a method of treatment of acute myeloid leukemia by administration to a subject in need thereof a compound of formula I above.

In an embodiment the invention provides a compound of formula I, for use in the treatment, prevention, amelioration or prophylaxis of physiological disorders or diseases associated with actinic keratosis, seborrheic keratosis, cancer, photodamaged skin or lesions caused by HPV infection.

In an embodiment the invention provides the use of a compound of formula I, for the manufacture of a medicament for the treatment, amelioration or prophylaxis of physiological disorders or diseases associated with actinic keratosis, Seborrheic keratosis, cancer, photodamaged skin or lesions caused by HPV infection.

In an embodiment the invention provides a method of preventing, treating, amelioration or prophylaxis of physiological disorders or diseases associated with actinic keratosis, Seborrheic keratosis, cancer, photodamaged skin or lesions caused by HPV infection by administration to a subject in need thereof a compound of formula I.

Pharmaceutical Compositions

For use in therapy, compounds of the present invention are typically in the form of a pharmaceutical composition. The invention therefore relates to a pharmaceutical composition comprising a compound of formula I, together with a pharmaceutically acceptable excipient or vehicle. The excipient must be "acceptable" in the sense of being compatible with the other ingredients of the composition and not deleterious to the recipient thereof.

Pharmaceutical compositions of the invention may be in unit dosage form such as tablets, pills, capsules, powders, granules, elixirs, syrups, emulsions, ampoules, suppositories or parenteral solutions or suspensions; for oral, parenteral, opthalmic, transdermal, intra-articular, topical, pulmonal, nasal, buccal or rectal administration or in any other manner appropriate for the formulation of compounds of the invention and in accordance with accepted practices such as those disclosed in *Remington: The Science and Practice of Pharmacy*, $21^{st}$ ed., 2000, Lippincott Williams & Wilkins.

For oral administration in the form of a tablet or capsule, a compound of formula I may suitably be combined with an oral, non-toxic, pharmaceutically acceptable carrier such as ethanol, glycerol, water or the like. Furthermore, suitable binders, lubricants, disintegrating agents, flavouring agents and colourants may be added to the mixture, as appropriate.

Suitable binders include, e.g., lactose, glucose, starch, gelatin, acacia gum, tragacanth gum, sodium alginate, carboxymethylcellulose, polyethylene glycol, waxes or the like. Lubricants include, e.g., sodium oleate, sodium stearate, magnesium stearate, sodium benzoate, sodium acetate, sodium chloride or the like. Disintegrating agents include, e.g., starch, methyl cellulose, agar, bentonite, xanthan gum or the like. Additional excipients for capsules include macrogols or lipids.

For the preparation of solid compositions such as tablets, the active compound of formula I is mixed with one or more excipients, such as the ones described above, and other pharmaceutical diluents such as water to make a solid preformulation composition containing a homogenous mixture of a compound of formula I. The term "homogenous" is understood to mean that the compound of formula I is dispersed evenly throughout the composition so that the composition may readily be subdivided into equally effective unit dosage forms such as tablets or capsules.

In the form of a dosage unit, the compound may be administered one or more times a day at appropriate intervals, always depending, however, on the condition of the patient, and in accordance with the prescription made by the medical practitioner. Conveniently, a dosage unit of a formulation contain between 0.01 and 200 mg, preferably between 0.01 mg and 20 mg, such as 0.01-5 mg of a compound of formula I.

A suitable dosage of the compound of the invention will depend, inter alia, on the age and condition of the patient, the severity of the disease to be treated and other factors well known to the practising physician. The compound may be administered either orally, parenterally or topically according to different dosing schedules, e.g. daily or with weekly intervals. In general a single dose will be in the range from 0.01 to 200 mg/kg body weight. The compound may be administered as a bolus (i.e. the entire daily dosis is administered at once) or in divided doses two or more times a day.

If the treatment involves administration of another therapeutically active compound it is recommended to consult Goodman & Gilman's *The Pharmacological Basis of Therapeutics*, 9$^{th}$ Ed., J. G. Hardman and L. E. Limbird (Eds.), McGraw-Hill 1995, for useful dosages of said compounds. The administration of a compound of the present invention with one or more other active compounds may be either concomitantly or sequentially.

Liquid formulations for either oral or parenteral administration of the compound of the invention include, e.g., aqueous solutions, syrups, aqueous or oil suspensions and emulsion with edible oils such as cottonseed oil, sesame oil, coconut oil or peanut oil. Suitable dispersing or suspending agents for aqueous suspensions include synthetic or natural gums such as tragacanth, alginate, acacia, dextran, sodium carboxymethylcellulose, gelatin, methylcellulose or polyvinylpyrolidone.

For parenteral administration, e.g. intramuscular, intraperitoneal, subcutaneous or intravenous injection or infusion, the pharmaceutical composition preferably comprises a compound of formula I dissolved or solubilised in an appropriate, pharmaceutically acceptable solvent. For parenteral administration, the composition of the invention may include a sterile aqueous or non-aqueous solvent, in particular water, isotonic saline, isotonic glucose solution, buffer solution or other solvent conventionally used for parenteral administration of therapeutically active substances. The composition may be sterilised by, for instance, filtration through a bacteria-retaining filter, addition of a sterilising agent to the composition, irradiation of the composition, or heating the composition. Alternatively, the compound of the invention may be provided as a sterile, solid preparation, e.g. a freeze-dried powder, which is dissolved in sterile solvent immediately prior to use. The composition intended for parenteral administration may additionally comprise conventional additives such as stabilisers, buffers or preservatives, e.g. antioxidants such as methyl hydroxybenzoate or the like.

Compositions for rectal administration may be in the form of a suppository incorporating the active ingredient and a carrier such as cocoa butter, or in the form of an enema. Compositions suitable for intra-articular administration may be in the form of a sterile aqueous preparation of the active ingredient which may be in microcrystalline form, for example, in the form of an aqueous microcrystalline suspension. Liposomal formulations or biodegradable polymer systems may also be used to present the active ingredient for both intra-articular and ophthalmic administration.

Compositions suitable for topical administration, including ophthalmic treatment, include liquid or semi-liquid preparations such as liniments, lotions, gels, applicants, oil-in-water or water-in-oil emulsions such as creams, ointments or pastes; or solutions or suspensions such as drops. Compositions for ophthalmic treatment may preferably additionally contain a cyclodextrin. Compositions suitable for administration to the nasal or buccal cavity or for inhalation include powder, self-propelling and spray formulations, such as aerosols and atomizers.

Human skin, in particular the outer layer, the stratum corneum, provides an effective barrier against penetration of microbial pathogens and toxic chemicals. While this property of skin is generally beneficial, it complicates the dermal administration of pharmaceuticals in that a large quantity, if not most, of the active ingredient applied on the skin of a patient suffering from a dermal disease may not penetrate into the viable layers of the skin where it exerts its activity.

Penetration of the skin is facilitated by addition of penetration enhancers which include isopropyl alcohol, sulphoxides, azones, pyrrolidines, alkanols, and glycols. In embodiments of the invention the penetrations enhancers includes DMSO, laurocapram, 2-pyrrolidone, decanol and propylene glycol. In an embodiment of the invention the penetration enhancer is isopropyl alcohol.

In embodiments of the invention the therapeutically active compound is dissolved in a suitable solvent. Suitable solvents are glycols, ketone, acetates and ethers. Ingenol compounds have been shown to have good stability in alcohols such as benzyl alcohol and isopropyl alcohol. In general, ingenol compounds have previously shown to have good stability at low pH. In embodiments of the present invention pH the pharmaceutical formulation is below 7. In embodiments of the present invention the pH of the pharmaceutical formulation is below 6. In embodiments of the present invention the pH of the pharmaceutical formulation is below 4.5. In embodiments of the present invention the pH of the pharmaceutical formulation is below 4.0. In embodiments of the present invention the pH of the pharmaceutical formulation is below 4.5 and no less than 2.5. In embodiments of the present invention the pH of the pharmaceutical formulation is below 4.0 and no less than 2.5. The preferred pH range can be obtained by including an appropriate buffer. In an embodiment of the invention the buffer is an acetate buffer. In embodiments of the invention a citrate buffer is used. In embodiments of the invention a mixed citrate-phosphate buffer is used.

In one embodiment, the composition is an ointment. According to the current FDA classification, an ointment is a semisolid dosage from which may contain water and volatile substances in an amount of up to 20% by weight and which contains more than 50% by weight of hydrocarbons, waxes or polyols in the vehicle. Thus, according to the invention, the ointment may be a water-in-oil composition in which case the nanosuspension may be added as such to the lipophilic components of the composition, such that the composition contains up to 10% by weight or, preferably, up to 5% by weight of the aqueous phase. Alternatively, the composition may be a non-aqueous ointment which contains less than about 2%, preferably less than 1%, of free water by weight of the composition.

The ointment carrier may suitably contain a paraffin selected from paraffins consisting of hydrocarbons with chain lengths from $C_{5-60}$ and mixtures thereof. A frequently used ointment carrier is petrolatum, or white soft paraffin, which is composed of hydrocarbons of different chain lengths, peaking at about $C_{40-44}$, or a mixture of petrolatum and liquid paraffin (consisting of hydrocarbons of different chain lengths peaking at $C_{28-40}$). While petrolatum provides occlusion of the treated skin surface, reducing transdermal loss of water and potentiating the therapeutic effect of the active ingredient in the composition, it tends to have a greasy and/or tacky feel which persists for quite some time after application, and it is not easily spreadable. It may therefore be preferred to employ paraffins consisting of hydrocarbons of a somewhat lower chain length, such as paraffins consisting of hydrocarbons with chain lengths peaking at $C_{14-16}$, $C_{18-22}$, $C_{20-22}$, $C_{20-26}$ or mixtures thereof. It has been found that such paraffins are more cosmetically acceptable in that they are less tacky and/or greasy on application and more easily spreadable. They are therefore expected to result in improved patient compliance. Suitable paraffins of this type are manufactured by Sonneborn and marketed under the trade name Sonnecone, e.g. Sonnecone CM, Sonnecone DM1, Sonnecone DM2 and Sonnecone HV. These paraffins are further disclosed and characterized in WO 08/141,078 which is incorporated herein by reference. (The hydrocarbon composition of the paraffins has been determined by gas chromatography.)

To impart a desired viscosity to the composition, it may suitably include a lipophilic viscosity-increasing ingredient such as a wax. The wax may be a mineral wax composed of a mixture of high molecular weight hydrocarbons, e.g. saturated $C_{35-70}$ alkanes, such as microcrystalline wax. Alternatively, the wax may be a vegetable or animal wax, e.g. esters of $C_{14-32}$ fatty acids and $C_{14-32}$ fatty alcohols, such as beeswax. The amount of viscosity-increasing ingredient may vary according to the viscosifying power of the ingredient, but may typically be in the range of about 1-20% by weight of the composition. When the viscosity-increasing ingredient is microcrystalline wax it is typically present in an amount in the range of about 5-15% by weight, e.g. about 10% by weight, of the composition.

To maintain good physical stability of the composition, in particular to avoid separation of the aqueous and lipid phases therein, it may be advantageous to include a water-in-oil emulsifier with an HLB value of 3-8. Examples of such emulsifiers are polyoxyethylene $C_{8-22}$ alkyl ethers, e.g. polyoxyethylene stearyl ether, polyoxyethylene cetyl ether, polyoxyethylene oleyl ether or polyoxyethylene lauryl ether. The amount of emulsifier is typically in the range of 2-10% w/w of the composition. In another embodiment, the composition is a cream which may comprise similar components to the ointment, but which is typically an oil-in-water-emulsion containing a substantial amount of water.

The composition may also comprise other components commonly used in dermal formulations, e.g. antioxidants (e.g. alpha-tocopherol), preservatives such as benzyl alcohol, sodium edetate, pigments, skin soothing agents, skin healing agents and skin conditioning agents such as urea, allantoin or bisabolol, cf. *CTFA Cosmetic Ingredients Handbook*, $2^{nd}$ Ed., 1992. In an embodiment of the invention the preservative is benzyl alcohol.

In an embodiment the composition is a gel. Suitable gelling agents include, water soluble cellulose derived polymers, such as hydroxyalkyl cellulose polymers. In embodiments of the invention the polymers are hydroxymethylcellulose, hydroxyethylcellulose, hydroxypropylcellulose and hydroxypropylmethylcellulose. Other gelling agents are celluloses such as carboxymethyl cellulose, methylhydroxyethyl cellulose and methyl cellulose, carbomer such as carbopol and carrageenans. In embodiments of the invention the gelling agent is cellulose derived. In embodiments of the invention the cellulose is a hydroxyalkylcellulose, such as hydroxyethylcellulose.

In an embodiment of the invention the composition comprises active compound, penetration enhancer, preservative, gelling agent and buffer at a pH of below 4 and not less than 2.5. For topical administration, the compound of formula I may typically be present in an amount of from 0.001 to 20% by weight of the composition, such as 0.01% to about 10%. In embodiments of the present invention the active compound is present in 0.05-1%. In an embodiment of the present invention the active compound is present in 0.01-0.5%. In an embodiment of the present invention the active compound is present in a concentration of around 0.1%. In an embodiment of the invention the composition comprises 0.005-0.1% active compound, 20-40% isopropyl alcohol, 0.5-10% benzyl alcohol, 0.5-5% hydroxylethyl cellulose and citrate buffer to 100%.

Formulation of ingenol derivatives in a gel for topical application has been described in WO07/068,963, which is incorporated by reference.

Methods of Preparation

The compounds of formula I may for example be prepared using the reactions and techniques outlined below together with methods known in the art of synthetic organic chemistry, or variations thereof as appreciated by those skilled in the art. Preferred methods include, but are not limited to, those described below. The reactions are carried out in solvents appropriate to the reagents and materials employed and suitable for the transformations being effected. Also, in the synthetic methods described below, it is to be understood that all proposed reaction conditions, including choice of solvent, reaction atmosphere, reaction temperature, duration of experiment and work-up procedures, are chosen to be conditions of standard for that reaction, which should be readily recognized by one skilled in the art. Not all compounds falling into a given class may be compatible with some of the reaction conditions required in some of the methods described. Such restrictions to the substituents which are compatible with the reaction conditions will be readily apparent to one skilled in the art and alternative methods can be used. The compounds of the present invention or any intermediate may be purified if required using standard methods well known to a synthetic organist chemist, e.g. methods described in W. Armarego "Purification of Laboratory Chemicals", Butterworth-Heinemann, $6^{th}$ ed. 2009. Starting materials are either known compounds, commercially available, or they may be prepared by routine synthetic methods well known to a person skilled in the art.

The compounds of the invention may for example be prepared according to the following non-limiting general methods and examples

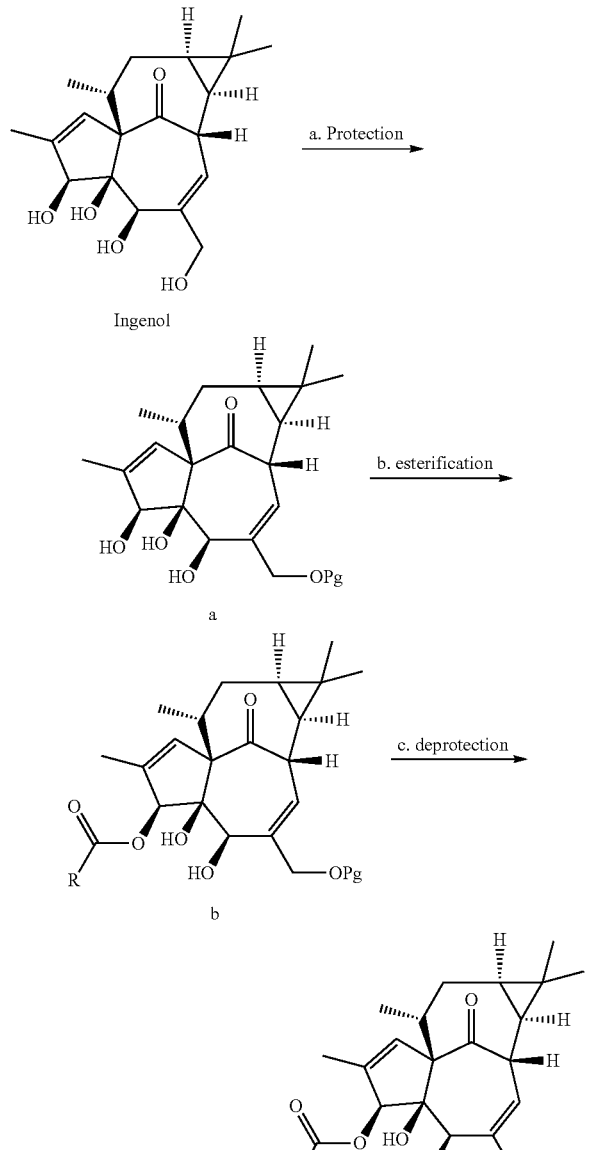

Scheme I

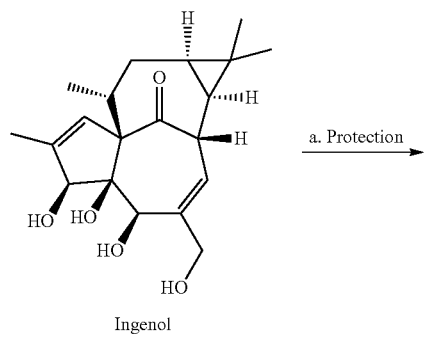

Scheme 2

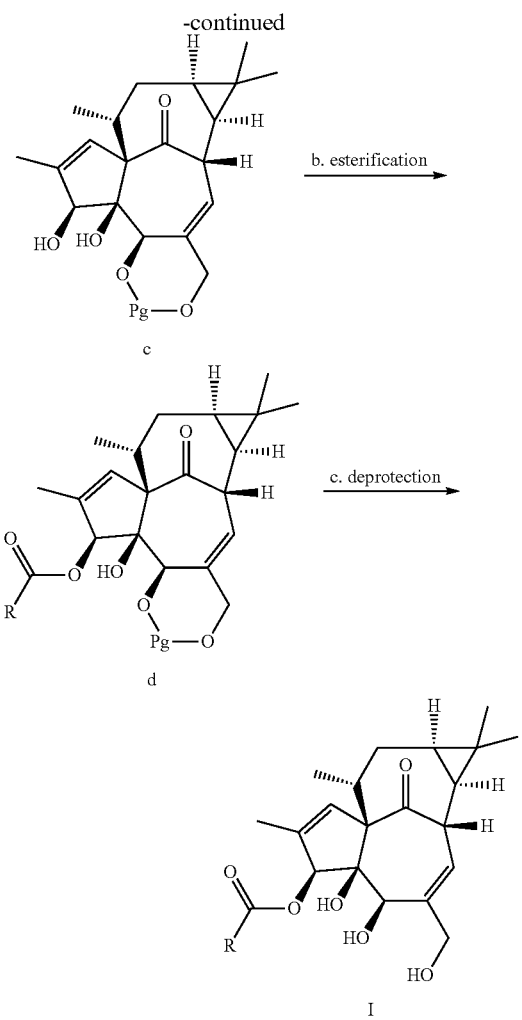

The compounds of the general formula I can for example be synthesised according to scheme 1 or 2 by reacting ingenol with a hydroxyl protecting agent or a dihydroxyl protecting agent to afford the protected ingenol derivatives a or c according to methods described in, but not limited to "Protective Groups in Organic Synthesis", 4th ed. P. G. M. Wuts; T. W. Greene, John Wiley, 2007 or in P. J. Kocienski, "Protecting Groups", 3rd ed. G. Thieme, 2003 and references cited therein.

For example compound a, wherein the protective group (Pg) is triphenylmethyl, can be synthesised by reacting ingenol with a triphenylmethyl reagent such as triphenylmethylpyridinium fluoroborate or triphenylmethyl chloride in a suitable solvent such as pyridine, N,N-dimethylformamide or dichloromethane in the presence or in the absence of base (e.g. Opferkuch et. al., Z. Naturforschung, (1981), 36B, 878).

Compound a, wherein the protective group (Pg) is silyl, can for example be synthesised by reacting ingenol with a silyl chloride such as tert-butyldimethylsilyl chloride, tert-butyldiphenylsilyl chloride or triisopropylsilyl chloride in a suitable solvent such as N,N-dimethylformamide, pyridine, dichloromethane, tetrahydrofuran or acetonitrile in the presence of a suitable base such as imidazole, triethylamine, N,N-diisopropylethylamine or 4-(N,N-dimethylamino)pyridine (e.g. Sorg, B. et. al, Z. Naturforsch., (1982), 37B, 1640-47), or by reacting compound (II) with a silyl triflate such as tert-butyldimethylsilyl trifluoromethanesulfonate in a suitable solvent such as dichloromethane in the presence of a suitable base such as triethylamine.

Compound a wherein Pg is 2-tetrahydropyranyl, can for example be synthesised by reacting ingenol with dihydropyran in a suitable solvent such as dichloromethane or acetonitrile in the presence of a suitable acid such as p-toluenesulfonic acid. Compound c wherein the protective group (Pg) represents an acetal such as benzylidene acetal can for example be prepared by reacting ingenol with benzaldehyde or benzaldehyde dimethyl acetal in a suitable solvent such as dichloromethane or N,N-dimethylformamide in the presence of a suitable acid such as p-toluenesulfonic acid. Compound c wherein the protective group (Pg) represents a ketal such as isopropylidene ketal can for example be synthesised by reacting ingenol with a ketone such as acetone or a dimethoxy ketal such as 2,2-dimethoxy propane in a suitable solvent such as dichloromethane or N,N-dimethylformamide in the presence of a suitable acid such as p-toluenesulfonic acid (e.g B. Sorg, Z. Naturforsch. (1982), 37b, 748-756). Acetone and 2,2-dimethoxy propane can also act as solvents.

As depicted in scheme 1 and 2 the protected ingenol derivatives a or c may be esterified to give compounds of the general formula b or d according to methods for esterification of hydroxyl groups described in, but not limited to "Esterification" by J. Otera, Wiley-VCH, 2003 and references cited therein. Compound b or d can for example be synthesised by reacting compound a or c with an activated acid derivative such as an acid halide such as acid chloride. The esterification by reaction with acid chloride can take place in a suitable solvent such as dichloromethane or toluene without an activator, or it can take place in the presence of a base such as pyridine, triethylamine or 4-(N, N-dimethylamino)pyridine (e.g. B. Sorg, Z. Naturforsch. (1982), 37b, 748-756). Compound b or d can for example be synthesised by reacting compound a or c with activated acid derivative such as an acid anhydride. The esterification by reaction with an acid anhydride can take place without a catalyst (e.g. Opferkuch et. al., Z. Naturforschung, (1981), 36B, 878), or in the presence of an acidic catalyst using an acid such as perchloric acid or a Lewis acid such as scandium (III) triflate or bismuth (III) triflate, or in the presence of a base such as sodium hydrogencarbonate or triethylamine.

Compound b or d can for example be synthesised by reacting compound a or c with an activated acid derivative such as a mixed anhydride of an acid such as trichlorobenzoic acid. The esterification by reaction with a mixed anhydride can take place in a suitable solvent without a catalyst, or in the presence of an acidic catalyst using an acid such as perchloric acid or a Lewis acid such as scandium (III) triflate or bismuth (III) triflate, or in the presence of a base such as sodium hydrogencarbonate or triethylamine.

Compound b or d can for example be synthesised by reacting compound a or c with an acid in the presence a coupling reagent such as a carbodiimide such as dicyclohexylcarbodiimide or N-(3-dimethylaminopropyl)-N'-ethylcarbodiimide with or without the presence of a base such as 4-(N,N-dimethylamino)pyridine and with or without catalysts such as 4-(N,N-dimethylamino)pyridine in a suitable solvent such as dichloromethane (e.g Appendino et. al., Eur. J. Org. Chem. (1999), 3413). Solid-supported coupling reagents can also be used in the esterification step [Nam, N.-H., Journal of Combinatorial Chemistry, (2003), 5, 479-545, or "Esterification" by J. Otera, Wiley-VCH, 2003].

Compound b or d can for example be synthesised by reacting compound a or c with an activated acid derivative such as a cyclic anhydride such as 3,1-benzoxazine-2,4(1H)-diose. The esterification by reaction with a cyclic anhydride can take place in a suitable solvent, such as acetonitrile, without a catalyst, or in the presence of a base such as 4-(N,N-dimethylamino)-pyridine, sodium hydrogencarbonate or triethylamine.

Compound b or d can be modified in the group R, before deprotection to a compound of the general formula I. An example of such a modification is the reductive alkylation of ingenol-5,20-acetonide-3-(2-amino-benzoate) to form N-alkyl substituted ingenol-5,20-acetonide-3-(2-amino-benzoate). The reductive alkylation can take place in a suitable solvent, such as dichloromethane in the presence of acetic acid and sodium-tri(acetoxy)-borohydride. The intermediate compounds b or d may be used in the subsequent deprotection reaction without purification to give compounds of the general formula I.

The compounds of formula I may be prepared by selective removal of the protective groups Pg from the compounds of the general structure b or d according to methods for deprotection of hydroxyl or dihydroxyl protective groups described, in but not limited to "Protective Groups in Organic Synthesis", 4th ed. P. G. M. Wuts; T. W. Greene, John Wiley, 2007 or in P. J. Kocienski, "Protecting Groups", 3rd ed. G. Thieme, 2003 and references cited therein.

Compounds of general formula I can for example be prepared from compounds of general formula d wherein Pg represents an acetal such as benzylidene acetal or a ketal such as an isopropyliden ketal by cleavage of the protecting group in the presence of a suitable acid such as aqueous hydrogen chloride, acetic acid, trifluoroacetic acid or p-toluenesulfonic acid in a suitable solvent such as methanol or aqueous tetrahydrofuran. Compounds of general formula I can for example be prepared from compounds of general formula b wherein Pg represents an alkoxyalkyl such as 2-tetrahydropyranyl by cleaving the acetal moiety, for example by acid catalysed cleavage in the presence of a suitable acid such as p-toluenesulfonic acid in a suitable solvent such as methanol. Compounds of general formula I can for example be prepared from compounds of general formula b wherein Pg represents silyl such as tert-butyldimethylsilyl by reacting compound b with a suitable acid such as hydrogen chloride in a suitable solvent such as methanol or by reacting with a fluoride source such as tetra n-butylammonium fluoride or tetrafluorosilane in a suitable solvent such as tetrahydrofuran or acetonitrile. Compounds of general formula I can for example be prepared from compounds of general formula b wherein Pg represents triphenylmethyl by reacting compound b with a suitable acid such as formic acid or trifluoroacetic acid in a suitable solvent such as ether, methanol or dichloromethane.

Compounds of formula b, d or I of scheme 1 or 2 above, can for example be synthesised enzymatic esterification by reacting compound a, c or ingenol with an acyl donor such as an acid anhydride, an ester such as vinyl ester or a thioester in the presence of an enzyme such as a lipase or an esterase.

EXAMPLES

General

All the starting materials used are commercially available, unless otherwise described. For $^1$H nuclear magnetic resonance (NMR) spectra, chemical shift values ($\delta$) (in ppm) are quoted; tetramethylsilane ($\delta$=0.00) is as standard. The value of a defined doublet (d), triplet (t), quartet (q)) or a range (m) is given. Chemical shifts of exchangeable protons (often broad singlets (bs)) are sometimes difficult to locate in the spectra. All organic solvents used were anhydrous, unless otherwise specified. Flash chromatography was performed on silica gel. Appropriate mixtures of ethyl acetate and heptane were used as eluents unless otherwise noted. Compounds were detected on TLC plates by development with aqueous potassium permanganate solution.

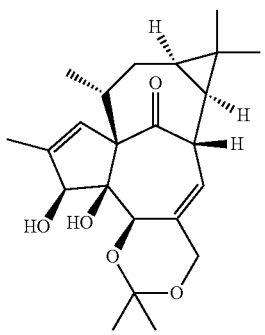

Ingenol-5,20-acetonide

Ingenol (1.00 g, 2.30 mmol) was dissolved in a solution of p-toluenesulphonic acid monohydrate in acetone (0.47 mg/mL, 22.5 mL). The solution was stirred at room temperature for 25 min. To this solution was added a saturated aqueous solution of NaHCO$_3$ (0.2 mL). The obtained mixture was concentrated in vacuo. The residue was taken up in brine and extracted with ethyl acetate. The combined organic phases were dried over sodium sulfate and concentrated in vacuo. The residue was purified by flash chromatography (heptane/ethyl acetate 19:1→heptane/ethyl acetate 0:1), giving the title compound as a white solid (616 mg, 69%). (See also: Opferkuch, H. J. et. al., Z. Naturforsch., (1981), 86b, 878-887.)

$^1$H NMR (300 MHz, CDCl$_3$) δ 5.91 (q, J=1.5 Hz, 1H), 5.79 (m, 1H), 4.25 (d, J=4.5 Hz, 1H), 4.20-4.07 (m, 3H), 3.93 (s, 1H), 3.51 (s, 1H), 2.57-2.41 (m, 2H), 2.25 (ddd, J=15.7, 8.4, 2.9 Hz, 1H), 1.85 (d, J=1.5 Hz, 3H), 1.77 (dt, J=15.8, 5.9 Hz, 1H), 1.41 (s, 3H), 1.35 (s, 3H), 1.13 (s, 3H), 1.05 (s, 3H), 1.00-0.87 (m, 4H), 0.70 (td, J=8.4, 6.4 Hz, 1H).

General Procedures for the Preparation of Compounds of General Formula II

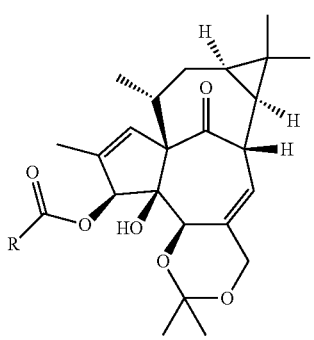

II

Procedure a

A mixture of carboxylic acid (0.100 mmol), dicyclohexylcarbodiimide (0.100 mmol), 4-(N,N-dimethylamino)-pyridine (0.0025 mmol) and ingenol-5,20-acetonide (0.050 mmol) were stirred at room temperature in dichloromethane for 20-24 h. The mixture was mixed with ethyl acetate, filtered and washed with saturated aqueous sodium chloride. The organic phase was dried with sodium sulphate, concentrated in vacuo and purified by flash chromatography (heptane→heptane/ethyl acetate 7:3), giving the title compound as a white solid.

Procedure b

A mixture of acyl chloride (0.0625 mmol), diisopropylethylamine (0.075 mmol), 4-(N,N-dimethylamino)-pyridine (0.070 mmol) and ingenol-5,20-acetonide (0.050 mmol) were stirred at 55° C. in tetrahydrofuran for 6-20 h. The mixture was mixed with ethyl acetate, filtered and washed with saturated aqueous sodium chloride. The organic phase was dried with sodium sulphate, concentrated in vacuo and purified by flash chromatography (heptane→heptane/ethyl acetate 7:3), giving the title compound as a white solid.

Procedure c

A mixture of carboxylic acid (0.100 mmol), dicyclohexylcarbodiimide (0.100 mmol), 4-(N,N-dimethylamino)-pyridine (0.025 mmol) and ingenol-5,20-acetonide (0.050 mmol) were stirred in a microwave oven at 150° C. in acetonitrile for 5 min. The mixture was mixed with ethyl acetate, filtered and washed with saturated aqueous sodium chloride. The organic phase was dried with sodium sulphate, concentrated in vacuo and purified by flash chromatography (heptane→heptane/ethyl acetate 7:3), giving the title compound as a white solid.

Procedure d

A mixture of acyl chloride (0.125 mmol), diisopropylethylamine (0.250 mmol), 4-(N,N-dimethylamino)-pyridine (0.025 mmol) and ingenol-5,20-acetonide (0.050 mmol) were stirred in a microwave oven at 150° C. in acetonitrile for 20 min. The mixture was mixed with ethyl acetate, filtered and washed with saturated aqueous sodium chloride. The organic phase was dried with sodium sulphate, concentrated in vacuo and purified by flash chromatography (heptane→heptane/ethyl acetate 7:3), giving the title compound as a white solid.

Procedure f

A mixture of ingenol-5,20-acetonide (0.10 mmol), 3,1-benzoxazine-2,4(1H)-dione (0.25 mmol) and 4-(N,N-dimethylamino)-pyridine (0.05 mmol) in acetonitrile were stirred in a microwave reactor at 160° C. for 8 min. The mixture was filtrated, rinsed with 1 ml of dichloromethane and the filtrate was concentrated in vacuo. The residue was purified by flash chromatography (heptane→heptane/ethyl acetate 7:3), to afford the title compound.

General Procedure for the Preparation of Compounds of General Formula I

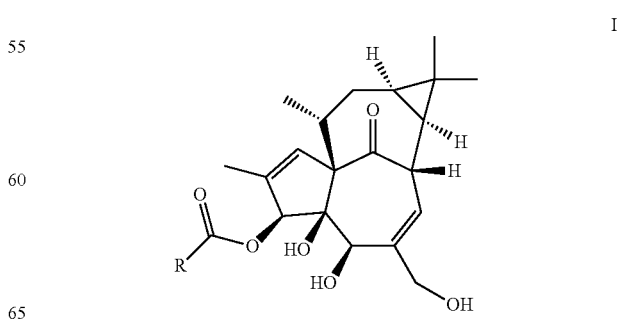

I

Procedure e

Ingenol-5,20-acetonide-3-acylate (0.10 mmol) was dissolved in tetrahydrofuran (0.47 mL) under argon. An aqueous solution of HCl (4 M, 4.7 µL) was added. The solution was stirred at room temperature for 20-27 h. The solution was concentrated in vacuo. The residue was purified by flash chromatography (heptane/ethyl acetate 5:1→heptane/ethyl acetate 3:7), giving the title compound.

Procedure g

A mixture of ingenol-5,20-acetonide-3-(2-amino-benzoate) (0.02 mmol), an aldehyde (0.03 mmol), acetic acid (0.03 mmol) and sodium-tri(acetoxy)-borohydride (0.03 mmol) in dichloromethane was stirred at room temperature for 1 hour. The mixture was concentrated in vacuo, and tetrahydrofuran (300 µL) followed by an aqueous solution of HCl (4 M, 30 µL) was added. The mixture was stirred at room temperature for 16 h. Heptane (300 µL) was added and the crude product was purified by flash chromatography (heptane→heptane/ethyl acetate 7:3), to afford the title compound.

Procedure h

A mixture of ingenol-5,20-acetonide-3-(2-amino-6-methyl-benzoate) (0.038) mmol), acid chloride (0.058 mmol) and potassium carbonate (0.076 mmol) in acetonitrile was stirred at room temperature for 3 hours. 2 drops of water and dichloromethane (1 mL) was added and the mixture was filtered and concentrated in vacuo. The residue was purified by flash chromatography (heptane→heptane/ethyl acetate 6:4), giving the title compound as a white solid.

Procedure for the Preparation of 1-methyl-3,1-benzoxazine-2,4(1H)-dione

Procedure i

A mixture of 3,1-benzoxazine-2,4(1H)-dione (0.25 mmol) and potassium carbonate (0.30 mmol) in dimethylformamide was cooled down to 0° C. on an ice bath. Dimethylsulfat (0.33 mmol) was added drop wise and the mixture was stirred for 2 h at 0° C. 2 drops of water and 1 ml of dichloromethane was added and the mixture was filtered and concentrated in vacuo, to give 1-methyl-3,1-benzoxazine-2,4(1H)-dione.

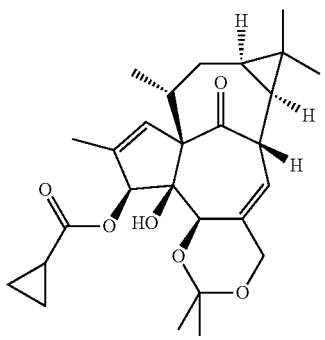 [SMILES: CC1=C[C@]23C(=O)[C@@H](C=C4COC(C)(C)O[C@H]4[C@]2(O)[C@H]1OC(=O)C1CC1)[C@H]1[C@@H](C[C@H]3C)C1(C)C]

Preparation 401

Ingenol-5,20-acetonide-3-(cyclopropanecarboxylate) (Compound 401)

Compound 401 was prepared according to Procedure a.
Starting material: Cyclopropanecarboxylic acid.
$^1$H NMR (300 MHz, CDCl$_3$) δ 6.04-6.03 (m, 1H), 5.78-5.76 (m, 1H), 5.55 (s, 1H), 4.23-4.10 (m, 3H), 3.99 (s, 1H), 3.14 (s, 1H), 2.60-2.55 (m, 1H), 2.33-2.23 (m, 1H), 1.82-1.61 (m, 5H), 1.44 (s, 3H), 1.39 (s, 3H), 1.10 (s, 3H), 1.05 (s, 3H), 1.04-0.85 (m, 5H), 0.99 (d, 3H), 0.73-0.66 m, 1H).

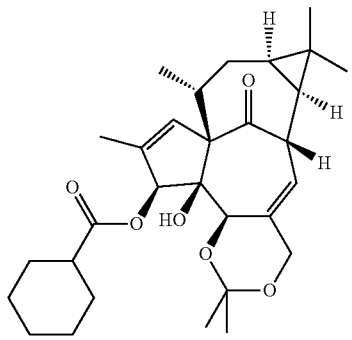 [SMILES: CC1=C[C@]23C(=O)[C@@H](C=C4COC(C)(C)O[C@H]4[C@]2(O)[C@H]1OC(=O)C1CCCCC1)[C@H]1[C@@H](C[C@H]3C)C1(C)C]

Preparation 402

Ingenol-5,20-acetonide-3-(cyclohexanecarboxylate) (Compound 402)

Compound 402 was prepared according to Procedure a.
Starting material: Cyclohexanecarboxylic acid.
$^1$H NMR (300 MHz, CDCl$_3$) δ 6.04-6.03 (m, 1H), 5.78-5.75 (m, 1H), 5.54 (s, 1H), 4.23-4.10 (m, 3H), 3.99 (s, 1H), 3.09 (s, 1H), 2.61-2.52 (m, 1H), 2.42-2.22 (m, 2H), 1.96-1.89 (m, 2H), 1.80-1.61 (m, 7H), 1.45 (s, 3H), 1.40 (s, 3H), 1.53-1.21 (m, 5H), 1.09 (s, 3H), 1.05 (s, 3H), 0.98 (d, 3H), 0.93-0.87 (m, 1H), 0.73-0.65 (m, 1H).

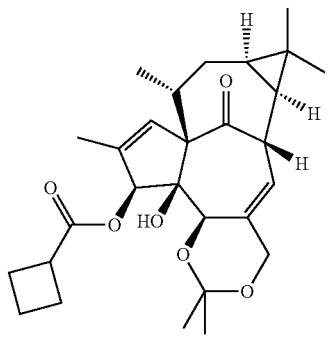 [SMILES: CC1=C[C@]23C(=O)[C@@H](C=C4COC(C)(C)O[C@H]4[C@]2(O)[C@H]1OC(=O)C1CCC1)[C@H]1[C@@H](C[C@H]3C)C1(C)C]

Preparation 403

Ingenol-5,20-acetonide-3-(cyclobutanecarboxylate) (Compound 403)

Compound 403 was prepared according to Procedure a.
Starting material: Cyclobutanecarboxylic acid.

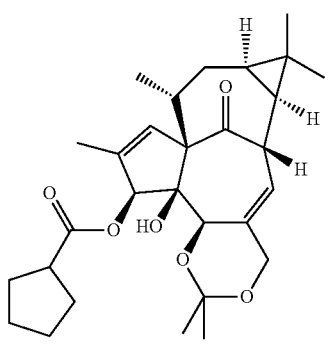 [SMILES: CC1=C[C@]23C(=O)[C@@H](C=C4COC(C)(C)O[C@H]4[C@]2(O)[C@H]1OC(=O)C1CCCC1)[C@H]1[C@@H](C[C@H]3C)C1(C)C]

Preparation 404

Ingenol-5,20-acetonide-3-(cyclopentanecarboxylate) (Compound 404)

Compound 404 was prepared according to Procedure a.
Starting material: Cyclopentanecarboxylic acid.

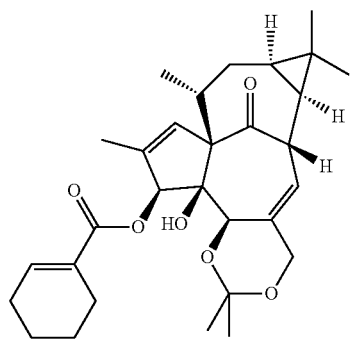 [SMILES: CC1=C[C@]23C(=O)[C@@H](C=C4COC(C)(C)O[C@H]4[C@]2(O)[C@H]1OC(=O)C1=CCCCC1)[C@H]1[C@@H](C[C@H]3C)C1(C)C]

Preparation 405

Ingenol-5,20-acetonide-3-(cyclohexene-1-carboxylate) (Compound 405)

Compound 405 was prepared according to Procedure a.
Starting material: Cyclohexene-1-carboxylic acid.
$^1$H NMR (300 MHz, CDCl$_3$) δ 7.00-6.98 (m, 1H), 6.04-6.03 (m, 1H), 5.78-5.76 (m, 1H), 5.62 (s, 1H), 4.23-4.11 (m, 3H), 4.01 (s, 1H), 3.19 (s, 1H), 2.60-2.55 (m, 1H), 2.31-2.21 (m, 5H), 1.82-1.60 (m, 8H), 1.45 (s, 3H), 1.41 (s, 3H), 1.09 (s, 3H), 1.05 (s, 3H), 1.00 (d, 3H), 0.94-0.88 (m, 1H), 0.73-0.65 (m, 1H).

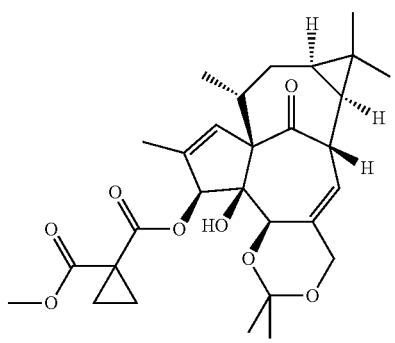

Preparation 406

Ingenol-5,20-acetonide-3-(1-methoxycarbonyl-cyclopropylcarboxylate) (Compound 406)

Compound 406 was prepared according to Procedure a.
Starting material: 1-Methoxycarbonyl-cyclopropanecarboxylic acid.

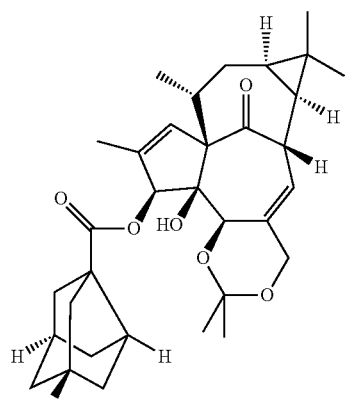

Preparation 407

Ingenol-5,20-acetonide-3-(noradamantane-3-carboxylate) (Compound 407)

Compound 407 was prepared according to Procedure b.
Starting material: Noradamantane-3-carboxylic acid chloride.

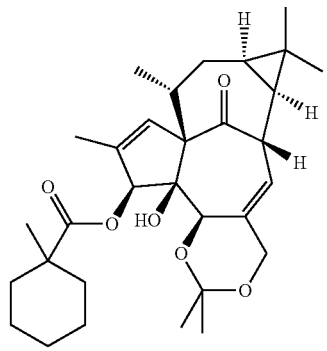 [SMILES: CC1=C[C@]23C(=O)[C@@H](C=C4COC(C)(C)O[C@H]4[C@]2(O)[C@H]1OC(=O)C1(C)CCCCC1)[C@H]1[C@@H](C[C@H]3C)C1(C)C]

Preparation 408

Ingenol-5,20-acetonide-3-(1-methyl-cyclohexanecarboxylate) (Compound 408)

Compound 408 was prepared according to Procedure b.
Starting material: 1-Methyl-cyclohexanecarboxylic acid chloride.
$^1$H NMR (300 MHz, CDCl$_3$) δ 6.04-6.03 (m, 1H), 5.78-5.76 (m, 1H), 5.57 (s, 1H), 4.24-4.10 (m, 3H), 4.01 (s, 1H), 3.09 (s, 1H), 2.61-2.54 (m, 1H), 2.31-2.22 (m, 1H), 2.09-2.00 (m, 2H), 1.78-1.69 (m 4H), 1.60-1.20 (m, 8H), 1.45 (s, 3H), 1.41 (s, 3H), 1.19 (s, 3H), 1.09 (s, 3H), 1.04 (s, 3H), 0.98 (d, 3H), 0.93-0.86 (m, 1H), 0.73-0.65 (m, 1H).

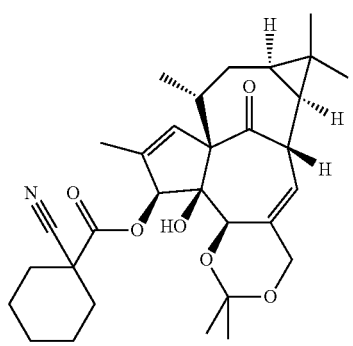 [SMILES: CC1=C[C@]23C(=O)[C@@H](C=C4COC(C)(C)O[C@H]4[C@]2(O)[C@H]1OC(=O)C1(C#N)CCCCC1)[C@H]1[C@@H](C[C@H]3C)C1(C)C]

Preparation 409

Ingenol-5,20-acetonide-3-(1-cyano-cyclohexanecarboxylate) (Compound 409)

Compound 409 was prepared according to Procedure c.
Starting material: 1-Cyano-cyclohexanecarboxylic acid.
$^1$H NMR (300 MHz, CDCl$_3$) δ 6.12 (m, 1H), 5.80-5.78 (m, 1H), 5.55 (s, 1H), 4.25-4.09 (m, 1H), 4.01 (s, 1H), 3.09 (s, 1H), 2.65-2.60 (m, 1H), 2.30-2.10 (m, 3H), 1.88-1.60 (m, 12H), 1.45 (s, 3H), 1.42 (s, 3H), 1.31-1.21 (m, 2H), 1.09 (s, 3H), 1.05 (s, 3H), 1.00 (d, 3H), 0.93-0.85 (m, 1H), 0.74-0.65 (m, 1H).

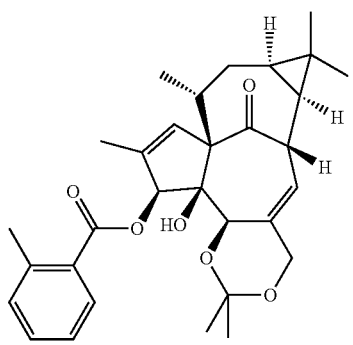 [SMILES: CC1=C[C@]23C(=O)[C@@H](C=C4COC(C)(C)O[C@H]4[C@]2(O)[C@H]1OC(=O)c1ccccc1C)[C@H]1[C@@H](C[C@H]3C)C1(C)C]

Preparation 410

Ingenol-5,20-acetonide-3-(2-methyl-benzoate) (Compound 410)

Compound 410 was prepared according to Procedure a.
Starting material: 2-Methyl-benzoic acid.

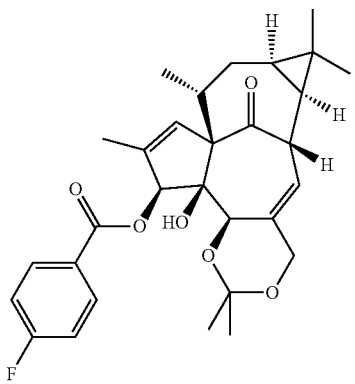 [SMILES: CC1=C[C@]23C(=O)[C@@H](C=C4COC(C)(C)O[C@H]4[C@]2(O)[C@H]1OC(=O)c1ccc(F)cc1)[C@H]1[C@@H](C[C@H]3C)C1(C)C]

Preparation 411

Ingenol-5,20-acetonide-3-(4-fluoro-benzoate) (Compound 411)

Compound 411 was prepared according to Procedure a.
Starting material: 4-Fluoro-benzoic acid.
$^1$H NMR (300 MHz, CDCl$_3$) δ 8.08-8.01 (m, 2H), 7.17-7.09 (m, 2H), 6.11-6.13 (m, 1H), 5.81-5.79 (m, 1H), 5.77 (s, 1H), 4.27-4.08 (m, 4H), 3.23 (s, 1H), 2.69-2.61 (m, 1H), 2.31-2.17 (m, 1H), 1.82-1.73 (m, 4H), 1.49 (s, 3H), 1.45 (s, 3H), 1.07 (s, 3H), 1.05 (d, 3H), 1.05 (s, 3H), 0.95-0.88 (m, 1H), 0.74-0.65 (m, 1H).

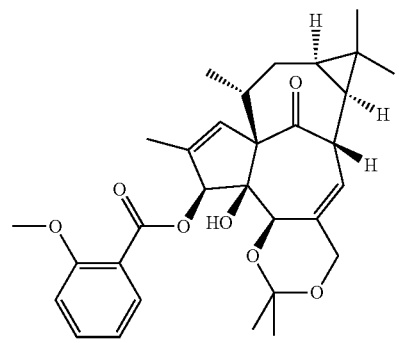

Preparation 412

Ingenol-5,20-acetonide-3-(2-methoxy-benzoate) (Compound 412)

Compound 412 was prepared according to Procedure a.
Starting material: 2-Methoxy-benzoic acid.

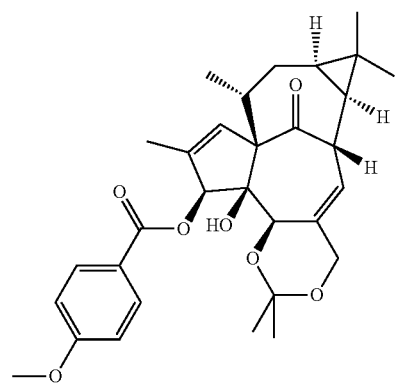

Preparation 413

Ingenol-5,20-acetonide-3-(4-methoxy-benzoate) (Compound 413)

Compound 413 was prepared according to Procedure a.
Starting material: 4-Methoxy-benzoic acid.

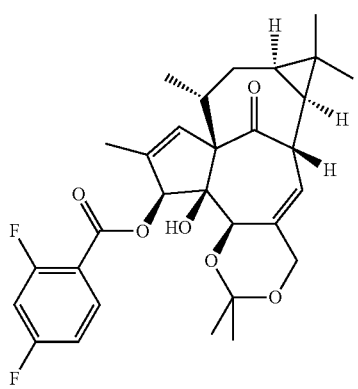 [SMILES: CC1=C[C@]23C(=O)[C@@H](C=C4COC(C)(C)O[C@H]4[C@]2(O)[C@H]1OC(=O)c1ccc(F)cc1F)[C@H]1[C@@H](C[C@H]3C)C1(C)C]

Preparation 414

Ingenol-5,20-acetonide-3-(2,4-difluoro-benzoate) (Compound 414)

Compound 414 was prepared according to procedure a. Starting material: 2,4-Difluoro-benzoic acid.

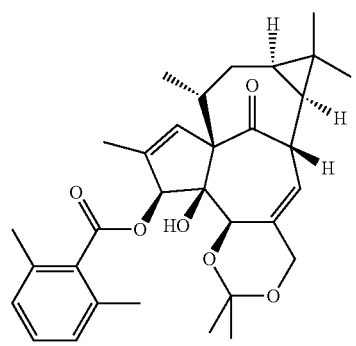 [SMILES: CC1=C[C@]23C(=O)[C@@H](C=C4COC(C)(C)O[C@H]4[C@]2(O)[C@H]1OC(=O)c1c(C)cccc1C)[C@H]1[C@@H](C[C@H]3C)C1(C)C]

Preparation 415

Ingenol-5,20-acetonide-3-(2,6-dimethyl-benzoate) (Compound 415)

Compound 415 was prepared according to Procedure d. Starting material: 2,6-Dimethyl-benzoyl chloride.
$^1$H NMR (300 MHz, CDCl$_3$) δ 7.22-7.17 (m, 1H), 7.05-7.02 (d, 2H), 6.09 (s, 1H), 5.82-5.81 (m, 2H), 4.28-4.09 (m, 4H), 3.39 (s, 1H), 2.57-2.51 (m, 1H), 2.36 (s, 6H), 2.32-2.21 (m, 1H), 1.84 (d, 3H), 1.75-1.66 (m, 1H), 1.50 (s, 3H), 1.48 (s, 3H), 1.09 (s, 3H), 1.05 (s, 3H), 0.92 (d, 3H), 0.90-0.85 (m, 1H), 0.72-0.64 (m, 1H).

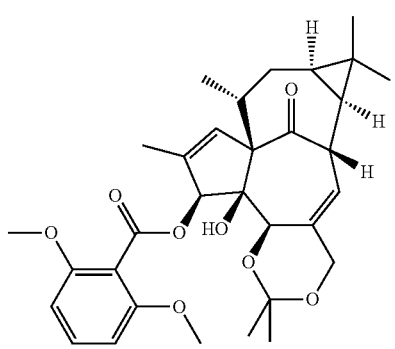

Preparation 416

Ingenol-5,20-acetonide-3-(2,6-dimethoxy-benzoate) (Compound 416)

Compound 416 was prepared according to Procedure d. Starting material: 2,6-Methoxy-benzoyl chloride.
$^1$H NMR (300 MHz, CDCl$_3$) δ 7.34 (t, 1H), 6.60 (d, 2H), 6.11 (s, 1H), 6.04-6.04 (m, 1H), 5.76-5.74 (m, 1H), 4.32-4.09 (m, 4H), 3.99 (s, 1H), 3.85 (s, 6H), 2.53-2.44 (m, 1H), 2.31-2.22 (m, 1H), 2.82 (d, 3H), 1.80-1.71 (m, 1H), 1.45 (s, 3H), 1.40 (s, 3H), 1.13 (s, 3H), 1.05 (s, 3H), 0.99-0.89 (m, 4H), 0.74-0.66 (m, 1H).

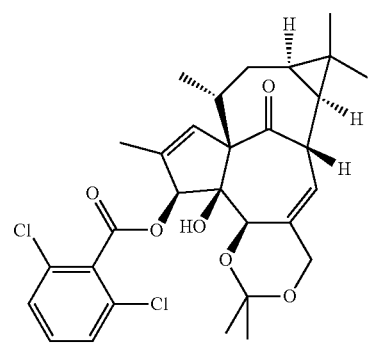 [SMILES: CC1=C[C@]23C(=O)[C@@H](C=C4COC(C)(C)O[C@H]4[C@]2(O)[C@H]1OC(=O)c1c(Cl)cccc1Cl)[C@H]1[C@@H](C[C@H]3C)C1(C)C]

Preparation 417

Ingenol-5,20-acetonide-3-(2,6-dichloro-benzoate) (Compound 417)

Compound 417 was prepared according to Procedure d. Starting material: 2,6-Dichloro-benzoyl chloride.
$^1$H NMR (300 MHz, CDCl$_3$) δ 7.36-7.26 (m, 3H), 6.09 (m, 1H), 5.84 (s, 1H), 5.81-5.80 (m, 1H), 4.27-4.14 (m, 3H), 4.05 (s, 1H), 3.34 (s, 1H), 2.61-2.55 (m, 1H), 2.30-2.21 (m, 1H), 1.87 (d, 3H), 1.77-1.69 (m, 1H), 1.49 (s, 3H), 1.47 (s, 3H), 1.10 (s, 3H), 1.04 (s, 3H), 0.95-0.85 (m, 4H), 0.72-0.64 (m, 1H).

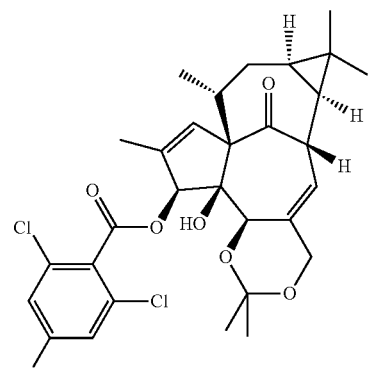

Preparation 418

Ingenol-5,20-acetonide-3-(2,4,6-trichloro-benzoate) (Compound 418)

Compound 418 was prepared according to Procedure d. Starting material: 2,4,6-Trichloro-benzoyl chloride.

¹H NMR (300 MHz, CDCl₃) δ 7.36 (s, 2H), 6.10-6.09 (m, 1H), 5.90 (m, 2H), 4.27-4.15 (m, 3H), 4.05 (s, 1H), 3.30 (s, 1H), 2.58-2.53 (m, 1H), 2.30-2.20 (m, 1H), 1.85 (d, 3H), 1.77-1.68 (m, 1H), 1.49 (s, 3H), 1.46 (s, 3H), 1.10 (s, 3H), 1.04 (s, 3H), 0.94-0.85 (m, 4H), 0.72-0.64 (m, 1H).

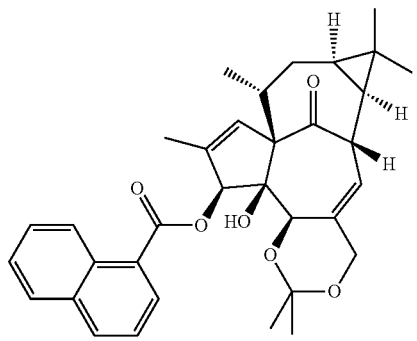 [SMILES: CC1=C[C@]23C(=O)[C@@H](C=C4COC(C)(C)O[C@H]4[C@]2(O)[C@H]1OC(=O)c1cccc2ccccc12)[C@H]1[C@@H](C[C@H]3C)C1(C)C]

Preparation 419

Ingenol-5,20-acetonide-3-(naphthalene-1-carboxylate) (Compound 419)

Compound 419 was prepared according to Procedure c.
Starting material: Naphthalene-1-carboxylic acid.

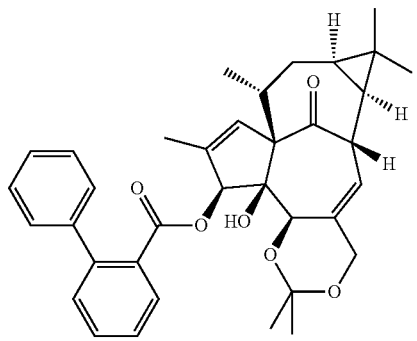 [SMILES: CC1=C[C@]23C(=O)[C@@H](C=C4COC(C)(C)O[C@H]4[C@]2(O)[C@H]1OC(=O)c1ccccc1-c1ccccc1)[C@H]1[C@@H](C[C@H]3C)C1(C)C]

Preparation 420

Ingenol-5,20-acetonide-3-(2-phenyl-benzoate) (Compound 420)

Compound 420 was prepared according to Procedure c.
Starting material: 2-Phenyl-benzoic acid.

¹H NMR (300 MHz, CDCl₃) δ 7.82 (dd, 1H), 7.53 (dt, 1H), 7.45-7.31 (m, 7H), 5.95 (m, 1H), 5.76-5.74 (m, 1H), 5.65 (s, 1H), 4.21-4.09 (m, 3H), 3.95 (s, 1H), 2.96 (s, 1H), 2.32-2.27 (m, 1H), 2.23-2.13 (m, 1H), 1.72-1.64 (m, 4H), 1.41 (s, 3H), 1.39 (s, 3H), 1.09 (s, 3H), 1.04 (s, 3H), 0.91-0.84 (m, 4H), 0.70-0.62 (m, 1H).

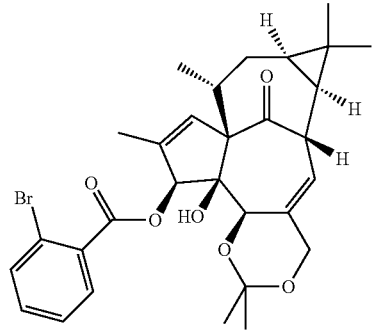 [SMILES: CC1=C[C@]23C(=O)[C@@H](C=C4COC(C)(C)O[C@H]4[C@]2(O)[C@H]1OC(=O)c1ccccc1Br)[C@H]1[C@@H](C[C@H]3C)C1(C)C]

Preparation 421

Ingenol-5,20-acetonide-3-(2-bromo-benzoate) (Compound 421)

Compound 421 was prepared according to Procedure b, but with the following changes:
Solvent: Dichloromethane; temperature: 45° C. (closed vial); time: 3 h.
Starting material: 2-Bromo-benzoyl chloride.

¹H NMR (300 MHz, CDCl₃) δ 7.81-7-78 (m, 1H), 7.68-7.65 (m, 1H), 7.42-7.31 (m, 2H), 6.11-6.10 (m, 1H), 5.84 (s, 1H), 5.82-5.80 (m, 1H), 4.27-4.13 (m, 3H), 4.07 (s, 1H), 3.33 (s, 1H), 2.69-2.64 (m, 1H), 2.34-2.24 (m, 1H), 1.85 (d, 3H), 1.82-1.73 (m, 1H), 1.49 (s, 3H), 1.47 (s, 3H), 1.10 (s, 3H), 1.05 (s, 3H), 0.98 (d, 3H), 0.95-0.85 (m, 1H), 0.74-0.66 (m, 1H).

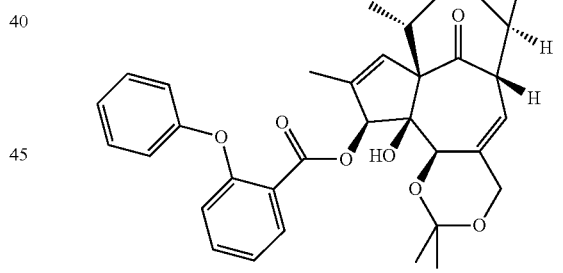

Preparation 422

Ingenol-5,20-acetonide-3-(2-phenoxy-benzoate) (Compound 422)

Compound 422 was prepared according to Procedure c.
Starting material: 2-Phenoxy-benzoic acid.

¹H NMR (300 MHz, CDCl₃) δ 8.00 (dd, 1H), 7.45-7.33 (m, 3H), 7.20-7.13 (m, 2H), 7.07-7.03 (m, 2H), 6.85-6.82 (d, 1H), 6.03 (m, 1H), 5.91 (s, 1H), 5.73-5.71 (m, 1H), 4.24-3.99 (m, 4H), 3.92 (s, 1H), 2.46-2.39 (m, 1H), 1.91-1.85 (m, 1H), 1.80 (d, 3H), 1.45 (s, 3H), 1.40 (s, 3H), 1.30-1.23 (m, 1H), 1.00 (s, 3H), 0.95 (s, 3H), 0.88-0.80 (m, 4H), 0.60-0.52 (m, 1H).

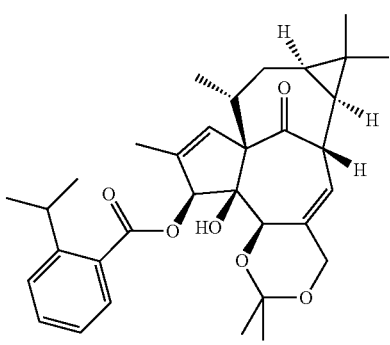 [SMILES: CC1=C[C@]23C(=O)[C@@H](C=C4COC(C)(C)O[C@H]4[C@]2(O)[C@H]1OC(=O)c1ccccc1C(C)C)[C@H]1[C@@H](C[C@H]3C)C1(C)C]

Preparation 423

Ingenol-5,20-acetonide-3-(2-isopropyl-benzoate) (Compound 423)

Compound 423 was prepared according to Procedure c.
Starting material: 2-Isopropyl-benzoic acid.

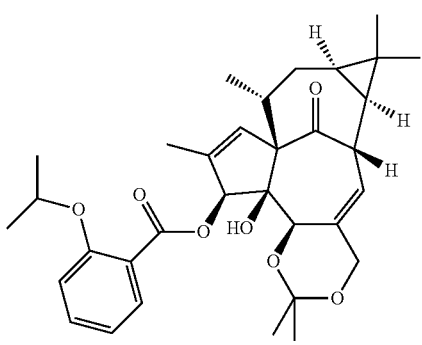 [SMILES: CC1=C[C@]23C(=O)[C@@H](C=C4COC(C)(C)O[C@H]4[C@]2(O)[C@H]1OC(=O)c1ccccc1OC(C)C)[C@H]1[C@@H](C[C@H]3C)C1(C)C]

Preparation 424

Ingenol-5,20-acetonide-3-(2-isopropoxy-benzoate) (Compound 424)

Compound 424 was prepared according to Procedure c.
Starting material: 2-Isopropoxy-benzoic acid.

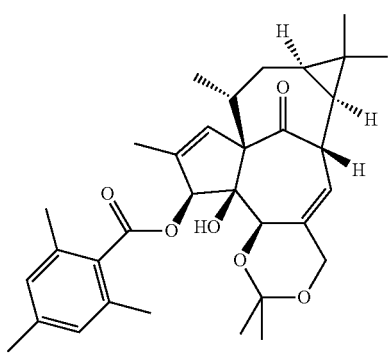

Preparation 425

Ingenol-5,20-acetonide-3-(2,4,6-trimethyl-benzoate) (Compound 425)

Compound 425 was prepared according to Procedure d.
Starting material: 2,4,6-Trimethyl-benzoyl chloride.
$^1$H NMR (300 MHz, CDCl$_3$) δ 6.86 (s, 2H), 6.07 (m, 1H), 5.80 (m, 2H), 4.27-4.08 (m, 4H), 3.37 (s, 1H), 2.57-2.52 (m, 1H), 2.33 (s, 6H), 2.29 (s, 3H), 2.30-2.20 (m, 1H), 1.83 (d, 3H), 1.74-1.64 (m, 1H), 1.50 (s, 3H), 1.47 (s, 3H), 1.09 (s, 3H), 1.04 (s, 3H), 0.93-0.85 (m, 4H), 0.71-0.63 (m, 1H).

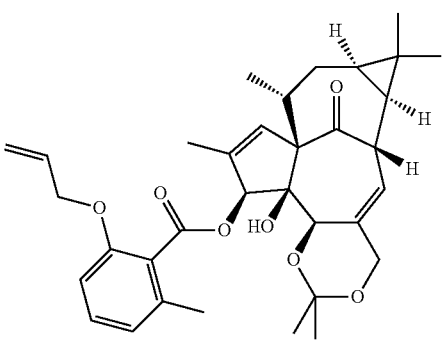 [SMILES: C=CCOc1cccc(C)c1C(=O)O[C@H]1C(C)=C[C@]23C(=O)[C@@H](C=C4COC(C)(C)O[C@H]4[C@]12O)[C@H]1[C@@H](C[C@H]3C)C1(C)C]

Preparation 426

Ingenol-5,20-acetonide-3-(2-allyloxy-6-methyl-benzoate) (Compound 426)

Compound 426 was prepared according to Procedure d, but using microwave oven at 100° C. in chloroform for 60 min.
Starting material: 2-Allyloxy-6-methyl-benzoyl chloride, prepared from 2-allyloxy-6-methyl-benzoic acid by reflux in an excess of thionyl chloride for 1 h followed by evaporation of solvent and volatiles in vacuo.

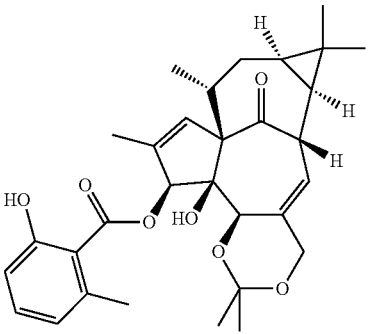

Preparation 427

Ingenol-5,20-acetonide-3-(2-hydroxy-6-methyl-benzoate) (Compound 427)

Diethylamine (0.1 ml) was added to a degassed solution of Compound 426 (260 mg) and tetrakis(triphenylphosphine)palladium(0) (20 mg) in dioxane (5 ml). After stirring for 1 h at rt. the mixture was concentrated and purified by chromatography as described in Procedure a-d.

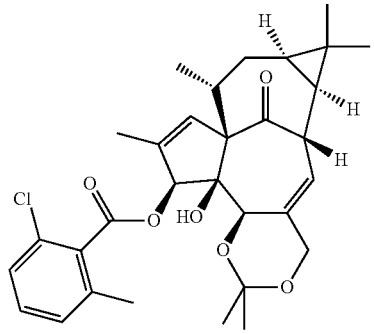 [SMILES: CC1=C[C@]23C(=O)[C@@H](C=C4COC(C)(C)O[C@H]4[C@]2(O)[C@H]1OC(=O)c1c(C)cccc1Cl)[C@H]1[C@@H](C[C@H]3C)C1(C)C]

Preparation 428

Ingenol-5,20-acetonide-3-(2-chloro-6-methyl-benzoate) (Compound 428)

Compound 428 was prepared according to Procedure d, with the following change: Time: 40 min.
Starting material: 2-Chloro-6-methyl-benzoyl chloride.
$^1$H NMR (300 MHz, CDCl$_3$) δ 7.24-7.19 (m, 2H), 7.15-7.10 (m, 1H), 6.08 (m, 1H), 5.82-5.80 (m, 2H), 4.27-4.08 (m, 4H), 3.41 (s, 1H), 2.57-2.52 (m, 1H), 2.40 (s, 3H), 2.32-2.21 (m, 1H), 1.86 (d, 3H), 1.76-1.67 (m, 1H), 1.50 (s, 3H), 1.47 (s, 3H), 1.10 (s, 3H), 1.05 (s, 3H), 0.94-0.86 (m, 4H), 0.72-0.64 (m, 1H).

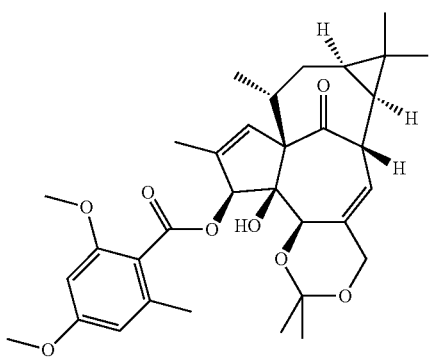

Preparation 429

Ingenol-5,20-acetonide-3-(2,4-dimethoxy-6-methyl-benzoate) (Compound 429)

Compound 429 was prepared according to Procedure d, with the following change: Time: 40 min.
Starting material: 2,4-Dimethoxy-6-methyl-benzoyl chloride.
$^1$H NMR (300 MHz, CDCl$_3$) δ 6.38 (d, 1H), 6.35 (d, 1H), 6.05-6.04 (m, 2H), 5.77-5.75 (m, 1H), 4.37 (d, 1H), 4.30-4.25 (m, 1H), 4.18-4.10 (m, 2H), 4.00 (bs, 1H), 3.83 (s, 3H), 3.82 (s, 3H), 2.51-2.46 (m, 1H), 2.39 (s, 3H), 2.31-2.22 (m, 1H), 1.82 (d, 3H), 1.79-1.70 (m, 1H), 1.46 (s, 3H), 1.41 (s, 3H), 1.13 (s, 3H), 1.06 (s, 3H), 0.98-0.91 (m, 4H), 0.74-0.66 (m, 1H).

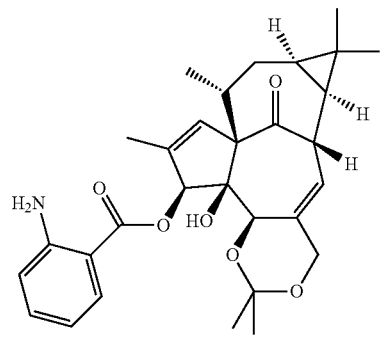 [SMILES: CC1=C[C@]23C(=O)[C@@H](C=C4COC(C)(C)O[C@H]4[C@]2(O)[C@H]1OC(=O)c1ccccc1N)[C@H]1[C@@H](C[C@H]3C)C1(C)C]

Preparation 430

Ingenol-5,20-acetonide-3-(2-amino-benzoate) (Compound 430)

Compound 430 was prepared according to Procedure f.
$^1$H NMR (300 MHz, CDCl$_3$) δ 7.84-7.81 (m, 1H), 7.31-7.25 (m, 1H), 6.69-6.64 (m, 2H), 6.10-6.09 (m, 1H), 5.80-5.73 (m, 4H), 4.26-4.12 (m, 3H), 4.06 (bs, 1H), 3.29 (s, 1H), 2.72-2.63 (m, 1H), 2.31-2.22 (m, 1H), 1.82-1.73 (m, 4H), 1.48 (s, 3H), 1.45 (s, 3H), 1.08 (s, 3H), 1.04-1.02 (m, 6H), 0.95-0.86 (m, 1H), 0.74-0.66 (m, 1H).

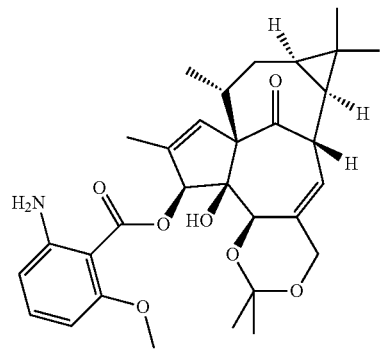 [SMILES: COc1cccc(N)c1C(=O)O[C@H]1C(C)=C[C@]23C(=O)[C@@H](C=C4COC(C)(C)O[C@H]4[C@]12O)[C@H]1[C@@H](C[C@H]3C)C1(C)C]

Preparation 434

Ingenol-5,20-acetonide-3-(2-amino-6-methoxy-benzoate) (Compound 434)

Compound 434 was prepared according to Procedure f, replacing 3,1-benzoxazine-2,4(1H)-dione with 5-methoxy-3,1-benzoxazine-2,4(1H)-dione.
$^1$H NMR (300 MHz, CDCl$_3$) δ 7.16 (t, 1H), 6.32 (dd, 1H), 6.24 (dd, 1H), 6.05 (m, 1H), 5.97 (s, 1H), 5.77-5.75 (m, 1H), 5.39 (bs, 2H), 4.83 (d, 1H), 4.32-4.26 (m, 1H), 4.19-4.09 (m, 2H), 3.99 (bs, 1H), 3.84 (s, 3H), 2.59-2.53 (m, 1H), 2.34-2.25 (m, 1H), 1.85 (d, 3H), 1.82-1.75 (m, 1H), 1.43 (s, 3H), 1.39 (s, 3H), 1.15 (s, 3H), 1.07 (s, 3H), 1.00-0.90 (m, 4H), 0.76-0.68 (m, 1H).

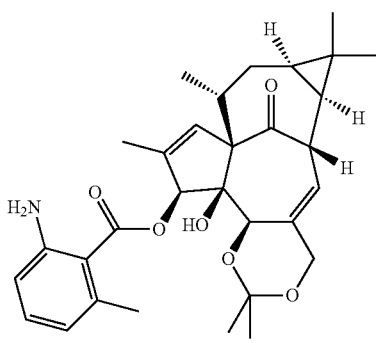 [SMILES: CC1=C[C@]23C(=O)[C@@H](C=C4COC(C)(C)O[C@H]4[C@]2(O)[C@H]1OC(=O)c1c(C)cccc1N)[C@H]1[C@@H](C[C@H]3C)C1(C)C]

Preparation 435

Ingenol-5,20-acetonide-3-(2-amino-6-methyl-benzoate) (Compound 435)

Compound 435 was prepared according to Procedure f, replacing 3,1-benzoxazine-2,4(1H)-dione with 5-methyl-3,1-benzoxazine-2,4(1H)-dione.
$^1$H NMR (300 MHz, CDCl$_3$) δ 7.07 (t, 1H), 6.55-6.51 (m, 2H), 6.07 (m, 1H), 5.89 (s, 1H), 5.83-5.82 (m, 1H), 5.04 (bs, 2H), 4.30-4.10 (m, 4H), 3.49 (s, 1H), 2.70-2.62 (m, 1H), 2.40 (s, 3H), 2.27-2.18 (m, 1H), 1.82 (d, 3H), 1.79-1.71 (m, 1H), 1.48 (s, 3H), 1.48 (s, 3H), 1.08 (s, 3H), 1.05 (s, 3H), 0.96 (d, 3H), 0.94-0.87 (m, 1H), 0.74-0.66 (m, 1H).

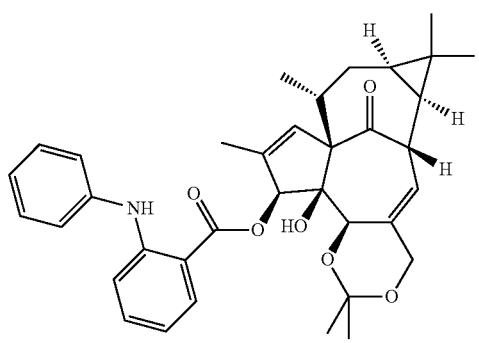

Preparation 436

Ingenol-5,20-acetonide-3-(2-phenylamino-benzoate) (Compound 436)

Compound 436 was prepared according to Procedure c. Starting material: 2-Phenylamino-benzoic acid.

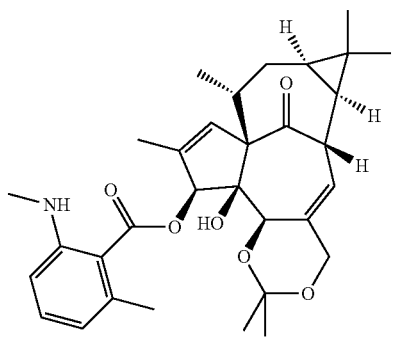

Preparation 439

Ingenol-5,20-acetonide-3-(2-methyl-6-methylamino-benzoate) (Compound 439)

Compound 439 was prepared according to Procedure f, replacing 3,1-benzoxazine-2,4(1H)-dione with 5-methyl-1-methyl-3,1-benzoxazine-2,4(1H)-dione. 5-Methyl-1-methyl-3,1-benzoxazine-2,4(1H)-dione was prepared according to procedure i replacing 3,1-benzoxazine-2,4(1H)-dione with 5-methyl-3,1-benzoxazine-2,4(1H)-dione.

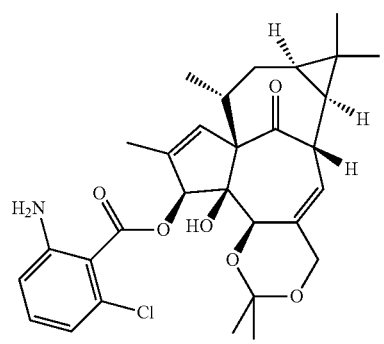 [SMILES: CC1=C[C@]23C(=O)[C@@H](C=C4COC(C)(C)O[C@H]4[C@]2(O)[C@H]1OC(=O)c1c(N)cccc1Cl)[C@H]1[C@@H](C[C@H]3C)C1(C)C]

Preparation 440

Ingenol-5,20-acetonide-3-(2-amino-6-chloro-benzoate) (Compound 440)

Compound 440 was prepared according to Procedure f, but replacing 3,1-benzoxazine-2,4(1H)-dione with 5-chloro-3,1-benzoxazine-2,4(1H)-dione.

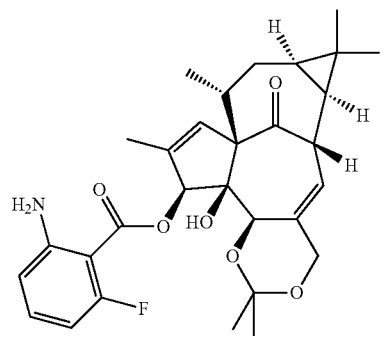 [SMILES: CC1=C[C@]23C(=O)[C@@H](C=C4COC(C)(C)O[C@H]4[C@]2(O)[C@H]1OC(=O)c1c(N)cccc1F)[C@H]1[C@@H](C[C@H]3C)C1(C)C]

Preparation 441

Ingenol-5,20-acetonide-3-(2-amino-6-fluoro-benzoate) (Compound 441)

Compound 441 was prepared according to Procedure f, but replacing 3,1-benzoxazine-2,4(1H)-dione with 5-fluoro-3,1-benzoxazine-2,4(1H)-dione.

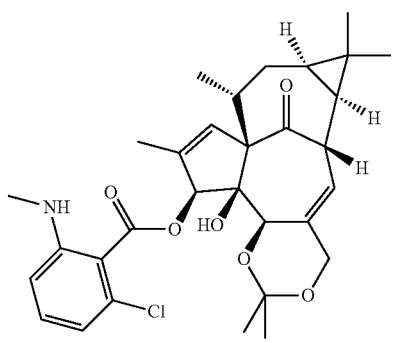

Preparation 442

Ingenol-5,20-acetonide-3-(2-chloro-6-methylamino-benzoate) (Compound 442)

Compound 442 was prepared according to Procedure f, but replacing 3,1-benzoxazine-2,4(1H)-dione with 5-chloro-1-methyl-3,1-benzoxazine-2,4(1H)-dione. This compound was prepared according to Procedure i replacing 3,1-benzoxazine-2,4(1H)-dione with 5-chloro-3,1-benzoxazine-2,4(1H)-dione.

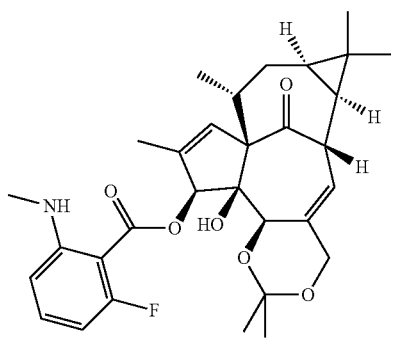

Preparation 443

Ingenol-5,20-acetonide-3-(2-fluoro-6-methylamino-benzoate) (Compound 443)

Compound 443 was prepared according to Procedure f, but replacing 3,1-benzoxazine-2,4(1H)-dione with 5-fluoro-1-methyl-3,1-benzoxazine-2,4(1H)-dione. This compound was prepared according to Procedure i replacing 3,1-benzoxazine-2,4(1H)-dione with 5-fluoro-3,1-benzoxazine-2,4(1H)-dione.

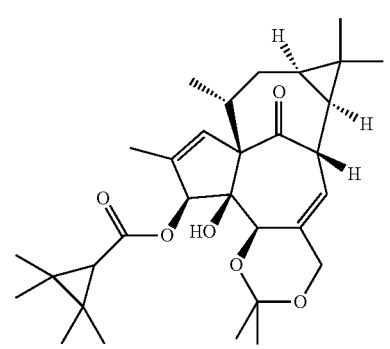

Preparation 444

Ingenol-5,20-acetonide-3-(2,2,3,3-tetramethylcyclo-propylcarboxylate) (Compound 444)

Compound 443 was prepared according to Procedure c.
Starting material: 2,2,3,3-Tetramethylcyclopropylcarboxylic acid.

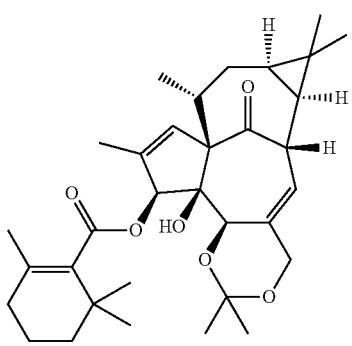 [SMILES: CC1=C[C@]23C(=O)[C@@H](C=C4COC(C)(C)O[C@H]4[C@]2(O)[C@H]1OC(=O)C1=C(C)CCCC1(C)C)[C@H]1[C@@H](C[C@H]3C)C1(C)C]

Preparation 445

Ingenol-5,20-acetonide-3-(2,6,6-trimethylcyclohex-ene-1-carboxylate) (Compound 445)

Compound 445 was prepared according to Procedure d, but with a reaction time of 45 min.

Starting material: 2,6,6-Trimethylcyclohexene-1-carbonyl chloride, prepared from 2,6,6-trimethylcyclohexene-1-carboxylic acid by reaction with 1.25 eq. oxalyl chloride in dichloromethane and a drop of dimethylformamide at room temperature for 30 min followed by evaporation of volatiles in vacuum.

$^1$H NMR (300 MHz, CDCl$_3$) δ 6.05-6.03 (m, 1H), 5.80-5.77 (m, 1H), 5.63 (s, 1H), 4.25-4.12 (m, 3H), 4.04-4.03 (m, 1H), 3.32 (s, 1H), 2.62-2.57 (m, 1H), 2.29-2.20 (m, 1H), 1.99 (t, 2H), 1.80 (d, 3H), 1.77-1.62 (m, 6H), 1.48-1.40 (m, 8H), 1.13 (s, 3H), 1.11 (s, 3H), 1.09 (s, 3H), 1.04 (s, 3H), 0.96 (d, 3H), 0.93-0.87 (m, 1H), 0.72-0.64 (m, 1H).

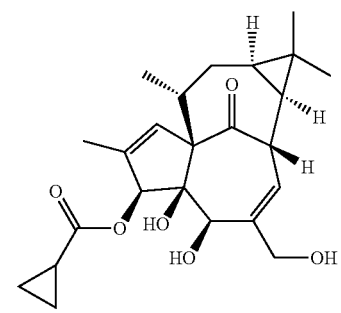 [SMILES: CC1=C[C@]23C(=O)[C@@H](C=C(CO)[C@@H](O)[C@]2(O)[C@H]1OC(=O)C1CC1)[C@H]1[C@@H](C[C@H]3C)C1(C)C]

Example 301

Ingenol 3-(cyclopropanecarboxylate) (Compound 301)

Compound 301 was prepared according to Procedure e.
Starting material: Compound 401.

¹H NMR (300 MHz, CDCl₃) δ 6.05-6.02 (m, 2H), 5.47 (s, 1H), 4.19-4.09 (m, 3H), 4.00 (s, 1H), 3.49 (s, 1H), 2.9-2.4 (bs, 2H), 2.55-2.49 (m, 1H), 2.33-2.23 (m, 1H), 1.83-1.65 (m, 5H), 1.10 (s, 3H), 1.06 (s, 3H), 1.09-0.88 (m, 8H), 0.74-0.65 (m, 1H).

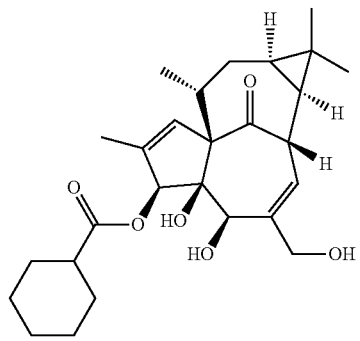 [SMILES: CC1=C[C@]23C(=O)[C@@H](C=C(CO)[C@@H](O)[C@]2(O)[C@H]1OC(=O)C1CCCCC1)[C@H]1[C@@H](C[C@H]3C)C1(C)C]

Example 302

Ingenol 3-(cyclohexanecarboxylate) (Compound 302)

Compound 302 was prepared according to Procedure e. Starting material: Compound 402.

¹H NMR (300 MHz, CDCl₃) δ 6.05-6.01 (m, 2H), 5.45 (s, 1H), 4.16-4.09 (m, 3H), 4.02 (s, 1H), 3.43 (bs, 1H), 2.9-2.2 (bs, 2H), 2.52-2.47 (m, 1H), 2.45-2.36 (m, 1H), 2.30-2.21 (m, 1H), 1.97-1.90 (m, 2H), 1.81-1.65 (m, 7H), 1.54-1.42 (m, 2H), 1.38-1.22 (m, 3H), 1.09 (s, 3H), 1.05 (s, 3H), 0.97 (d, 3H), 0.97-0.90 (m, 1H), 0.73-0.65 (m, 1H).

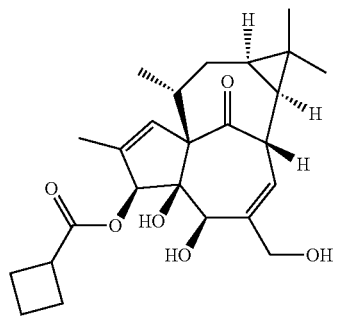 [SMILES: CC1=C[C@]23C(=O)[C@@H](C=C(CO)[C@@H](O)[C@]2(O)[C@H]1OC(=O)C1CCC1)[C@H]1[C@@H](C[C@H]3C)C1(C)C]

Example 303

Ingenol 3-(cyclobutanecarboxylate) (Compound 303)

Compound 303 was prepared according to Procedure e. Starting material: Compound 403.

¹H NMR (300 MHz, CDCl₃) δ 6-05-6.02 (m, 2H), 5.45 (s, 1H), 4.19-4.09 (m, 3H), 4.03 (s, 1H), 3.47 (bs, 1H), 3.28-3.17 (m, 1H), 2.8-2.2 (bs, 2H), 2.52-2.47 (m, 1H), 2.38-2.19 (m, 5H), 2.05-1.91 (m, 2H), 1.80-1.71 (m, 4H), 1.09 (s, 3H), 1.05 (s, 3H), 0.96 (d, 3H), 0.95-0.89 (m, 1H), 0.73-0.65 (m, 1H).

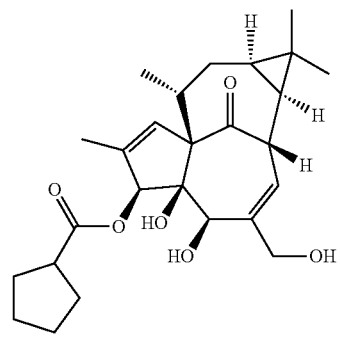 [SMILES: CC1=C[C@]23C(=O)[C@@H](C=C(CO)[C@@H](O)[C@]2(O)[C@H]1OC(=O)C1CCCC1)[C@H]1[C@@H](C[C@H]3C)C1(C)C]

Example 304

Ingenol 3-(cyclopentanecarboxylate) (Compound 304)

Compound 305 was prepared according to Procedure e. Starting material: Compound 404.

¹H NMR (300 MHz, CDCl₃) δ 6.05-6.02 (m, 2H), 5.45 (s, 1H), 4.19-4.09 (m, 3H), 4.02 (s, 1H), 3.45 (bs, 1H), 3-2 (bs, diffuse, 2H), 2.89-2.78 (m, 1H), 2.54-2.49 (m, 1H), 2.31-2.21 (m, 1H), 1.95-1.56 (m, 12H), 1.10 (s, 3H), 1.05 (s, 3H), 0.97 (d, 3H), 0.97-0.88 (m, 1H), 0.73-0.66 (m, 1H).

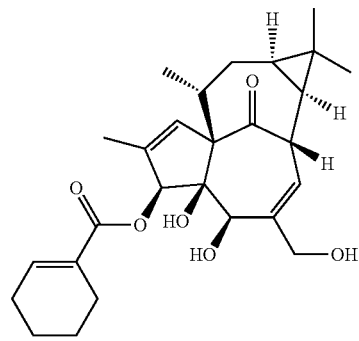 [SMILES: CC1=C[C@]23C(=O)[C@@H](C=C(CO)[C@@H](O)[C@]2(O)[C@H]1OC(=O)C1=CCCCC1)[C@H]1[C@@H](C[C@H]3C)C1(C)C]

Example 305

Ingenol 3-(cyclohexene-1-carboxylate) (Compound 305)

Compound 306 was prepared according to Procedure e. Starting material: Compound 405.

¹H NMR (300 MHz, CDCl₃) δ 7.05-7.03 (m, 1H), 6.05-6.02 (m, 2H), 5.52 (s, 1H), 4.35 (d, 1H), 4.16-4.09 (m, 3H), 4.04 (d, 1H), 3.49 (s, 1H), 2.56-2.49 (m, 2H), 2.29-2.21 (m, 5H), 1.85-1.62 (m, 8H), 1.09 s, 3H), 1.05 (s, 3H), 0.97 (d, 3H), 0.98-0.88 (m, 1H), 0.73-0.65 (m, 1H).

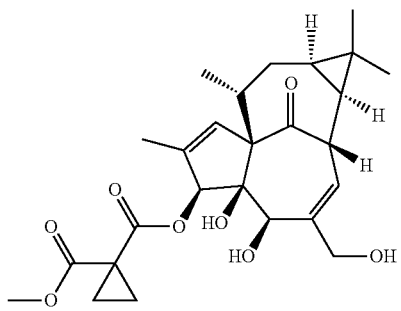

Example 306

Ingenol 3-(1-methoxycarbonyl-cyclopropylcarboxylate) (Compound 306)

Compound 306 was prepared according to Procedure e. Starting material: Compound 406.

$^1$H NMR (300 MHz, CDCl$_3$) δ 6.09-6.07 (m, 1H), 6.05-6.03 (m, 1H), 5.83 (s, 1H), 5.31 (d, 1H), 4.20-4.11 (m, 3H), 4.89 (d, 1H), 3.73 (s, 3H), 3.32 (d, 1H), 2.42-2.27 (m, 3H), 1.85-1.77 (m, 6H), 1.47-1.35 (m, 2H), 1.14 (s, 3H), 1.07 (s, 3H), 0.99 (d, 3H), 0.99-0.92 (m, 1H), 0.75-0.67 (m, 1H).

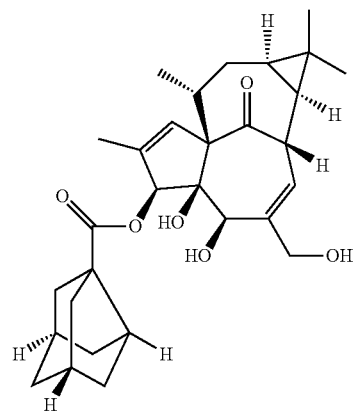 [SMILES: CC1=C[C@]23C(=O)[C@@H](C=C(CO)[C@@H](O)[C@]2(O)[C@H]1OC(=O)C12C[C@@H]4CC1C[C@@H](C4)C2)[C@H]1[C@@H](C[C@H]3C)C1(C)C]

Example 307

Ingenol 3-(noradamantane-3-carboxylate) (Compound 307)

Compound 307 was prepared according to Procedure e. Starting material: Compound 407.

$^1$H NMR (300 MHz, CDCl$_3$) δ 6.06-6.05 (m, 1H), 6.01-6.00 (m, 1H), 5.45 (s, 1H), 4.21-4.19 (d, 1H), 4.16-4.09 (m, 3H), 4.05-4.03 (d, 1H), 3.41 (s, 1H), 2.75-2.71 (t, 1H), 2.54-2.49 (m, 1H), 2.32-2.19 (m, 3H), 2.11-2.07 (m, 2H), 1.89-1.71 (m, 7H), 1.67-1.60 (m, 3H), 1.55 (s, 3H), 1.11 (s, 3H), 1.05 (s, 3H), 1.00-0.90 (4H), 0.73-0.66 (m, 1H).

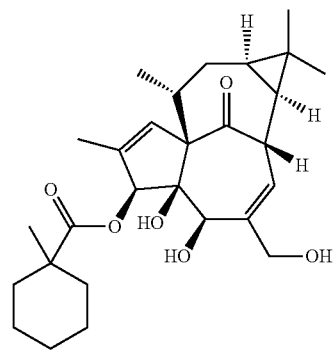 [SMILES: CC1=C[C@]23C(=O)[C@@H](C=C(CO)[C@@H](O)[C@]2(O)[C@H]1OC(=O)C1(C)CCCCC1)[C@H]1[C@@H](C[C@H]3C)C1(C)C]

Example 308

Ingenol 3-(1-methyl-cyclohexanecarboxylate) (Compound 308)

Compound 308 was prepared according to Procedure e. Starting material: Compound 408.

$^1$H NMR (300 MHz, CDCl$_3$) δ 6.06-6.05 (m, 1H), 6.02 (m, 1H), 5.44 (s, 1H), 4.30 (bs, 1H), 4.15-4.10 (m, 3H), 4.05-4.04 (d, 1H), 3.43 (s, 1H), 2.53-2.43 (m, 1H), 2.30-2.21 (m, 2H), 2.08-2.01 (m, 2H), 1.80-1.70 (m, 4H), 1.60-1.20 (m, 8H), 1.21 (s, 3H), 1.09 (s, 3H), 1.05 (s, 3H), 0.97 (d, 3H), 0.96-0.91 (m, 1H), 0.73-0.65 (m, 1H).

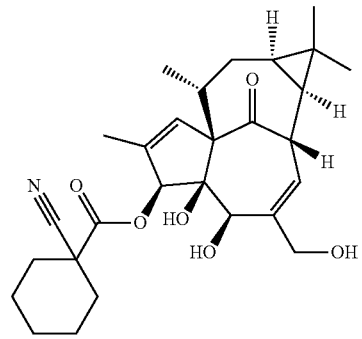 [SMILES: CC1=C[C@]23C(=O)[C@@H](C=C(CO)[C@@H](O)[C@]2(O)[C@H]1OC(=O)C1(C#N)CCCCC1)[C@H]1[C@@H](C[C@H]3C)C1(C)C]

Example 309

Ingenol 3-(1-cyano-cyclohexanecarboxylate) (Compound 309)

Compound 309 was prepared according to Procedure e. Starting material: Compound 409.

$^1$H NMR (300 MHz, CDCl$_3$) δ 6.11 (m, 1H), 6.05 (d, 1H), 6.61 (s, 1H), 4.46 (d, 1H), 4.19-4.13 (m, 3H), 4.04 (d, 1H), 3.54 (s, 1H), 2.61-2.56 (m, 1H), 2.30-2.11 (m, 4H), 1.91-1.60 (m, 11H), 1.27 (bs, 1H), 1.09 (s, 3H), 1.05 (s, 3H), 0.97 (d, 3H), 0.95-0.89 (m, 1H), 0.74-0.67 (m, 1H).

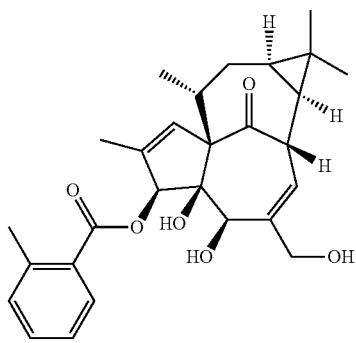 [SMILES: CC1=C[C@]23C(=O)[C@@H](C=C(CO)[C@@H](O)[C@]2(O)[C@H]1OC(=O)c1ccccc1C)[C@H]1[C@@H](C[C@H]3C)C1(C)C]

Example 310

Ingenol 3-(2-methyl-benzoate) (Compound 310)

Compound 310 was prepared according to Procedure e. Starting material: Compound 410.

$^1$H NMR (300 MHz, CDCl$_3$) δ 7.93-7.90 (m, 1H), 7.46-7.41 (m, 1H), 7.30-7.25 (m, 2H), 6.11-6.09 (m, 1H), 6.07-6.06 (m, 1H), 5.73 (s, 1H), 4.20-4.09 (m, 4H), 3.61 (s, 1H), 2.62 (s, 3H), 2.62-2.56 (m, 1H), 2.32-2.23 (m, 1H), 1.85 (d, 3H), 1.81-1.72 (m, 1H), 1.27 (bs, 1H), 1.07 (s, 3H), 1.05 (s, 3H), 1.01 (d, 3H), 1.00-0.85 (m, 2H), 0.74-0.65 (m, 1H).

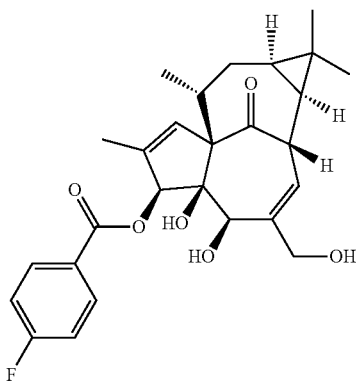 [SMILES: CC1=C[C@]23C(=O)[C@@H](C=C(CO)[C@@H](O)[C@]2(O)[C@H]1OC(=O)c1ccc(F)cc1)[C@H]1[C@@H](C[C@H]3C)C1(C)C]

Example 311

Ingenol 3-(4-fluoro-benzoate) (Compound 311)

Compound 311 was prepared according to Procedure e. Starting material: Compound 411.

$^1$H NMR (300 MHz, CDCl$_3$) δ 8.09-8.03 (m, 2H), 7.18-7.11 (m, 2H), 6.12-6.10 (m, 1H), 6.06-6.05 (m, 1H), 5.74 (s, 1H), 4.23-4.11 (m, 4H), 3.60 (s, 1H), 2.62-2.56 (m, 1H), 2.32-2.21 (m, 1H), 1.83 (d, 3H), 1.83-1.72 (m, 1H), 1.27 (bs, 1H), 1.05-1.02 (m, 9H), 0.95-0.85 (m, 2H), 0.74-0.65 (m, 1H).

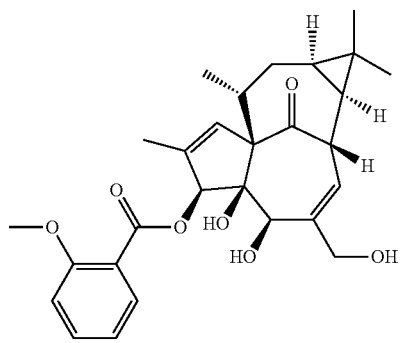

Example 312

Ingenol 3-(2-methoxy-benzoate) (Compound 312)

Compound 312 was prepared according to Procedure e. Starting material: Compound 412.

$^1$H NMR (300 MHz, CDCl$_3$) δ 7.87 (dd, 1H), 7.56-7.50 (m, 1H), 7.10-7.01 (m, 2H), 6.08-6.05 (m, 2H), 5.94 (s, 1H), 4.97 (d, 1H), 4.19-4.13 (m, 3H), 3.95 (s, 1H), 3.94 (s, 3H), 2.52-2.49 (m, 1H), 2.39.2.29 (m, 1H), 1.87 (d, 3H), 1.84-1.77 (m, 1H), 1.27 (bs, 1H), 1.15 (s, 3H), 1.09 (s, 3H), 1.02-0.89 (m, 5H), 0.77-0.69 (m, 1H).

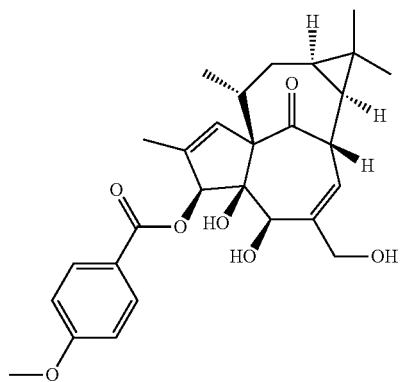

Example 313

Ingenol 3-(4-methoxy-benzoate) (Compound 313)

Compound 313 was prepared according to Procedure e. Starting material: Compound 413.

$^1$H NMR (300 MHz, CDCl$_3$) δ 8.02-7.97 (m, 2H), 6.98-6.93 (m, 2H), 6.09-6.08 (m, 1H), 6.04-6.03 (m, 1H), 5.72 (s, 1H), 4.17-4.10 (m, 4H), 3.87 (s, 3H), 3.57 (s, 1H), 2.62-2.57 (m, 1H), 2.29-2.20 (m, 1H), 1.83 (d, 3H), 1.81-1.72 (m, 1H), 1.27 (bs, 1H), 1.04-1.02 (m, 9H), 0.98-0.89 (m, 2H), 0.73-0.65 (m, 1H).

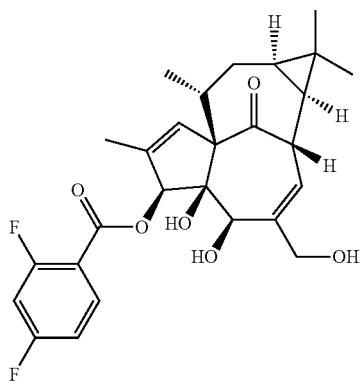 [SMILES: CC1=C[C@]23C(=O)[C@@H](C=C(CO)[C@@H](O)[C@]2(O)[C@H]1OC(=O)c1ccc(F)cc1F)[C@H]1[C@@H](C[C@H]3C)C1(C)C]

Example 314

Ingenol 3-(2,4-difluoro-benzoate) (Compound 314)

Compound 314 was prepared according to Procedure e.
Starting material: Compound 414.

$^1$H NMR (300 MHz, CDCl$_3$) δ 8.05-7.99 (m, 1H), 7.02-6.87 (m, 2H), 6.11-6.10 (m, 1H), 6.07-6.05 (m, 1H), 5.83 (s, 1H), 4.23-4.11 (m, 3H), 4.06 (s, 1H), 3.71 (s, 1H), 2.61-2.56 (m, 1H), 2.32-2.22 (m, 1H), 1.85 (d, 3H), 1.83-1.74 (m, 2H), 1.27 (bs, 1H), 1.09 (s, 3H), 1.05 (s, 3H), 1.00 (d, 3H), 0.99-0.89 (m, 1H), 0.75-0.67 (m, 1H).

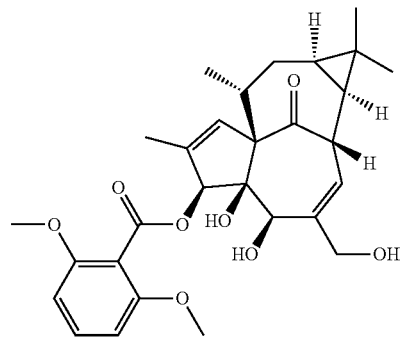

Example 316

Ingenol 3-(2,6-dimethoxy-benzoate) (Compound 316)

Compound 316 was prepared according to Procedure e.
Starting material: Compound 416.

$^1$H NMR (300 MHz, CDCl$_3$) δ 7.36 (t, 1H), 6.63 (d, 2H), 6.13 (s, 1H), 6.06-6.04 (m, 2H), 4.76 (d, 1H), 4.17-4.11 (m, 3H), 3.97-3.94 (m, 1H), 3.87 (s, 6H), 3.20 (d, 1H), 2.39-2.34 (m, 1H), 2.30-2.20 (m, 1H), 1.84 (d, 3H), 1.81-1.72 (m, 1H), 1.60 (s, 1H), 1.13 (s, 3H), 1.07 (s, 3H), 1.03-0.94 (m, 1H), 0.94 (d, 3H), 0.74-0.65 (m, 1H).

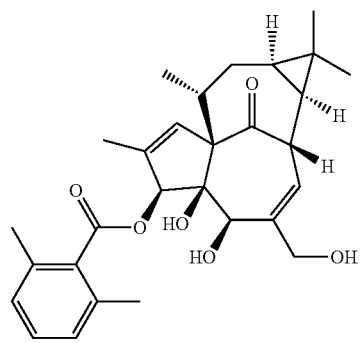 [SMILES: CC1=C[C@]23C(=O)[C@@H](C=C(CO)[C@@H](O)[C@]2(O)[C@H]1OC(=O)c1c(C)cccc1C)[C@H]1[C@@H](C[C@H]3C)C1(C)C]

Example 315

Ingenol 3-(2,6-dimethyl-benzoate) (Compound 315)

Compound 315 was prepared according to Procedure e.
Starting material: Compound 415.

$^1$H NMR (300 MHz, CDCl$_3$) δ 7.24-7.19 (m, 1H), 7.05 (d, 2H), 6.09-6.08 (m, 2H), 5.81 (s, 1H), 4.34 (bs, 1H), 4.23-4.12 (m, 4H), 3.74 (s, 1H), 2.51-2.43 (m, 1H), 2.37 (s, 6H), 2.32-2.23 (m, 1H), 1.85 (bs, 3H), 1.75-1.68 (m, 1H), 1.59 (s, 1H), 1.09 (s, 3H), 1.05 (s, 3H), 0.95-0.89 (m, 4H), 0.73-0.65 (m, 1H).

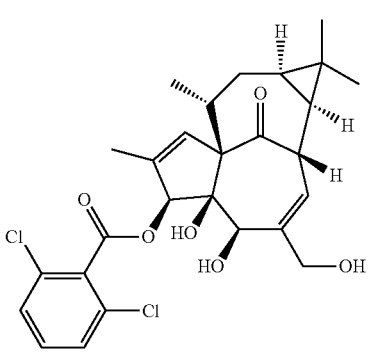 [SMILES: CC1=C[C@]23C(=O)[C@@H](C=C(CO)[C@@H](O)[C@]2(O)[C@H]1OC(=O)c1c(Cl)cccc1Cl)[C@H]1[C@@H](C[C@H]3C)C1(C)C]

Example 317

Ingenol 3-(2,6-dichloro-benzoate) (Compound 317)

Compound 317 was prepared according to Procedure e.
Starting material: Compound 417.

$^1$H NMR (300 MHz, CDCl$_3$) δ 7.38-7.29 (m, 3H), 6.10-6.05 (m, 2H), 5.99 (s, 1H), 4.21-4.13 (m, 3H), 4.07-4.00 (m, 2H), 3.66 (s, 1H), 2.49-2.44 (m, 1H), 2.30-2.21 (m, 2H), 1.88 (d, 3H), 1.78-1.69 (m, 1H), 1.10 (s, 3H), 1.05 (s, 3H), 0.97-0.85 (m, 4H), 0.73-0.65 (m, 1H).

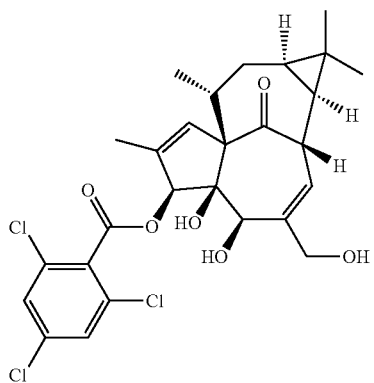 [SMILES: CC1=C[C@]23C(=O)[C@@H](C=C(CO)[C@@H](O)[C@]2(O)[C@H]1OC(=O)c1c(Cl)cc(Cl)cc1Cl)[C@H]1[C@@H](C[C@H]3C)C1(C)C]

Example 318

Ingenol 3-(2,4,6-trichloro-benzoate) (Compound 318)

Compound 318 was prepared according to Procedure e.
Starting material: Compound 418.

$^1$H NMR (300 MHz, CDCl$_3$) δ 7.38 (s, 2H), 6.11-6.10 (m, 1H), 6.07 (d, 1H), 4.26-4.13 (m, 3H), 4.10-4.05 (m, 2H), 3.62 (s, 1H), 2.49-2.43 (m, 1H), 2.30-2.21 (m, 1H), 2.16-2.12 (m, 1H), 1.88 (d, 3H), 1.78-1.69 (m, 1H), 1.56 (s, 1H), 1.09 (s, 3H), 1.05 (s, 3H), 0.97-0.85 (m, 4H), 0.73-0.85 (m, 1H).

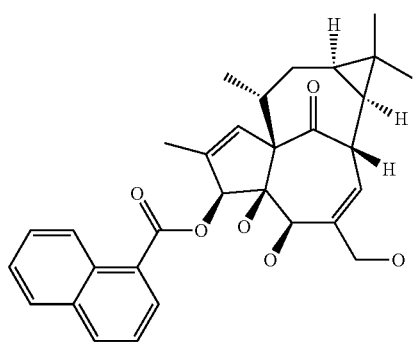 [SMILES: CC1=C[C@]23C(=O)[C@@H](C=C(CO)[C@@H](O)[C@]2(O)[C@H]1OC(=O)c1cccc2ccccc12)[C@H]1[C@@H](C[C@H]3C)C1(C)C]

Example 319

Ingenol 3-(naphthalene-1-carboxylate) (Compound 319)

Compound 319 was prepared according to Procedure e.
Starting material: Compound 419.

$^1$H NMR (300 MHz, CDCl$_3$) δ 8.95 (d, 1H), 8.18 (dd, 1H), 8.05 (d, 1H), 7.90 (m, 1H), 7.64-7.50 (m, 3H), 6.13-6.14 (m, 1H), 6.05 (d, 1H), 5.88 (s, 1H), 4.59 (bs, 1H), 4.23-4.16 (m, 3H), 3.73 (s, 1H), 2.69-2.63 (m, 1H), 2.52 (bs, 1H), 2.36-2.27 (m, 1H), 1.87 (s, 3H), 1.83-1.74 (m, 1H), 1.27 (bs, 1H), 1.06 (s, 3H), 1.04 (s, 3H), 1.03 (d, 3H), 0.97-0.86 (m, 1H), 0.74-0.67 (m, 1H).

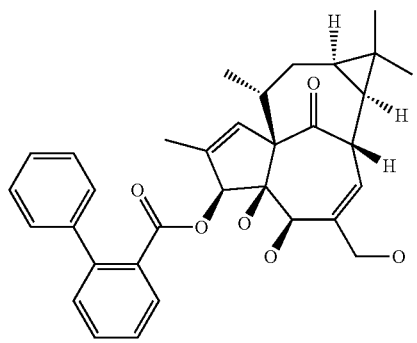 [SMILES: CC1=C[C@]23C(=O)[C@@H](C=C(CO)[C@@H](O)[C@]2(O)[C@H]1OC(=O)c1ccccc1-c1ccccc1)[C@H]1[C@@H](C[C@H]3C)C1(C)C]

Example 320

Ingenol 3-(2-phenyl-benzoate) (Compound 320)

Compound 320 was prepared according to Procedure e.
Starting material: Compound 420.

$^1$H NMR (300 MHz, CDCl$_3$) δ 7.83 (dd, 1H), 7.56 (dt, 1H), 7.49-7.35 (m, 7H), 5.99 (d, 1H), 5.92, (m, 1H), 5.66 (s, 1H), 4.10-4.06 (m, 2H), 3.97-3.92 (m, 1H), 3.86 (d, 1H), 3.52 (d, 1H), 2.70 (s, 1H), 2.31-2.27 (m, 1H), 2.04-1.91 (m, 1H), 1.70 (d, 3H), 1.66-1.57 (m, 1H), 1.06 (s, 3H), 1.05 (s, 3H), 0.91-0.81 (m, 5H), 0.69-0.60 (m, 1H).

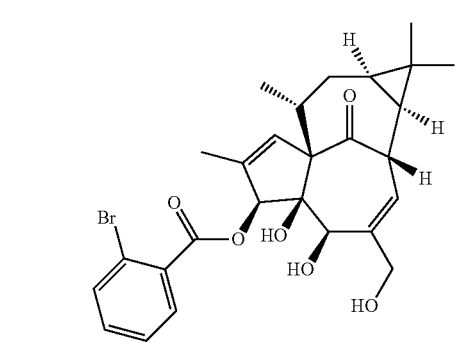 [SMILES: CC1=C[C@]23C(=O)[C@@H](C=C(CO)[C@@H](O)[C@]2(O)[C@H]1OC(=O)c1ccccc1Br)[C@H]1[C@@H](C[C@H]3C)C1(C)C]

Example 321

Ingenol 3-(2-bromo-benzoate) (Compound 321)

Compound 321 was prepared according to Procedure e, but changing the reaction temperature to 37° C.
Starting material: Compound 421.

$^1$H NMR (300 MHz, CDCl$_3$) δ 7.85-7.82 (m, 1H), 7.70-7.65 (m, 1H), 7.44-7.33 (m, 2H), 6.11-6.10 (m, 1H), 6.08-6.06 (m, 1H), 5.86 (s, 1H), 4.23-4.14 (m, 4H), 4.10-4.08 (m, 1H), 3.75 (s, 1H), 2.65-2.56 (m, 1H), 2.38-2.23 (m, 2H), 1.86 (d, 3H), 1.81-1.72 (m, 1H), 1.08 (s, 3H), 1.05 (s, 3H), 0.99 (d, 3H), 0.95-0.86 (m, 1H), 0.74-0.65 (m, 1H).

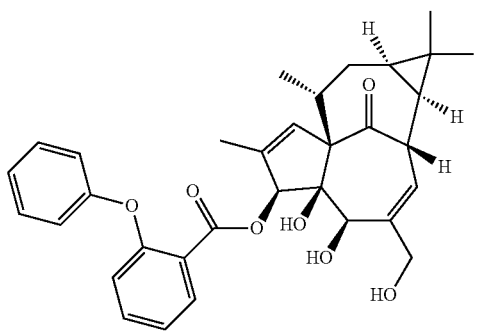 [SMILES: CC1=C[C@]23C(=O)[C@@H](C=C(CO)[C@@H](O)[C@]2(O)[C@H]1OC(=O)c1ccccc1Oc1ccccc1)[C@H]1[C@@H](C[C@H]3C)C1(C)C]

Example 322

Ingenol 3-(2-phenoxy-benzoate) (Compound 322)

Compound 322 was prepared according to Procedure e.
Starting material: Compound 422.
¹H NMR (300 MHz, CDCl₃) δ 8.01-7.99 (m, 1H), 7.45-7.38 (m, 3H), 7.25-7.14 (m, 2H), 7.10-7.07 (m, 2H), 6.82 (d, 1H), 6.05-6.04 (m, 1H), 6.00-5.99 (m, 1H), 5.96 (s, 1H), 4.59 (s, 1H), 4.15-4.09 (m, 2H), 4.00-3.92 (m, 2H), 3.25-3.28 (m, 1H), 2.32-2.20 (m, 2H), 1.87 (s, 3H), 1.80-1.71 (m, 1H), 1.22-1.14 (m, 1H), 1.00 (s, 3H), 0.89-0.83 (m, 7H), 0.58-0.50 (m, 1H).

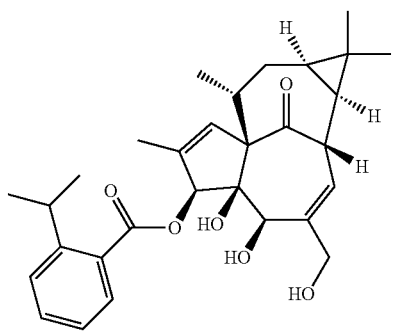 [SMILES: CC1=C[C@]23C(=O)[C@@H](C=C(CO)[C@@H](O)[C@]2(O)[C@H]1OC(=O)c1ccccc1C(C)C)[C@H]1[C@@H](C[C@H]3C)C1(C)C]

Example 323

Ingenol 3-(2-isopropyl-benzoate) (Compound 323)

Compound 323 was prepared according to Procedure e.
Starting material: Compound 423.
¹H NMR (300 MHz, CDCl₃) δ 7.74-7.71 (m, 1H), 7.52-7.41 (m, 2H), 7.27-7.22 (m, 1H), 6.10-6.05 (m, 2H), 5.74 (s, 1H), 4.43 (d, 1H), 4.22-4.12 (m, 4H), 3.75 (septet, 1H), 3.65 (s, 1H), 2.63-2.54 (m, 1H), 2.40-2.25 (m, 2H), 1.84 (d, 3H), 1.81-1.72 (m, 1H), 1.26 (2d, 6H), 1.08 (s, 3H), 1.05 (s, 3H), 0.99 (d, 3H), 0.95-0.86 (m, 1H), 0.74-0.66 (m, 1H).

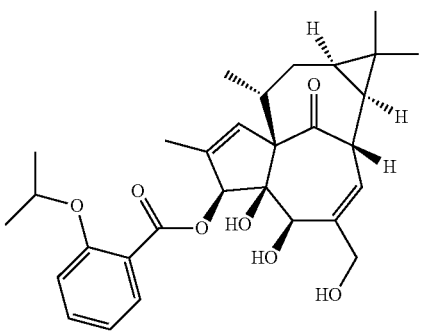 [SMILES: CC1=C[C@]23C(=O)[C@@H](C=C(CO)[C@@H](O)[C@]2(O)[C@H]1OC(=O)c1ccccc1OC(C)C)[C@H]1[C@@H](C[C@H]3C)C1(C)C]

Example 324

Ingenol 3-(2-isopropoxy-benzoate) (Compound 324)

Compound 324 was prepared according to Procedure e.
Starting material: Compound 424.
¹H NMR (300 MHz, CDCl₃) δ 7.75 (dd, 1H), 7.50-7.44 (m, 1H), 7.04-6.99 (m, 2H), 6.07-6.04 (m, 2H), 5.92 (s, 1H), 4.70 (septet, 1H), 4.49 (d, 1H), 4.18-4.09 (m, 3H), 3.96 (d, 1H), 3.30 (d, 1H), 2.50-2.40 (m, 1H), 2.35-2.26 (m, 2H), 1.86 (d, 3H), 1.81-1.72 (m, 1H), 1.44 (d, 3H), 1.35 (d, 3H), 1.12 (s, 3H), 1.07 (s, 3H), 1.01-0.94 (m, 4H), 0.75-0.67 (m, 1H).

Example 325

Ingenol 3-(2,4,6-trimethyl-benzoate) (Compound 325)

Compound 325 was prepared according to Procedure e.
Starting material: Compound 425.
¹H NMR (300 MHz, CDCl₃) δ 6.88 (s, 2H), 6.07-6.08 (m, 2H), 5.79 (s, 1H), 6.37 (d, 1H), 4.22-4.10 (m, 4H), 3.73 (s, 1H), 2.54-2.39 (m, 2H), 2.33 (s, 6H), 2.29 (s, 3H), 2.28-2.21 (m, 1H), 1.85 (s, 3H), 1.75-1.66 (m, 1H), 1.08 (s, 3H), 1.05 (s, 3H), 0.96-0.88 (m, 4H), 0.72-0.64 (m, 1H).

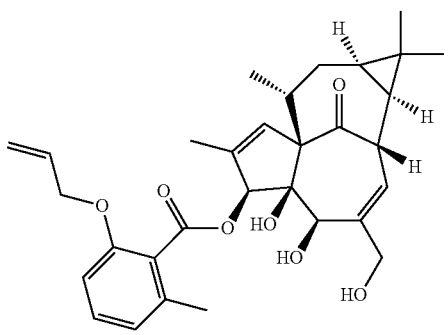 [SMILES: C=CCOc1cccc(C)c1C(=O)O[C@H]1C(C)=C[C@]23C(=O)[C@@H](C=C(CO)[C@@H](O)[C@]12O)[C@H]1[C@@H](C[C@H]3C)C1(C)C]

Example 326

Ingenol 3-(2-allyloxy-6-methyl-benzoate) (Compound 326)

Compound 326 was prepared according to Procedure e.

Starting material: Compound 426.

$^1$H NMR (300 MHz, CDCl$_3$) δ 7.27 (t, 1H), 6.88 (d, 1H), 6.81 (d, 1H), 6.09-5.94 (m, 3H), 5.39-5.29 (m, 3H), 4.65-4.63 (m, 2H), 4.43 (d, 1H), 4.19-4.07 (m, 3H), 3.96 (m, 1H), 3.30 (d, 1H), 2.37-2.32 (m, 5H), 2.25-2.16 (m, 1H), 1.84 (d, 3H), 1.76-1.67 (m, 1H), 1.10 (s, 3H), 1.06 (s, 3H), 0.99-0.91 (m, 4H), 0.73-0.65 (m, 1H).

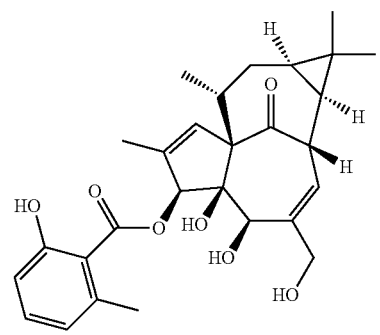

Example 327

Ingenol 3-(2-hydroxy-6-methyl-benzoate) (Compound 327)

Compound 427 (30 mg) was dissolved in methanol (1.0 mL) and two drops of conc. HCl was added. The solution was stirred at room temperature for 0.5 h and toluene (5 ml) was added. The solution was concentrated in vacuo and the residue purified by chromatography as described in Procedure e to give the title compound.

$^1$H NMR (300 MHz, CDCl$_3$) δ 10.70 (s, 1H), 7.29 (t, 1H), 6.86 (d, 1H), 6.74 (d, 1H), 6.14 (m, 1H), 6.09 (d, 1H), 5.85 (s, 1H), 4.25-4.11 (m, 4H), 3.89 (s, 1H), 2.63-2.58 (m, 1H), 2.54 (s, 3H), 2.5-2.2 (bs, 1H), 2.36-2.25 (m, 1H), 1.86 (d, 3H), 1.80-1.71 (m, 1H), 1.07 (s, 3H), 1.06 (s, 3H), 1.00 (d, 3H), 0.96-0.89 (m, 2H), 0.74-0.66 (m, 1H).

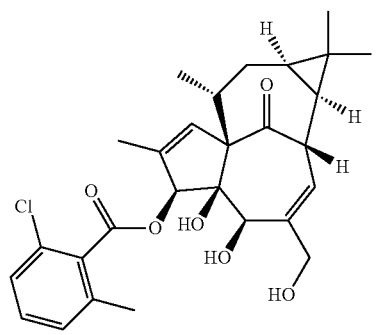 [SMILES: CC1=C[C@]23C(=O)[C@@H](C=C(CO)[C@@H](O)[C@]2(O)[C@H]1OC(=O)c1c(C)cccc1Cl)[C@H]1[C@@H](C[C@H]3C)C1(C)C]

Example 328

Ingenol 3-(2-chloro-6-methyl-benzoate) (Compound 328)

Compound 328 was prepared according to Procedure e.

Starting material: Compound 428.

$^1$H NMR (300 MHz, CDCl$_3$) δ 7.26-7.23 (m, 2H), 7.17-7.13 (m, 1H), 6.09-6.07 (m, 2H), 5.91 (s, 1H), 4.20-4.08 (m, 5H), 3.78 (s, 1H), 2.49-2.43 (m, 1H), 2.40-2-35 (m, 4H), 2.31-2.22 (m, 1H), 1.88 (d, 3H), 1.77-1.68 (m, 1H), 1.09 (s, 3H), 1.05 (s, 3H), 0.97-0.90 (m, 4H), 0.73-0.65 (m, 1H).

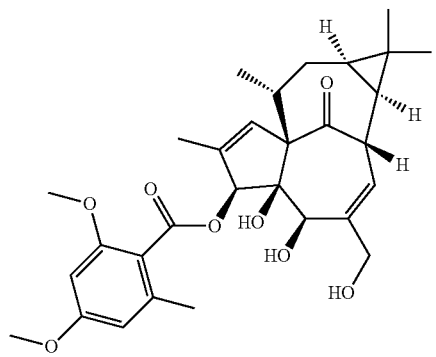

Example 329

Ingenol 3-(2,4-dimethoxy-6-methyl-benzoate) (Compound 329)

Compound 329 was prepared according to Procedure e.

Starting material: Compound 429.

$^1$H NMR (300 MHz, CDCl$_3$) δ 6.41 (d, 1H), 6.37 (d, 1H), 6.08 (s, 1H), 6.06-6.04 (m, 2H), 4.93 (d, 1H), 4.17-4.11 (m, 3H), 3.95 (d, 1H), 3.85 (s, 3H), 3.83 (s, 3H), 3.24 (d, 1H), 2.40-2.23 (m, 6H), 1.82 (s, 3H), 1.81-1.72 (m, 1H), 1.14 (s, 3H), 1.07 (s, 3H), 1.00-0.93 (m, 4H), 0.75-0.67 (m, 1H).

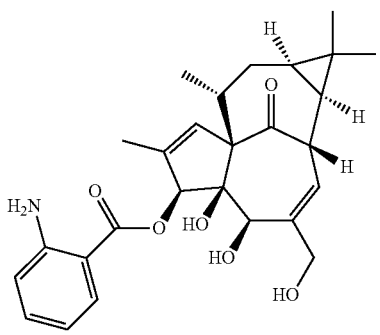 [SMILES: CC1=C[C@]23C(=O)[C@@H](C=C(CO)[C@@H](O)[C@]2(O)[C@H]1OC(=O)c1ccccc1N)[C@H]1[C@@H](C[C@H]3C)C1(C)C]

Example 330

Ingenol 3-(2-amino-benzoate) (Compound 330)

Compound 330 was prepared according to Procedure e.
Starting material: Compound 430.

$^1$H NMR (300 MHz, CDCl$_3$) δ 7.84-7.80 (m, 1H), 7.33-7.27 (m, 1H), 6.70-6.65 (m, 2H), 6.10-6.09 (m, 1H), 6.06 (d, 1H), 5.76 (bs, 2H), 5.52 (s, 1H), 4.34 (bs, 1H), 4.19-4.11 (m, 4H), 3.57 (s, 1H), 2.62-2.57 (m, 1H), 2.31-2.22 (m, 2H), 1.83 (d, 3H), 1.80-1.73 (m, 1H), 1.07 (s, 3H), 1.05-1.02 (m, 6H), 0.95-0.86 (m, 1H), 0.74-0.67 (m, 1H).

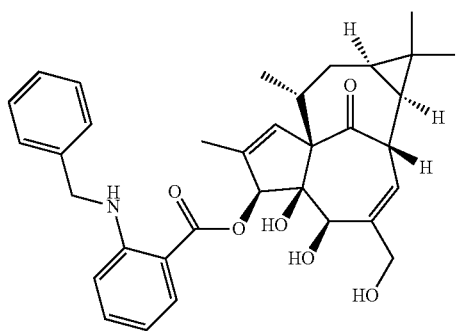 [SMILES: CC1=C[C@]23C(=O)[C@@H](C=C(CO)[C@@H](O)[C@]2(O)[C@H]1OC(=O)c1ccccc1NCc1ccccc1)[C@H]1[C@@H](C[C@H]3C)C1(C)C]

Example 331

Ingenol 3-(2-benzylamino-benzoate) (Compound 331)

Compound 331 was prepared according to Procedure g.
Starting aldehyde material: Benzaldehyde.

$^1$H NMR (300 MHz, CDCl$_3$) δ 8.14 (t, 1H), 7.89 (dd, 1H), 7.38-7.24 (m, 6H), 6.67-6.60 (m, 2H), 6.01-6.05 (m, 2H), 5.73 (s, 1H), 4.46 (d, 2H), 4.32 (bs, 1H), 4.19-4.10 (m, 4H), 3.58 (s, 1H), 2.63-2.58 (m, 1H), 2.33-2.22 (m, 2H), 1.83 (d, 3H), 1.80-1.73 (m, 1H), 1.07 (s, 3H), 1.05-1.02 (m, 6H), 0.98-0.85 (m, 1H), 0.74-0.66 (m, 1H).

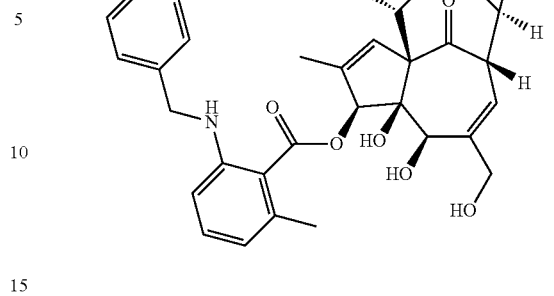

Example 332

Ingenol 3-(2-benzylamino-6-methyl-benzoate) (Compound 332)

Compound 332 was prepared according to Procedure g, but replacing ingenol-5,20-acetonide-3-(2-amino-benzoate) with ingenol-5,20-acetonide-3-(2-amino-6-methyl-benzoate).
Starting aldehyde material: Benzaldehyde.

$^1$H NMR (300 MHz, CDCl$_3$) δ 7.32-7.22 (m, 6H), 7.09 (dd, 1H), 6.91 (bs, 1H), 6.50 (d, 1H), 6.44 (d, 1H), 6.08-6.06 (m, 2H), 5.82 (s, 1H), 4.53 (bs, 1H), 4.41 (s, 2H), 4.18-4.13 (m, 4H), 3.85 (s, 1H), 2.60-2.52 (m, 1H), 2.42 (s, 3H), 2.25-2.16 (m, 1H), 1.81 (s, 3H), 1.63-1.58 (m, 1H), 1.03 (s, 6H), 0.93-0.85 (m, 4H), 0.68-0.60 (m, 1H).

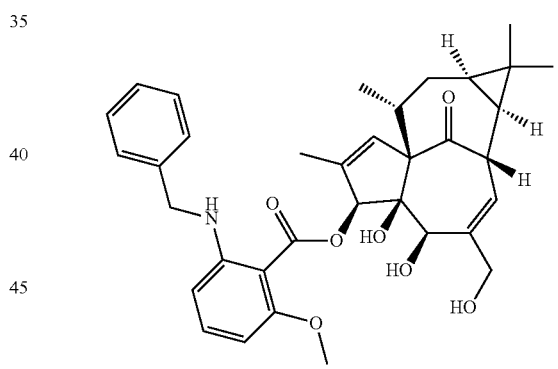

Example 333

Ingenol 3-(2-benzylamino-6-methoxy-benzoate) (Compound 333)

Compound 333 was prepared according to Procedure g, but replacing ingenol-5,20-acetonide-3-(2-amino-benzoate) with ingenol-5,20-acetonide-3-(2-amino-6-methoxy-benzoate).
Starting aldehyde material: Benzaldehyde.

$^1$H NMR (300 MHz, CDCl$_3$) δ 7.47 (t, 1H), 7.36-7.17 (m, 6H), 6.31 (d, 1H), 6.25 (d, 1H), 6.07-6.05 (m, 2H), 5.99 (s, 1H), 5.31 (d, 1H), 4.43 (d, 2H), 4.18-4.12 (m, 3H), 3.94 (d, 1H), 3.87 (s, 3H), 3.16 (d, 1H), 2.50-2.45 (m, 1H), 2.38-2.27 (m, 2H), 1.85 (d, 3H), 1.83-1.75 (m, 1H), 1.15 (s, 3H), 1.09 (s, 3H), 0.97 (d, 3H), 0.90-0.85 (m, 1H), 0.77-0.69 (m, 1H).

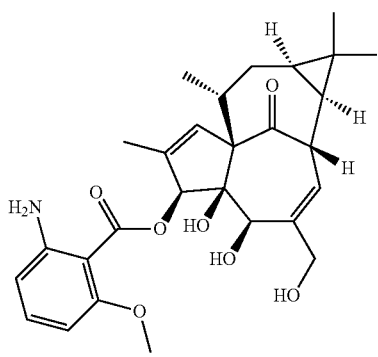 [SMILES: COc1cccc(N)c1C(=O)O[C@H]1C(C)=C[C@]23C(=O)[C@@H](C=C(CO)[C@@H](O)[C@]12O)[C@H]1[C@@H](C[C@H]3C)C1(C)C]

Example 334

Ingenol 3-(2-amino-6-methoxy-benzoate) (Compound 334)

Compound 334 was prepared according to Procedure e. Starting material: Compound 434.

$^1$H NMR (300 MHz, CDCl$_3$) δ 7.18 (t, 1H), 6.35 (dd, 1H), 6.26 (dd, 1H), 6.07-6.05 (m, 2H), 5.98 (s, 1H), 5.37 (bs, 2H), 5.29 (d, 1H), 4.16-4.11 (m, 3H), 3.94 (d, 1H), 3.86 (s, 3H), 3.14 (d, 1H), 2.50-2.42 (m, 1H), 2.38-2.25 (m, 2H), 1.86 (d, 3H), 1.83-1.75 (m, 1H), 1.15 (s, 3H), 1.08 (s, 3H), 0.96 (d, 3H), 0.90-0.85 (m, 1H), 0.77-0.71 (m, 1H).

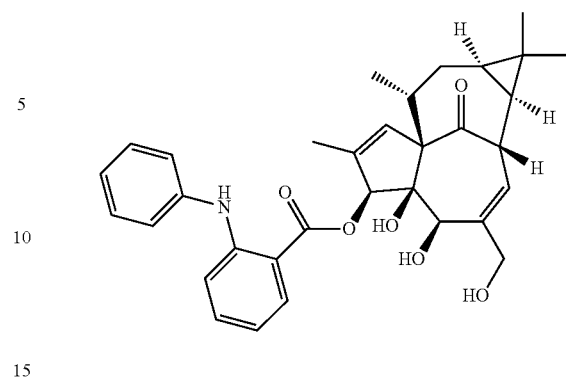

Example 336

Ingenol 3-(2-phenylamino-benzoate) (Compound 336)

Compound 336 was prepared according to Procedure e. Starting material: Compound 436.

$^1$H NMR (300 MHz, CDCl$_3$) δ 9.37 (s, 1H), 7.93 (dd, 1H), 7.37-7.31 (m, 3H), 7.25-7.23 (m, 2H), 7.13-7.08 (m, 1H), 6.78-6.73 (m, 1H), 6.12 (m, 1H), 6.07 (d, 1H), 5.78 (s, 1H), 5.44 (d, 1H), 4.21-4.11 (m, 4H), 3.63 (s, 1H), 2.66-2.58 (m, 1H), 2.33-2.23 (m, 2H), 1.85 (d, 3H), 1.82-1.73 (m, 1H), 1.57 (s, 1H), 1.07 (s, 3H), 1.05-1.03 (m, 6H), 0.98-0.85 (m, 1H), 0.75-0.67 (m, 1H).

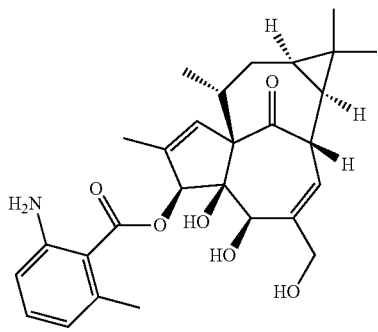 [SMILES: CC1=C[C@]23C(=O)[C@@H](C=C(CO)[C@@H](O)[C@]2(O)[C@H]1OC(=O)c1c(C)cccc1N)[C@H]1[C@@H](C[C@H]3C)C1(C)C]

Example 335

Ingenol 3-(2-amino-6-methyl-benzoate) (Compound 335)

Compound 335 was prepared according to Procedure e. Starting material: Compound 435.

$^1$H NMR (300 MHz, CDCl$_3$) δ 7.09 (t, 1H), 7.55 (d, 1H), 7.53 (d, 1H), 6.08-6.07 (m, 2H), 5.82 (s, 1H), 5.00 (bs, 3H), 4.20-4.12 (m, 4H), 2.62-2.54 (m, 1H), 2.41 (s, 3H), 2.29-2.20 (m, 1H), 2.00 (s, 1H), 1.81 (s, 3H), 1.79-1.70 (m, 1H), 1.70 (bs, 1H), 1.07 (s, 3H), 1.05 (s, 3H), 0.98-0.90 (m, 4H), 0.74-0.65 (m, 1H).

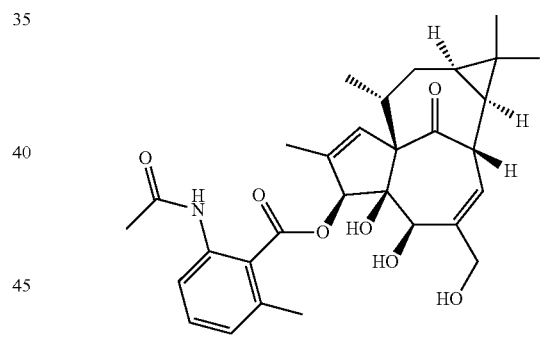

Example 337

Ingenol 3-(2-acetylamino-6-methyl-benzoate) (Compound 337)

Compound 337 was prepared according to Procedure h. Starting material: Acetyl chloride.

$^1$H NMR (300 MHz, CDCl$_3$) δ 8.73 (bs, 1H), 7.95 (d, 1H), 7.33 (t, 1H), 7.01 (d, 1H), 6.11-6.09 (m, 2H), 5.92 (s, 1H), 4.67 (bs, 1H), 4.22-4.12 (m, 5H), 2.55-2.47 (m, 1H), 2.41 (s, 3H), 2.33-2.16 (m, 5H), 1.84 (d, 3H), 1.82-1.73 (m, 1H), 1.08 (s, 3H), 1.06 (s, 3H), 0.98-0.85 (m, 4H), 0.75-0.67 (m, 1H).

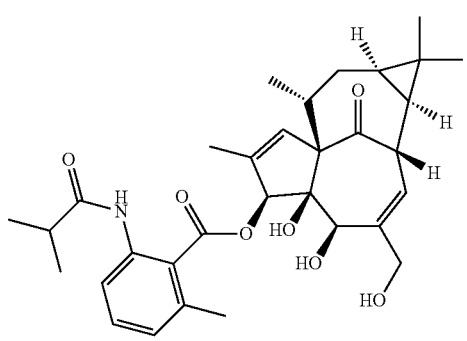 [SMILES: CC1=C[C@]23C(=O)[C@@H](C=C(CO)[C@@H](O)[C@]2(O)[C@H]1OC(=O)c1c(C)cccc1NC(=O)C(C)C)[C@H]1[C@@H](C[C@H]3C)C1(C)C]

Example 338

Ingenol 3-(2-methyl-6-(2-methylpropanoylamino)-benzoate) (Compound 338)

Compound 338 was prepared according to Procedure h.
Starting material: 2-Methyl-propanoyl chloride.

$^1$H NMR (300 MHz, CDCl$_3$) δ 8.71 (bs, 1H), 7.90 (d, 1H), 7.33 (t, 1H), 7.01 (d, 1H), 7.13-7.12 (m, 1H), 6.09 (d, 1H), 5.91 (s, 1H), 4.39 (bs, 1H), 4.20 (m, 5H), 2.60-2.49 (m, 2H), 2.43 (s, 3H), 2.32-2.21 (m, 2H), 1.86 (d, 3H), 1.80-1.71 (m, 1H), 1.23 (d, 3H), 1.21 (d, 3H), 1.08 (s, 3H), 1.06 (s, 3H), 0.97 (d, 3H), 0.91-0.86 (m, 1H), 0.74-0.66 (m, 1H).

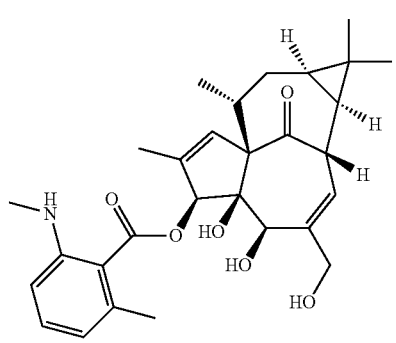

Example 339

Ingenol 3-(2-methyl-6-methylamino-benzoate) (Compound 339)

Compound 339 was prepared according to Procedure e.
Starting material: Compound 439.

$^1$H NMR (300 MHz, CDCl$_3$) δ 7.20 (dd, 1H), 6.53-6.40 (m, 3H), 6.08-6.07 (m, 2H), 5.81 (s, 1H), 4.66 (bs, 1H), 4.23-4.11 (m, 4H), 3.96 (bs, 1H), 2.83 (s, 3H), 2.60-2.45 (m, 2H), 2.40 (s, 3H), 2.34-2.25 (m, 1H), 1.82 (s, 3H), 1.79-1.72 (m, 1H), 1.09 (s, 3H), 1.05 (s, 3H), 0.97 (d, 3H), 0.97-0.90 (m, 1H), 0.74-0.66 (m, 1H).

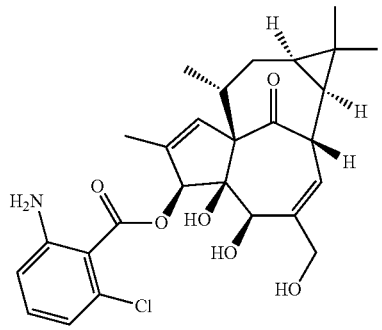 [SMILES: CC1=C[C@]23C(=O)[C@@H](C=C(CO)[C@@H](O)[C@]2(O)[C@H]1OC(=O)c1c(N)cccc1Cl)[C@H]1[C@@H](C[C@H]3C)C1(C)C]

Example 340

Ingenol 3-(2-amino-6-chloro-benzoate) (Compound 340)

Compound 340 was prepared according to Procedure e.
Starting material: Compound 440.

$^1$H NMR (300 MHz, CDCl$_3$) δ 7.10 (t, 1H), 6.74 (dd, 1H), 6.59 (dd, 1H), 6.08-6.07 (m, 2H), 5.95 (s, 1H), 5.04 (m, 2H), 4.23-4.09 (m, 5H), 5.61-5.56 (m, 1H), 2.45 (bs, 1H), 2.26-2.17 (m, 1H), 1.83 (d, 3H), 1.81-1.72 (m, 1H), 1.63 (bs, 1H), 1.08 (s, 3H), 1.06 (s, 3H), 0.98-0.90 (m, 4H), 0.75-0.67 (m, 1H).

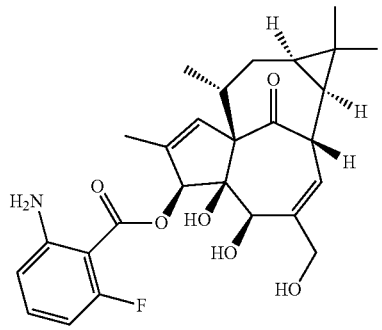 [SMILES: CC1=C[C@]23C(=O)[C@@H](C=C(CO)[C@@H](O)[C@]2(O)[C@H]1OC(=O)c1c(N)cccc1F)[C@H]1[C@@H](C[C@H]3C)C1(C)C]

Example 341

Ingenol 3-(2-amino-6-fluoro-benzoate) (Compound 341)

Compound 341 was prepared according to Procedure e.
Starting material: Compound 441.

$^1$H NMR (300 MHz, CDCl$_3$) δ 7.23-7.15 (m, 1H), 6.47 (d, 1H), 6.38 (dd, 1H), 6.09-6.06 (m, 2H), 5.88 (s, 1H), 5.80 (bs, 2H), 4.22-4.11 (m, 3H), 4.01 (s, 1H), 3.90 (bs, 1H), 3.60 (bs, 1H), 2.60-2.55 (m, 1H), 2.31-2.21 (m, 1H), 1.86 (d, 3H), 1.84-1.77 (m, 1H), 1.65 (bs, 1H), 1.11 (s, 3H), 1.07 (s, 3H), 1.00-0.90 (m, 4H), 0.76-0.69 (m, 1H).

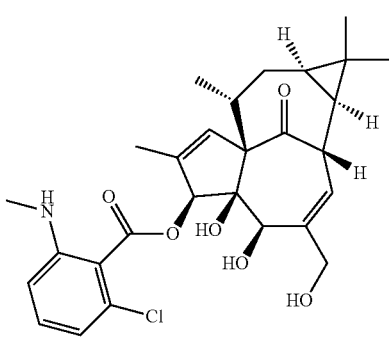

Example 342

Ingenol 3-(2-chloro-6-methylamino-benzoate)
(Compound 342)

Compound 342 was prepared according to Procedure e.
Starting material: Compound 442.

¹H NMR (300 MHz, CDCl₃) δ 7.22 (t, 1H), 6.68 (dd, 1H), 6.55 (d, 1H), 6.21 (bs, 1H), 6.09-6.07 (m, 2H), 5.93 (s, 1H), 4.33 (bs, 1H), 4.23-4.10 (m, 4H), 2.83 (s, 3H), 2.59-2.54 (m, 1H), 2.43 (bs, 1H), 2.32-2.22 (m, 1H), 1.82-1.74 (m, 4H), 1.65 (bs, 1H), 1.11 (s, 3H), 1.07 (s, 3H), 0.99-0.90 (m, 4H), 0.75-0.67 (m, 1H).

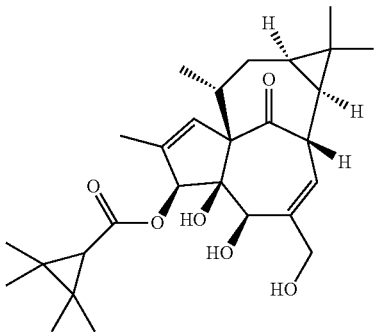

Example 344

Ingenol 3-(2,2,3,3-tetramethylcyclopropylcarboxylate)
(Compound 344)

Compound 344 was prepared according to Procedure in Example 327, but replacing Compound 427 with Compound 444.

¹H NMR (300 MHz, CDCl₃) δ 6.05-6.04 (m, 1H), 6.00 (m, 1H), 5.44 (s, 1H), 4.15-4.09 (m, 3H), 4.00 (s, 1H), 3.41 (s, 1H), 2.56-2.47 (m, 1H), 2.42-2.23 (m, 2H), 1.98-1.85 (bs, 1H), 1.82-1.58 (m, 5H), 1.26-1.25 (m, 6H), 1.22 (s, 3H), 1.21 (s, 3H), 1.11 (s, 3H), 1.06 (s, 3H), 0.99-0.86 (m, 4H), 0.74-0.66 (m, 1H).

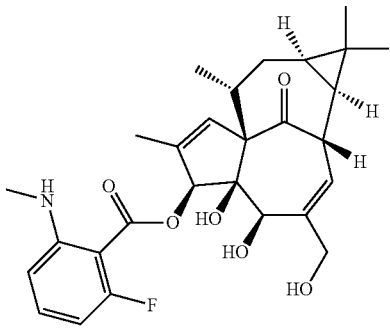

Example 343

Ingenol 3-(2-fluoro-6-methylamino-benzoate)
(Compound 343)

Compound 343 was prepared according to Procedure e.
Starting material: Compound 443.

¹H NMR (300 MHz, CDCl₃) δ 7.65-7.61 (m, 1H), 7.34-7.25 (m, 1H), 6.45 (d, 1H), 6.37-6.30 (m, 1H), 6.08-6.06 (m, 2H), 5.87 (s, 1H), 4.19-4.13 (m, 2H), 4.00 (d, 1H), 3.92 (d, 1H), 3.58 (s, 1H), 2.90 (d, 3H), 2.60-2.55 (m, 1H), 2.30-2.22 (m, 2H), 1.85 (d, 3H), 1.84-1.77 (m, 1H), 1.62 (s, 1H), 1.11 (s, 3H), 1.07 (s, 3H), 0.99-0.90 (m, 4H), 0.76-0.69 (m, 1H).

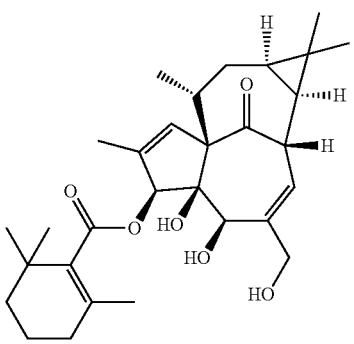 [SMILES: CC1=C[C@]23C(=O)[C@@H](C=C(CO)[C@@H](O)[C@]2(O)[C@H]1OC(=O)C1=C(C)CCCC1(C)C)[C@H]1[C@@H](C[C@H]3C)C1(C)C]

Example 345

Ingenol 3-(2,6,6-trimethylcyclohexene-1-carboxylate)
(Compound 345)

Compound 345 was prepared according to Procedure e.
Starting material: Compound 445.

¹H NMR (300 MHz, CDCl₃) δ 6.06-6.03 (m, 2H), 5.57 (s, 1H), 4.42 (d, 1H), 4.20-4.06 (m, 4H), 3.69 (s, 1H), 2.68 (bs, 1H), 2.56-2.51 (m, 1H), 2.32-2.23 (m, 1H), 2.00 (t, 2H), 1.81 (d, 3H), 1.78-1.63 (m, 6H), 1.49-1.45 (m, 2H), 1.13 (s, 3H), 1.11 (s, 3H), 1.09 (s, 3H), 1.04 (s, 3H), 0.97-0.89 (m, 4H), 0.72-0.65 (m, 1H).

Example 1

Neutrophil Oxidative Burst Assay:

PMN's (polymorphonuclear leukocytes) were isolated and purified from fresh buffy coats by sequential sedimentation, density centrifugation and lysis of contaminating erythrocytes. Buffy coats were incubated with 2% methocel for 30-45 min to differentially sediment red blood cells. The leukocyte-rich supernatant was transferred to lymphoprep tubes to remove mononuclear cells by density centrifugation (400×g, 30 min). The pellet was resuspended and any remaining erythrocytes lysed using 0.2% NaCl for 30 sec before restoring isotonicity by the addition of 1.2% NaCl. This step was repeated until the cell pellet appears relatively free of red blood cells. Cells were resuspended in DPBS (Dulbecco's Phosphate Buffered Saline) (w.o. $Ca^{2+}$, $Mg^{2+}$) and the concentration adjusted to $1.4 \times 10^6$ cells/ml in HBSS (Hanks Balanced Salt solution) (w $Ca^{2+}$, $Mg^{2+}$) containing 0.1% BSA (Bovine Serum Albumin) and 5 mM glucose just prior to assay initiation. Titrated reference and test compounds were pre-mixed with HE (Hydroethidine) (10 µM final assay concentration) before addition to 96-well plates containing $2.5 \times 10^5$ cells. Following 40 min incubation at RT, changes in the respiratory burst was estimated by measuring fluorescence at 579 nm (excitation: 485 nm) using an Envision plate reader.

Test compound titration curves were fitted to a four-parameter sigmoidal curve after normalizing the effect of the test compound to the effect of the positive control ($5 \times 10^{-7}$ M PEP0005). Rel $EC_{50}$ denotes the concentration of test compound producing an effect that is midway between the fitted top and bottom. Abs $EC_{50}$ is the concentration of test compound that provokes a response corresponding to 50% of the maximal effect associated with the positive control ($5 \times 10^{-7}$ M PEP0005).

Example 2

HeKa Cytokine Release (IL-8) Assay:

Primary human epidermal keratinocytes, HeKa, were seeded (10.000 cells/well) in 96-well plates the day before the assay. Test compounds were diluted in DMSO (dimethyl sulfoxide) and further diluted in assay medium and pipetted into wells of 96 well-plates containing HeKa cells. The plates were incubated for 6 h at 37° C. in humidified air with 5% $CO_2$. Plates are centrifuged briefly to spin down cells at 4° C., the supernatant was removed and analysed by Meso Scale Discovery (MSD) 4-spot cytokine assay (Pro-inflammatory II Ultra Sensitive kit, MSD, MD, USA). The MSD assay employs a sandwich immunoassay format where capture antibodies were coated in a patterned array on the bottom of the wells of a 4-Spot-Multi-MSD plate. Standard samples were incubated in the MULTI-SPOT plates as well, and the cytokine (IL-8) binds to its corresponding capture antibody spot. The cytokine level was quantitated on a SECTOR™ Imager using a cytokine-specific Detection Antibody labelled with MSD SULFO-TAG™ reagent.

Test compound titration curves were fitted to a four-parameter sigmoidal curve after normalizing the effect of the test compound to the effect of the positive control ($1.5 \times 10^{-7}$ M PEP0005). Rel $EC_{50}$ denotes the concentration of test compound producing an effect that is midway between the fitted top and bottom. Abs $EC_{50}$ is the concentration of test compound that provokes a response corresponding to 50% of the maximal effect associated with the positive control ($1.5 \times 10^{-7}$ M PEP0005).

Example 3

Necrosis Assay

HeLa cells (ATCC CCL-002) were grown in minimal essential medium (Invitrogen catalog no. 42360) containing 10% fetal bovine serum, 100 IU/ml penicillin and 100 µg/ml streptomycin. 4,000-6,000 cells were seeded into 96-well black ViewPlates-plates, clear bottom, (Perkin Elmer) in 100 µl medium and incubated overnight. Compounds were dissolved and pre-diluted in DMSO in 96-well polypropylene plates (Greiner) in a concentration range of 15 µM to 600 µM. At the time of the experiment cell plates were placed on heating blocks at 37° C., medium was removed and 40 µl fresh, pre-warmed medium was added per well. Cells were incubated for 15 min before addition of compounds. In parallel, 3 µl of compounds were diluted with 197 µl growth medium on a Tecan freedom-EVO pipetting station using 250 µl/s pipetting speed, in order to ensure effective mixing of the highly concentrated compound solutions with the aqueous phase. These pre-dilution plates were then equilibrated on heating blocks at 37° C. for 10 min. 80 µl pre-diluted compound were transferred manually to the corresponding wells containing HeLa cells yielding compound concentrations of 10 µM to 400 µM. Control conditions were 1% DMSO in growth medium (100% viability) and 400 µM ingenol mebutate in growth medium (0% viability). Plates were incubated on the heating blocks at 37° C. for 30 min. At the end of the incubation 10 µl PrestoBlue reagent (Invitrogen) were added to each well, plates were sealed with black seal, followed by incubation at 37° C. for 10 min with gentle shaking (150 rpm). Subsequently, plates were placed at room temperature for 20-30 min. Plates were read immediately after on an Envision Fluorescence reader (Perkin Elmer) with excitation at 535 nm and emission at 630 nm. Test compound titration curves were fitted to a four-parameter sigmoidal curve after normalizing the effect of the test compound to the effect of the positive control ($4 \times 10^{-4}$ M PEP0005/ingenol mebutate). Abs$EC_{50}$ denotes the concentration of test compound producing 50% effect.

Compounds of the present invention were tested in the neutrophil oxidative burst assay according to the description in example 1, in the HeKa cytokine release assay according to the description in example 2 and in the necrosis assay according to the description in example 3.

Neutrophil oxidative burst Rel $EC_{50}$ ranges
* indicates that Rel $EC_{50}$ values are ≥100 nM
** indicates that Rel $EC_{50}$ values are ≥20 nM and <100 nM
*** indicates that Rel $EC_{50}$ values are <20 nM HeKa cytokine release (IL-8) Rel $EC_{50}$ ranges
* indicates that Rel $EC_{50}$ values are ≥100 nM
** indicates that Rel $EC_{50}$ values are ≥20 nM and <100 nM
*** indicates that Rel $EC_{50}$ values are <20 nM HeLa Necrosis $EC_{50}$ ranges
* indicates that $EC_{50}$ values are ≥350 µM
** indicates that $EC_{50}$ values are ≥150 µM and <350 µM
*** indicates that $EC_{50}$ values are <150 µM

| Compound name and number | Neutrophil oxidative burst Rel $EC_{50}$ range | HeKa cytokine release (IL-8) Rel $EC_{50}$ range | HeLa necrosis $EC_{50}$ range |
|---|---|---|---|
| Ingenol 3-(cyclopropanecarboxylate) (Compound 301) | ** | * | — |

| Compound name and number | Neutrophil oxidative burst Rel $EC_{50}$ range | HeKa cytokine release (IL-8) Rel $EC_{50}$ range | HeLa necrosis $EC_{50}$ range |
|---|---|---|---|
| Ingenol 3-(cyclohexanecarboxylate) (Compound 302) | *** | ** | ** |
| Ingenol 3-(cyclobutanecarboxylate) (Compound 303) | *** | * | — |
| Ingenol 3-(cyclopentanecarboxylate) (Compound 304) | *** | ** | — |
| Ingenol 3-(cyclohexene-1-carboxylate) (Compound 305) | *** | *** | — |
| Ingenol 3-(1-methoxycarbonyl-cyclopropylcarboxylate) (Compound 306) | ** | * | * |
| Ingenol 3-(noradamantane-3-carboxylate) (Compound 307) | *** | *** | ** |
| Ingenol 3-(1-methyl-cyclohexanecarboxylate) (Compound 308) | *** | *** | *** |
| Ingenol 3-(1-cyano-cyclohexanecarboxylate) (Compound 309) | *** | — | — |
| Ingenol 3-(2-methyl-benzoate) (Compound 310) | *** | *** | — |
| Ingenol 3-(4-fluoro-benzoate) (Compound 311) | *** | *** | *** |
| Ingenol 3-(2-methoxy-benzoate) (Compound 312) | *** | ** | *** |
| Ingenol 3-(4-methoxy-benzoate) (Compound 313) | *** | *** | *** |
| Ingenol 3-(2,4-difluoro-benzoate) (Compound 314) | *** | *** | *** |
| Ingenol 3-(2,6-dimethyl-benzoate) (Compound 315) | *** | ** | *** |
| Ingenol 3-(2,6-dimethoxy-benzoate) (Compound 316) | ** | ** | ** |
| Ingenol 3-(2,6-dichloro-benzoate) (Compound 317) | ** | *** | — |
| Ingenol 3-(2,4,6-trichloro-benzoate) (Compound 318) | ** | *** | — |
| Ingenol 3-(naphthalene-1-carboxylate) (Compound 319) | *** | *** | *** |
| Ingenol 3-(2-phenyl-benzoate) (Compound 320) | *** | *** | *** |
| Ingenol 3-(2-bromo-benzoate) (Compound 321) | *** | *** | *** |
| Ingenol 3-(2-phenoxy-benzoate) (Compound 322) | *** | *** | *** |
| Ingenol 3-(2-isopropyl-benzoate) (Compound 323) | *** | *** | *** |
| Ingenol 3-(2-isopropoxy-benzoate) (Compound 324) | *** | *** | *** |
| Ingenol 3-(2,4,6-trimethyl-benzoate) (Compound 325) | *** | *** | *** |
| Ingenol 3-(2-allyloxy-6-methyl-benzoate) (Compound 326) | *** | — | *** |
| Ingenol 3-(2-hydroxy-6-methyl-benzoate) (Compound 327) | *** | — | ** |
| Ingenol 3-(2-chloro-6-methyl-benzoate) (Compound 328) | *** | — | *** |
| Ingenol 3-(2,4-dimethoxy-6-methyl-benzoate) (Compound 329) | *** | — | *** |
| Ingenol 3-(2-amino-benzoate) (Compound 330) | *** | *** | ** |
| Ingenol 3-(2-benzylamino-benzoate) (Compound 331) | *** | *** | *** |
| Ingenol 3-(2-benzylamino-6-methyl-benzoate) (Compound 332) | ** | *** | *** |
| Ingenol 3-(2-benzylamino-6-methoxy-benzoate) (Compound 333) | ** | *** | *** |
| Ingenol 3-(2-amino-6-methoxy-benzoate) (Compound 334) | ** | ** | — |
| Ingenol 3-(2-amino-6-methyl-benzoate) (Compound 335) | *** | *** | *** |
| Ingenol 3-(2-phenylamino-benzoate) (Compound 336) | *** | *** | *** |
| Ingenol 3-(2-acetylamino-6-methyl-benzoate) (Compound 337) | * | * | — |
| Ingenol 3-(2-methyl-6-(2-methylpropanoylamino)-benzoate) (Compound 338) | * | * | — |
| Ingenol 3-(2-methyl-6-methylamino-benzoate) (Compound 339) | ** | *** | *** |
| Ingenol 3-(2-amino-6-chloro-benzoate) (Compound 340) | *** | ** | *** |
| Ingenol 3-(2-amino-6-fluoro-benzoate) (Compound 341) | *** | *** | *** |
| Ingenol 3-(2-chloro-6-methylamino-benzoate) (Compound 342) | ** | *** | *** |
| Ingenol 3-(2-fluoro-6-methylamino-benzoate) (Compound 343) | *** | *** | *** |
| Ingenol 3-(2,2,3,3-tetramethylcyclopropylcarboxylate) (Compound 344) | *** | *** | — |
| Ingenol 3-(2,6,6-trimethylcyclohexene-1-carboxylate) (Compound 345) | *** | *** | *** |
| Ingenol-3-angelate | *** | *** | ** |

Example 4

Chemical Stability Assay at Room Temperature, Buffer pH 7.4

A stock solution was prepared by diluting 50 ul of a ~10 mM DMSO solution of the compound with 1.15 ml acetonitrile (Analytical grade). To 0.75 ml stock solution 2.25 ml Phosphatebuffer (0.067 M) pH 7.4 was added. After filtering (Millipore filter: Millex-LCR (SLCR013NL)) the solution was placed in an HPLC autosampler (room temperature). The solution was repeatedly injected over a period of 16 hours.

HPLC System:

Stationary Phase: Chromolith Performance RP18(4.6×100 mm, 2 μm)

Mobile Phase: A: 25 mM Phosphatebuffer B: Acetonitrile

Based on the decrease of area of the compound signal (UV detection, suitable wavelength) the recovery of the compound over time was assessed.

Data Analysis:

Detection: UV: 235 nm

The absolute area under the curve at t=0 hours equals to 100% recovery.

Calculation of the single recovery values at the measured timepoints:

Recovery [%] at $t_x$:[Area under the curve($t_x$)/Area under the curve($t_0$)]*100

Some compounds of the present invention were tested in Chemical Stability assay at room temperature, buffer pH 7.4. Tested compounds of the present invention exhibiting improved chemical stability in that assay compared to ingenol-3-angelate are shown in the table below.

| Compound name and number | Recovery [%] at 16 h, rt, buffer pH 7.4 |
|---|---|
| Ingenol 3-(2-chloro-6-methyl-benzoate) (Compound 328) | 95 |
| Ingenol 3-(2-amino-6-chloro-benzoate) (Compound 340) | 93 |
| Ingenol 3-(2-amino-6-methyl-benzoate) (Compound 335) | 95 |
| Ingenol 3-(2-fluoro-6-methylamino-benzoate) (Compound 343) | 74 |
| Ingenol 3-(2-amino-6-fluoro-benzoate) (Compound 341) | 66 |
| Ingenol 3-(2,6-dimethyl-benzoate) (Compound 315) | 95 |
| Ingenol 3-(2,4-dimethoxy-6-methyl-benzoate) (Compound 329) | 95 |
| Ingenol 3-(2-chloro-6-methylamino-benzoate) (Compound 342) | 95 |
| Ingenol-3-angelate | 61 |

The invention claimed is:

1. A compound of the general formula I

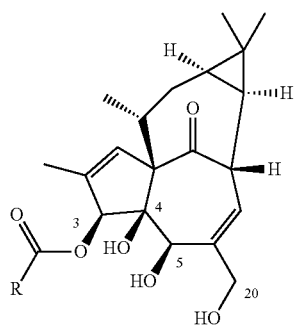

wherein
- R is phenyl which is ortho-substituted relative to the carbonyl group by two substituents independently selected from R3;
- R3 represents aryl, $(C_1-C_4)$-alkyl, —ORa, —NRaCORb, hydroxyl, cyano, halogen or —NRdRe;
- Ra and Rb independently represent hydrogen, $(C_1-C_4)$-alkyl, $(C_2-C_4)$-alkenyl or aryl;
- Rd and Re independently represent hydrogen, $(C_1-C_4)$-alkyl, aryl or arylalkyl;

and pharmaceutically acceptable salts, hydrates and solvates thereof.

2. A compound according to claim 1, wherein Rd and Re independently represents hydrogen, $(C_2-C_4)$-alkyl, aryl, or arylalkyl.

3. A compound according to claim 1, wherein R3 is independently selected one or more times from aryl, $(C_1-C_4)$-alkyl, —ORa, —NRaCORb, hydroxyl, cyano and halogen.

4. A compound according to claim 1, said compound being:
- Ingenol 3-(2,6-dichloro-benzoate),
- Ingenol 3-(2,6-dimethoxy-benzoate),
- Ingenol 3-(2,6-dimethyl-benzoate),
- Ingenol 3-(2,4-difluoro-benzoate),
- Ingenol 3-(2-allyloxy-6-methyl-benzoate),
- Ingenol 3-(2-hydroxy-6-methyl-benzoate),
- Ingenol 3-(2-chloro-6-methyl-benzoate),
- Ingenol 3-(2-benzylamino-6-methyl-benzoate),
- Ingenol 3-(2-benzylamino-6-methoxy-benzoate),
- Ingenol 3-(2-amino-6-methoxy-benzoate),
- Ingenol 3-(2-amino-6-methyl-benzoate),
- Ingenol 3-(2-acetylamino-6-methyl-benzoate),
- Ingenol 3-(2-methyl-6-(2-methylpropanoylamino)-benzoate),
- Ingenol 3-(2-methyl-6-methylamino-benzoate),
- Ingenol 3-(2-amino-6-chloro-benzoate),
- Ingenol 3-(2-amino-6-fluoro-benzoate),
- Ingenol 3-(2-chloro-6-methylamino-benzoate), or
- Ingenol 3-(2-fluoro-6-methylamino-benzoate), and pharmaceutically acceptable salts thereof.

5. A method of treating genital warts, actinic keratosis, squamous cell carcinoma (SCC), basal cell carcinoma (BCC), and seborrheic keratosis by administration to a subject in need thereof a compound according to claim 1.

6. A pharmaceutical composition comprising a compound according to claim 1 together with a pharmaceutically acceptable vehicle or excipient.

7. A pharmaceutical composition according to claim 6, wherein the composition is suitable for topical administration.

* * * * *